US006277613B1

(12) United States Patent
De Lange et al.

(10) Patent No.: US 6,277,613 B1
(45) Date of Patent: Aug. 21, 2001

(54) TRF1 BINDING PROTEIN, METHODS OF USE THEREOF

(75) Inventors: Titia De Lange; Susan Smith, both of New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 09/196,387

(22) Filed: Nov. 19, 1998

Related U.S. Application Data

(63) Continuation-in-part of application No. 09/135,233, filed on Aug. 17, 1998, now abandoned, which is a continuation-in-part of application No. 09/095,225, filed on Jun. 10, 1998, now abandoned.

(51) Int. Cl.[7] .................................................... C12N 9/10
(52) U.S. Cl. ............................................................ 435/193
(58) Field of Search ..................................... 435/193, 69.7

(56) References Cited

U.S. PATENT DOCUMENTS 5,733,730   3/1998   DeLang ..................................... 435/6

FOREIGN PATENT DOCUMENTS

WO 97/08314   3/1994   (WO) .

OTHER PUBLICATIONS

Agard et al., 1983, Nature, 302:676–81.
Allsopp et al., 1992, Proc Natl Acad Sci USA, 89:10114–8.
Bilaud et al., 1996, Nucl Acid Res, 24:1294–1303.
Blackburn et al., 1978, J Mol Biol, 120:33–53.
Bodner et al., 1998, Science, 279:349–52.
Broccoli et al., 1995, Proc Natl Acad Sci USA, 92:9082–6.
Broccolu et al., 1997, Hum Mol Genetics, 6:69–76.
Chong et al., 1995, Science, 270:1663–7.
de Lange, 1994, Proc Natl Acad Sci USA, 91:2882–5.
Greider et al., 1985, Cell, 43:405–13.
Harley et al., 1990, Nature(London), 345:458–60.
Harley et al., 1992, Exp Gerontol, 27:375–82.
Hanish et al., 1994, Proc Natl Acad Sci USA, 91:8861–5.
Hollenberg et al., 1995, Mol Cell Biol, 15:3813–22.
Klobutcher et al., 1981, Proc Natl Acad Sci USA, 78:3015–9.
Kumazaki et al., 1993, J Med Sci, 42:97.
Lundblad et al., 1989, Cell, 57:633–43.
Luderus eta l., 1996, j Cell Biol, 135:867–81.
Metccalfe et al., 1996, Nature Genetics, 13:350–3.
Pluta et al., 1989, Nature, 337:429–33.
Richards et al., 1988, Cell, 53:127–36.
Sandell et al., 1993, Cell, 75:729–41.
Shore, 1994, Trends Gen, 10:408–12.
Smith et al., 1997, Trends in Genetics, 13:21–6.
Tombran–Tink, 1995, J. Neurosci. 15(7):4992–5003.
West et al., 1994, Arch Dermatol, 130:87.
Yu et al., 1990, Nature, 344:126–32.
Wastson et al., 1972, Nature, 239:197–201.
Zhong et al., 1992, Mol Cell Biol, 12:4834–4843.
Burkle et al., 1998, Exp Gerontol, 33:519–23.
Jeggo et al., 1998, Curr Biol , 8:R49–51.
Smith et al., 1998, Science, 282:1484–7.
Steensel Van et al, 1997, Nature, 385:740–3.
Vasiri et al., 1997, EMBO J, 16:6018–33.

*Primary Examiner*—Charles L. Patterson, Jr.
(74) *Attorney, Agent, or Firm*—Klauber & Jackson

(57) ABSTRACT

The present invention discloses a unique vertebrate protein, tankyrase that binds to telomeric repeat binding factor 1 (TRF1). Nucleic acids encoding tankyrases are also disclosed. Methods of screening drugs using tankyrase are also included.

32 Claims, 14 Drawing Sheets

FIG. 1B

```
   1 MAASRRSQHHHHHHQQQLQPAPGASAPPPPPPPPLSPGLAPGTTPAS
  48 PTASGLAPFASPRHGLALPEGDGSRDPPDRPRSPDPVDGTSCCSTTS
  95 TICTVAAAPVVPAVSTSSAAGVAPNPAGSGSNNSPSSSSSPTSSSSS
 142 SPSSPGSSLAESPEAAGVSSTAPLGPGAAGPGTGVPAVS

181 GALRELLEACRNGDVSR-VKRLVDAANVNAKDM
 213 AGRKSLHFAAGFGRKDVVEHLLQMGANVHARDD         SP
 247 GGLIPLHNACSFGHAEVVSLLLCQGADPNARDN
 281 WNYTPLHEAAIKGKIDVCIVLLQHGADPNIRNT
 314 DGKSALDLA----DPSAKAVLTGEYKKDE
 339 L----LEAARSGNEEKLMALL----TPINVNCH         ASDGRKS-
 371 ---TPLHLAAGYNRVRIVQLLQHGADVHAKDK
 401 GGLVPLHNACSYGHYEVTELLLKHGACVNAMDL
 434 WQFTPLHEAASKNRVEVCSLLLSHGADPTLVNC
 467 HGKSAVDMAPTPELRERLTYLLQAAREADLAKV         EFKGHS
 506 KKTLALEIALHCARKQVTELLLRKGANVNEKNK         INFKQPQSH, VASLHPK
 557 DFMTPLHVAAERAHNDVMEVLHKHGAKMNALDT
 587 LGQTALHRAALAGHLQTCRLLLSYGSDPSIISL
 623 QGFTAAQMG-----NEAVQQILSESTPI--RTS
 649 DVDYRLLEASKAGDLETVKQLSSQNVNCRDLEG         C
 683 RHSTPLHFAAGYNRVSVVEYLLHHGADVHAKDK
 716 GGLVPLHNACSYGHYEVAELLVRHGASVNVADL
 749 WKFTPLHEAAAKGKYEICKLLLKHGADPTKKNR
 782 DGNTPLDLVKEQDLLKGDAALLDAAKKGCLARV         GDTDI
 820 QKLTPLHLAAGYNNLEVAEYLLEHGADVNAQDK         CTPENINCRDTQGRNS
 869 GGLIPLHNAASYGHVDIAALLIKYNTCVNATDK
 902 WAFTPLHEAAQKGRTQLCALLLAHGADPTMKNQ
 935 EGQTPLDLATADDIRALLIDAMPPEAKPQATVV         LPTCF
 936 SASSPASTPSCLSAASSIDNLTGPLAELAVSNA         LI, GGA

1011 GDGAAGTERKEGEVAGLDMNISQFLKSLGLEHLRDIFETEQITLDVL

1058 ADMGHEELKEIGINAYGHRHKLIKGVERLLGGQQGTNPYLTFHCVNQ

1105 GTILLDLAPEDKEYQSVEEEMQSTIREHRDGGNAGGIFNRYNVIRIQ

1152 KVVNKKLRERFCHRQKEVSEENHNHHNERMLFHGSPFINAIIHKGFD

1199 ERHAYIGGMFGAGIYFAENSSKSNQYVYGIGGGTGCPTHKDRSCYIC

1246 HRQMLFCRVTLGKSFLQFSTMKMAHAPPGHHSVIGRPSVNGLAYAEY

1293 VIYRGEQAYPEYLITYQIMKPEAPSQTATAAEQKT    1327
```

FIG. 1C

```
Hu Tankyrin   809  EVAGLDMNISQFIKSLGLEHLRDIFETE-QITLDVLADMGHEELKEIGINAYGHRHKLIKGVERLLG
DM Bicaud    1023  MQLAKHKDIQTLLTSLGLEHYIKIFVLN-EIDLEVFTTLTEENLMELGIAAFGARKKLLTAIHTLLA
Hu Diacyl    1089  VHLWGTEEVAAWLEHLSLCEYKDIFTRH-DIRGSELLHLERRDLKDLGVTKVGHMKRILCGIKELSR
Gg CEK9       927  -DFPSLSNAHEWLDAIKMGRYKENFDQAGLITFDVISRMTLEDLQRIGITLVGHQKILNSIQLMKV
```

FIG. 1D

```
                                                        c                              d
Hs Tankyrin  1176  HHNERMLFHGSPFIN---AIIHKGFDERHA------YIGGMFGAGIYFAENSSKSNQYVYGIG
Dm Tankyrin     1  QSNERMXFHGSPFIN---AIVQRGFDERHA------YIGGMFGAGIYFAEHSSKSNQYVYGIG
Hs PARP       854  LHNRRILWHGSRTTNFAGILSQGLRIAPPE------APVTGYMFGKGIYFADMVSKSANYHTSQ
Dm PARP       836  LHNRKLIWHGSRLTNFVGILSHGLRIAPPE------APPTGIMFGKGIYFADMVSKSANYCCTSQ
Hs KIAA017    337  LGNVRPLLHGSPVQNIVGILCRGLLLPKVEDRGVQRTDVGNLGSGIYFSDSLSTSIKYSHPGE
                     *   *                                              *  * e                          f                g
Hs Tankyrin  1230  GGTGCPTHKDRSCYICHRQML--FCRVTLGKSF--LQFSTMKMAHAPPGHHSVIGRPSV---
Dm Tankyrin    55  GGIGCPSHKDKSCYVCPRQLL--LCRVALGKSF--LQYSAMKMAHAPPGHHSVXXRPSA---
Hs PARP       913  ------GDPIGLILLGEVALGNMYELKHAS-HISRLPKGHHSVKGLGKTTPDPS-------
Dm PARP       895  ------QNSTGLMLLSEVALGDMMECTSAK-YINKLSNNKHSCFGRGRTMPDPTK------
Hs KIAA017    400  ------TDGTRILLICDVALGKCMDLHEKDFSLTEAPPGYDSVHGVSQT------------ m                    n
Hs Tankyrin  1285  ----------NGIAYAEYVIYRGEQAYPEYLITYQIMKPE----1314
Dm Tankyrin   110  ----------GGLHFAEYVVYRGEQSYPEYLITYQIVKPD---- 139
Hs PARP       960  ANISLDGVDVPLGTGISSGVIDTSLLYNEYIVYDIAQVNLKYLLKFNFKTSLW 1014
Dm PARP       943  SYIRSDGVEIPYGETITDEHLKSSLLYNEYIVYDVAQVNIQYLFRMEFKYSY   994
Hs KIAA017    443  ASVTTDFEDDFVYKTNQVKMKYIIKFSMPGDQ----          476
                                *
```

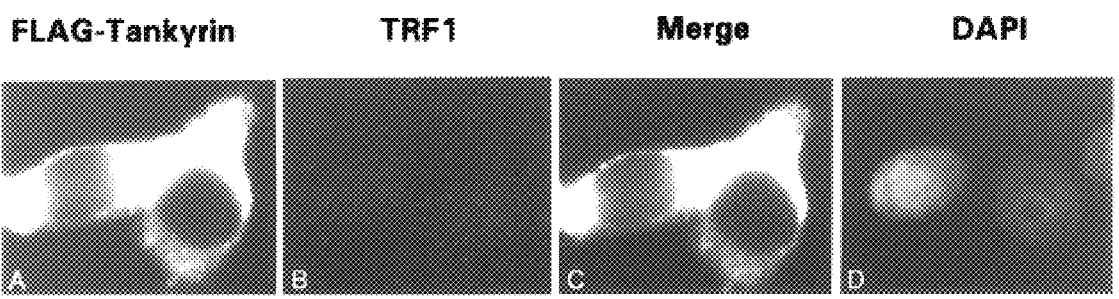
FIG. 3A FLAG-Tankyrin | FIG. 3B TRF1 | FIG. 3C Merge | FIG. 3D DAPI
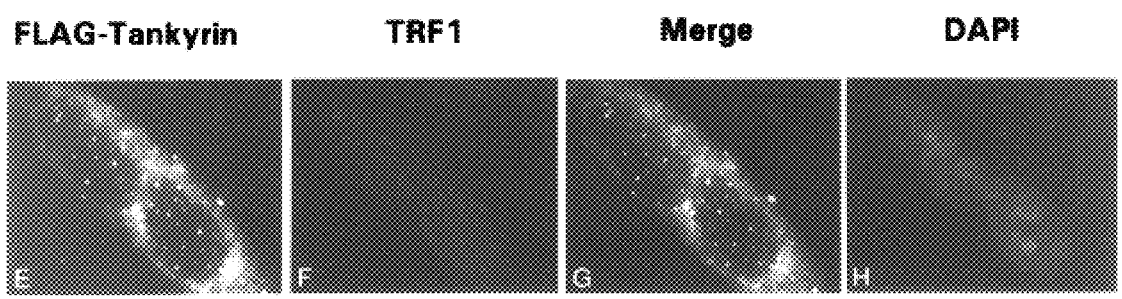
FIG. 3E FLAG-Tankyrin | FIG. 3F TRF1 | FIG. 3G Merge | FIG. 3H DAPI
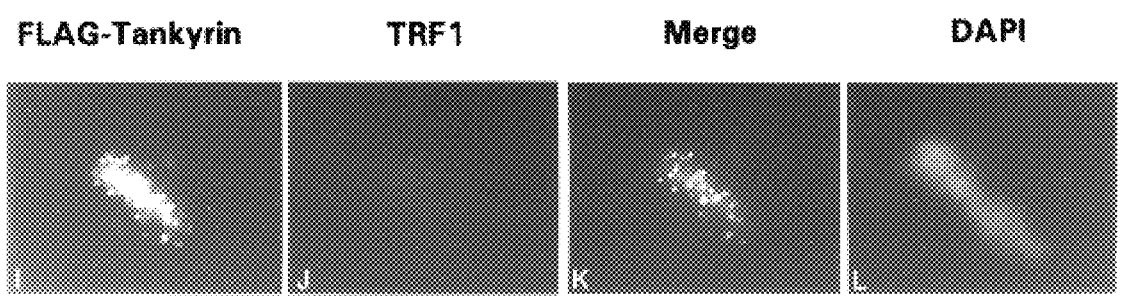
FIG. 3I FLAG-Tankyrin | FIG. 3J TRF1 | FIG. 3K Merge | FIG. 3L DAPI FIG. 7A
Tankyrin
FIG. 7B
TRF1
FIG. 7C
Merge
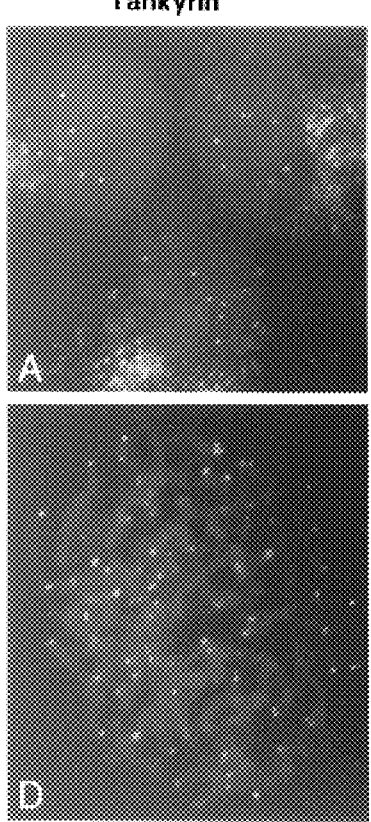
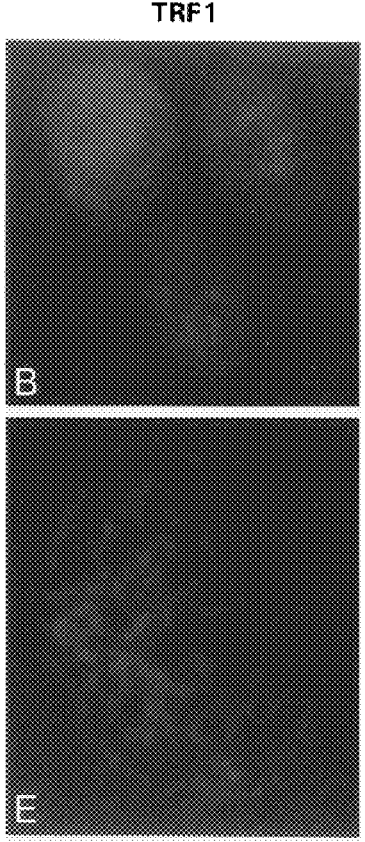
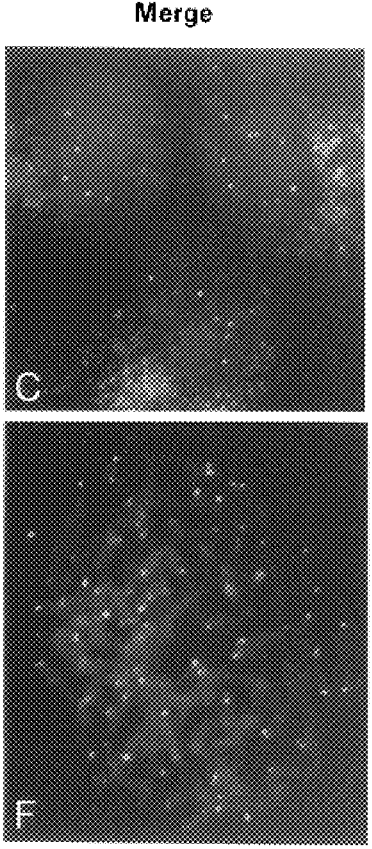
FIG. 7D
FIG. 7E
FIG. 7F Prophase of meiosis I TRF1-tankyrin interaction at the nuclear envelope TRF1-tankyrin interaction near the centrosome Telomere length regulation Coomassie-Blue    $^{32}$P-ADP-ribose $^{32}$P-ADP-ribose

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
      (A) LENGTH: 4134 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (xi) SEQUENCE DESCRIPTION: SEQ ID NO: 1:

-continued

```
CGAAGATGGC GGCGTCGCGT CGCTCTCAGC ATCATCACCA CCATCATCAA CAACAGCTCC      60
AGCCCGCCCC AGGGGCTTCA GCGCCGCCGC CGCCACCTCC TCCCCCACTC AGCCCTGGCC     120
TGGCCCCGGG GACCACCCCA GCCTCTCCCA CGGCCAGCGG CCTGGCCCCC TTCGCCTCCC     180
CGCGGCACGG CCTAGCGCTG CCGGAGGGGG ATGGCAGTCG GGATCCGCCC GACAGGCCCC     240
GATCCCCGGA CCCGGTTGAC GGTACCAGCT GTTGCAGTAC CACCAGCACA ATCTGTACCG     300
TCGCCGCCGC TCCCGTGGTC CCAGCGGTTT CTACTTCATC TGCCGCTGGG GTCGCTCCCA     360
ACCCAGCCGG CAGTGGCAGT AACAATTCAC CGTCGTCCTC TTCTTCCCCG ACTTCTTCCT     420
CATCTTCCTC TCCATCCTCC CCTGGATCGA GCTTGGCGGA GAGCCCCGAG GCGGCCGGAG     480
TTAGCAGCAC AGCACCACTG GGGCCTGGGG CAGCAGGACC TGGGACAGGG GTCCCAGCAG     540
TGAGCGGGGC CCTACGGGAA CTGCTGGAGG CCTGTCGCAA TGGGGACGTG TCCCGGGTAA     600
AGAGGCTGGT GGACGCGGCA AACGTAAATG CAAAGGACAT GGCCGGCCGG AAGTCTTCTC     660
CCCTGCACTT CGCTGCAGGT TTTGGAAGGA AGGATGTTGT AGAACACTTA CTACAGATGG     720
GTGCTAATGT CCACGCTCGT GATGATGGAG GTCTCATCCC GCTTCATAAT GCCTGTTCTT     780
TTGGCCATGC TGAGGTTGTG AGTCTGTTAT TGTGCCAAGG AGCTGATCCA AATGCCAGGG     840
ATAACTGGAA CTATACACCT CTGCATGAAG CTGCTATTAA AGGGAAGATC GATGTGTGCA     900
TTGTGCTGCT GCAGCACGGA GCTGACCCAA ACATTCGGAA CACTGATGGG AAATCAGCCC     960
TGGACCTGGC AGATCCTTCA GCAAAAGCTG TCCTTACAGG TGAATACAAG AAAGACGAAC    1020
TCCTAGAAGC TGCTAGGAGT GGTAATGAAG AAAAACTAAT GGCTTTACTG ACTCCTCTAA    1080
ATGTGAATTG CCATGCAAGT GATGGGCGAA AGTCGACTCC TTTACATCTA GCAGCGGGCT    1140
ACAACAGAGT TCGAATAGTT CAGCTTCTTC TTCAGCATGG TGCTGATGTT CATGCAAAAG    1200
ACAAAGGTGG ACTTGTGCCT CTTCATAATG CATGTTCATA TGGACATTAT GAAGTCACAG    1260
AACTGCTACT AAAGCATGGA GCTTGTGTTA ATGCCATGGA TCTCTGGCAG TTTACTCCAC    1320
TGCACGAGGC TGCTTCCAAG AACCGTGTAG AAGTCTGCTC TTTGTTACTT AGCCATGGCG    1380
CTGATCCTAC GTTAGTCAAC TGCCATGGCA AAAGTGCTGT GGATATGGCT CCAACTCCGG    1440
AGCTTAGGGA GAGATTGACT TATGAATTTA AGGTCATTC TTTACTACAA GCAGCCAGAG    1500
AAGCAGACTT AGCTAAAGTT AAAAAAACAC TCGCTCTGGA AATCATTAAT TTCAAACAAC    1560
CGCAGTCTCA TGAAACAGCA CTGCACTGTG CTGTGGCCTC TCTGCATCCC AAACGTAAAC    1620
AAGTGACAGA ATTGTTACTT AGAAAAGGAG CAAATGTTAA TGAAAAAAAT AAAGATTTCA    1680
TGACTCCCCT GCATGTTGCA GCCGAAAGAG CCCATAATGA TGTCATGGAA GTTCTGCATA    1740
AGCATGGCGC CAAGATGAAT GCACTGGACA CCCTTGGTCA GACTGCTTTG CATAGAGCCG    1800
CCCTAGCAGG CCACCTGCAG ACCTGCCGCC TCCTGCTGAG TTACGGCTCT GACCCCTCCA    1860
TCATCTCCTT ACAAGGCTTC ACAGCAGCAC AGATGGGCAA TGAAGCAGTG CAGCAGATTC    1920
TGAGTGAGAG TACACCTATA CGTACTTCTG ATGTTGATTA TCGACTCTTA GAGGCATCTA    1980
AAGCTGGAGA CTTGGAAACT GTGAAGCAAC TTTGCAGCTC TCAAAATGTG AATTGTAGAG    2040
ACTTAGAGGG CCGGCATTCC ACGCCCTTAC ACTTCGCAGC AGGCTACAAC CGCGTGTCTG    2100
TTGTAGAGTA CCTGCTACAC CACGGTGCCG ATGTCCATGC CAAAGACAAG GGTGGCTTGG    2160
TGCCCCTTCA TAATGCCTGT TCATATGGAC ACTATGAGGT GGCTGAGCTT TTAGTAAGGC    2220
ATGGGGCTTC TGTCAATGTG GCGGACTTAT GGAAATTTAC CCCTCTCCAT GAAGCAGCAG    2280
CTAAAGGAAA GTATGAAATC TGCAAGCTCC TTTTAAAACA TGGAGCAGAT CCAACTAAAA    2340
AGAACAGAGA TGGAAATACA CCTTTGGATT TGGTAAAGGA AGGAGACACA GATATTCAGG    2400
```

```
ACTTACTGAA AGGGGATGCT GCTTTGTTGG ATGCTGCCAA GAAGGCTGC CTGGCAAGAG      2460

TGCAGAAGCT CTGTACCCCA GAGAATATCA ACTGCAGAGA CACCCAGGGC AGAAATTCAA      2520

CCCCTCTGCA CCTGGCAGCA GGCTATAATA ACCTGGAAGT AGCTGAATAT CTTCTAGAGC      2580

ATGGAGCTGA TGTTAATGCC CAGGACAAGG GTGGTTTAAT TCCTCTTCAT AATGCGGCAT      2640

CTTATGGGCA TGTTGACATA GCGGCTTTAT TGATAAAATA CAACACGTGT GTAAATGCAA      2700

CAGATAAGTG GGCGTTTACT CCCCTCCATG AAGCAGCCCA GAAAGGAAGG ACGCAGCTGT      2760

GCGCCCTCCT CCTAGCGCAT GGTGCAGACC CCACCATGAA GAACCAGGAA GGCCAGACGC      2820

CTCTGGATCT GGCAACAGCT GACGATATCA GAGCTTTGCT GATAGATGCC ATGCCCCCAG      2880

AGGCCTTACC TACCTGTTTT AAACCTCAGG CTACTGTAGT GAGTGCCTCT CTGATCTCAC      2940

CAGCATCCAC CCCCTCCTGC CTCTCGGCTG CCAGCAGCAT AGACAACCTC ACTGGCCCTT      3000

TAGCAGAGTT GGCCGTAGGA GGAGCCTCCA ATGCAGGGGA TGGCGCCGCG GGAACAGAAA      3060

GGAAGGAAGG AGAAGTTGCT GGTCTTGACA TGAATATCAG CCAATTTCTA AAAAGCCTTG      3120

GCCTTGAACA CCTTCGGGAT ATCTTTGAAA CAGAACAGAT TACACTAGAT GTGTTGGCTG      3180

ATATGGGTCA TGAAGAGTTG AAAGAAATAG GCATCAATGC ATATGGGCAC CGCCACAAAT      3240

TAATCAAAGG AGTAGAAAGA CTCTTAGGTG ACAACAAGG CACCAATCCT TATTTGACTT      3300

TTCACTGTGT TAATCAGGGA ACGATTTTGC TGGATCTTGC TCCAGAAGAT AAAGAATATC      3360

AGTCAGTGGA AGAAGAGATG CAAAGTACTA TTCGAGAACA CAGAGATGGT GGTAATGCTG      3420

GCGGCATCTT CAACAGATAC AATGTCATTC GAATTCAAAA AGTTGTCAAC AAGAAGTTGA      3480

GGGAGCGGTT CTGCCACCGA CAGAAGGAAG TGTCTGAGGA GAATCACAAC CATCACAATG      3540

AGCGCATGTT GTTTCATGGT TCTCCTTTCA TTAATGCCAT TATTCATAAA GGGTTTGATG      3600

AGCGACATGC ATACATAGGA GGAATGTTTG GGGCCGGGAT TTATTTTGCT GAAAACTCCT      3660

CAAAAAGCAA CCAATATGTT TATGGAATTG GAGGAGGAAC AGGCTGCCCT ACACACAAGG      3720

ACAGGTCATG CTATATATGT CACAGACAAA TGCTCTTCTG TAGAGTGACC CTTGGGAAAT      3780

CCTTTCTGCA GTTTAGCACC ATGAAAATGG CCCACGCGCC TCCAGGGCAC CACTCAGTCA      3840

TTGGTAGACC GAGCGTCAAT GGGCTGGCAT ATGCTGAATA TGTCATCTAC AGAGGAGAAC      3900

AGGCATACCC AGAGTATCTT ATCACTTACC AGATCATGAA GCCAGAAGCC CCTTCCCAGA      3960

CCGCAACAGC CGCAGAGCAG AAGACCTAGT GAATGCCTGC TGGTGAAGGC CAGATCAGAT      4020

TTCAACCTGG GACTGGATTA CAGAGGATTG TTTCTAATAA CAACATCAAT ATTCTAGAAG      4080

TCCCTGACAG CCTAGAAATA AGCTGTTTGT CTTCTATAAA GCATTGCTAT AGTG           4134
```

(2) INFORMATION FOR SEQ ID NO: 2:

(i) SEQUENCE CHARACTERISTICS:
        (A) LENGTH: 1327 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO: 2:

```
Met Ala Ala Ser Arg Arg Ser Gln His His His His His Gln Gln
1               5                   10                  15

Gln Leu Gln Pro Ala Pro Gly Ala Ser Ala Pro Pro Pro Pro Pro
            20                  25                  30
```

```
Pro Pro Leu Ser Pro Gly Leu Ala Pro Gly Thr Thr Pro Ala Ser Pro
         35                  40                  45

Thr Ala Ser Gly Leu Ala Pro Phe Ala Ser Pro Arg His Gly Leu Ala
     50                  55                  60

Leu Pro Glu Gly Asp Gly Ser Arg Asp Pro Asp Arg Pro Arg Ser
 65                  70                  75                  80

Pro Asp Pro Val Asp Gly Thr Ser Cys Cys Ser Thr Thr Ser Thr Ile
                 85                  90                  95

Cys Thr Val Ala Ala Pro Val Val Pro Ala Val Ser Thr Ser Ser
             100                 105                 110

Ala Ala Gly Val Ala Pro Asn Pro Ala Gly Ser Gly Ser Asn Asn Ser
         115                 120                 125

Pro Ser Ser Ser Ser Pro Thr Ser Ser Ser Ser Ser Ser Pro Ser
     130                 135                 140

Ser Pro Gly Ser Ser Leu Ala Glu Ser Pro Glu Ala Ala Gly Val Ser
 145                 150                 155                 160

Ser Thr Ala Pro Leu Gly Pro Gly Ala Ala Gly Pro Gly Thr Gly Val
             165                 170                 175

Pro Ala Val Ser Gly Ala Leu Arg Glu Leu Leu Glu Ala Cys Arg Asn
             180                 185                 190

Gly Asp Val Ser Arg Val Lys Arg Leu Val Asp Ala Ala Asn Val Asn
         195                 200                 205

Ala Lys Asp Met Ala Gly Arg Lys Ser Ser Pro Leu His Phe Ala Ala
         210                 215                 220

Gly Phe Gly Arg Lys Asp Val Val Glu His Leu Leu Gln Met Gly Ala
 225                 230                 235                 240

Asn Val His Ala Arg Asp Asp Gly Gly Leu Ile Pro Leu His Asn Ala
             245                 250                 255

Cys Ser Phe Gly His Ala Glu Val Val Ser Leu Leu Cys Gln Gly
             260                 265                 270

Ala Asp Pro Asn Ala Arg Asp Asn Trp Asn Tyr Thr Pro Leu His Glu
         275                 280                 285

Ala Ala Ile Lys Gly Lys Ile Asp Val Cys Ile Val Leu Leu Gln His
         290                 295                 300

Gly Ala Asp Pro Asn Ile Arg Asn Thr Asp Gly Lys Ser Ala Leu Asp
 305                 310                 315                 320

Leu Ala Asp Pro Ser Ala Lys Ala Val Leu Thr Gly Glu Tyr Lys Lys
                 325                 330                 335

Asp Glu Leu Leu Glu Ala Ala Arg Ser Gly Asn Glu Glu Lys Leu Met
             340                 345                 350

Ala Leu Leu Thr Pro Leu Asn Val Asn Cys His Ala Ser Asp Gly Arg
         355                 360                 365

Lys Ser Thr Pro Leu His Leu Ala Ala Gly Tyr Asn Arg Val Arg Ile
     370                 375                 380

Val Gln Leu Leu Leu Gln His Gly Ala Asp Val His Ala Lys Asp Lys
 385                 390                 395                 400

Gly Gly Leu Val Pro Leu His Asn Ala Cys Ser Tyr Gly His Tyr Glu
                 405                 410                 415

Val Thr Glu Leu Leu Lys His Gly Ala Cys Val Asn Ala Met Asp
             420                 425                 430

Leu Trp Gln Phe Thr Pro Leu His Glu Ala Ala Ser Lys Asn Arg Val
     435                 440                 445
```

-continued

```
Glu Val Cys Ser Leu Leu Leu Ser His Gly Ala Asp Pro Thr Leu Val
    450                 455                 460
Asn Cys His Gly Lys Ser Ala Val Asp Met Ala Pro Thr Pro Glu Leu
465                 470                 475                 480
Arg Glu Arg Leu Thr Tyr Glu Phe Lys Gly His Ser Leu Leu Gln Ala
                485                 490                 495
Ala Arg Glu Ala Asp Leu Ala Lys Val Lys Lys Thr Leu Ala Leu Glu
            500                 505                 510
Ile Ile Asn Phe Lys Gln Pro Gln Ser His Glu Thr Ala Leu His Cys
        515                 520                 525
Ala Val Ala Ser Leu His Pro Lys Arg Lys Gln Val Thr Glu Leu Leu
    530                 535                 540
Leu Arg Lys Gly Ala Asn Val Asn Glu Lys Asn Lys Asp Phe Met Thr
545                 550                 555                 560
Pro Leu His Val Ala Ala Glu Arg Ala His Asn Asp Val Met Glu Val
                565                 570                 575
Leu His Lys His Gly Ala Lys Met Asn Ala Leu Asp Thr Leu Gly Gln
            580                 585                 590
Thr Ala Leu His Arg Ala Ala Leu Ala Gly His Leu Gln Thr Cys Arg
        595                 600                 605
Leu Leu Leu Ser Tyr Gly Ser Asp Pro Ser Ile Ile Ser Leu Gln Gly
    610                 615                 620
Phe Thr Ala Ala Gln Met Gly Asn Glu Ala Val Gln Gln Ile Leu Ser
625                 630                 635                 640
Glu Ser Thr Pro Ile Arg Thr Ser Asp Val Asp Tyr Arg Leu Leu Glu
                645                 650                 655
Ala Ser Lys Ala Gly Asp Leu Glu Thr Val Lys Gln Leu Cys Ser Ser
            660                 665                 670
Gln Asn Val Asn Cys Arg Asp Leu Glu Gly Arg His Ser Thr Pro Leu
        675                 680                 685
His Phe Ala Ala Gly Tyr Asn Arg Val Ser Val Val Glu Tyr Leu Leu
    690                 695                 700
His His Gly Ala Asp Val His Ala Lys Asp Lys Gly Gly Leu Val Pro
705                 710                 715                 720
Leu His Asn Ala Cys Ser Tyr Gly His Tyr Glu Val Ala Glu Leu Leu
                725                 730                 735
Val Arg His Gly Ala Ser Val Asn Val Ala Asp Leu Trp Lys Phe Thr
            740                 745                 750
Pro Leu His Glu Ala Ala Ala Lys Gly Lys Tyr Glu Ile Cys Lys Leu
        755                 760                 765
Leu Leu Lys His Gly Ala Asp Pro Thr Lys Lys Asn Arg Asp Gly Asn
    770                 775                 780
Thr Pro Leu Asp Leu Val Lys Glu Gly Asp Thr Asp Ile Gln Asp Leu
785                 790                 795                 800
Leu Lys Gly Asp Ala Ala Leu Leu Asp Ala Ala Lys Lys Gly Cys Leu
                805                 810                 815
Ala Arg Val Gln Lys Leu Cys Thr Pro Glu Asn Ile Asn Cys Arg Asp
            820                 825                 830
Thr Gln Gly Arg Asn Ser Thr Pro Leu His Leu Ala Ala Gly Tyr Asn
        835                 840                 845
Asn Leu Glu Val Ala Glu Tyr Leu Leu Glu His Gly Ala Asp Val Asn
    850                 855                 860
Ala Gln Asp Lys Gly Gly Leu Ile Pro Leu His Asn Ala Ala Ser Tyr
```

-continued

```
            865                 870                 875                 880

Gly His Val Asp Ile Ala Ala Leu Leu Ile Lys Tyr Asn Thr Cys Val
                885                 890                 895

Asn Ala Thr Asp Lys Trp Ala Phe Thr Pro Leu His Glu Ala Ala Gln
            900                 905                 910

Lys Gly Arg Thr Gln Leu Cys Ala Leu Leu Ala His Gly Ala Asp
            915                 920                 925

Pro Thr Met Lys Asn Gln Glu Gly Gln Thr Pro Leu Asp Leu Ala Thr
            930                 935                 940

Ala Asp Asp Ile Arg Ala Leu Leu Ile Asp Ala Met Pro Pro Glu Ala
945                 950                 955                 960

Leu Pro Thr Cys Phe Lys Pro Gln Ala Thr Val Val Ser Ala Ser Leu
                965                 970                 975

Ile Ser Pro Ala Ser Thr Pro Ser Cys Leu Ser Ala Ala Ser Ser Ile
                980                 985                 990

Asp Asn Leu Thr Gly Pro Leu Ala Glu Leu Ala Val Gly Gly Ala Ser
                995                 1000                1005

Asn Ala Gly Asp Gly Ala Ala Gly Thr Glu Arg Lys Glu Gly Glu Val
            1010                1015                1020

Ala Gly Leu Asp Met Asn Ile Ser Gln Phe Leu Lys Ser Leu Gly Leu
1025                1030                1035                1040

Glu His Leu Arg Asp Ile Phe Glu Thr Glu Gln Ile Thr Leu Asp Val
                1045                1050                1055

Leu Ala Asp Met Gly His Glu Glu Leu Lys Glu Ile Gly Ile Asn Ala
                1060                1065                1070

Tyr Gly His Arg His Lys Leu Ile Lys Gly Val Glu Arg Leu Leu Gly
            1075                1080                1085

Gly Gln Gln Gly Thr Asn Pro Tyr Leu Thr Phe His Cys Val Asn Gln
            1090                1095                1100

Gly Thr Ile Leu Leu Asp Leu Ala Pro Glu Asp Lys Glu Tyr Gln Ser
1105                1110                1115                1120

Val Glu Glu Glu Met Gln Ser Thr Ile Arg Glu His Arg Asp Gly Gly
                1125                1130                1135

Asn Ala Gly Gly Ile Phe Asn Arg Tyr Asn Val Ile Arg Ile Gln Lys
            1140                1145                1150

Val Val Asn Lys Lys Leu Arg Glu Arg Phe Cys His Arg Gln Lys Glu
            1155                1160                1165

Val Ser Glu Glu Asn His Asn His His Asn Glu Arg Met Leu Phe His
            1170                1175                1180

Gly Ser Pro Phe Ile Asn Ala Ile Ile His Lys Gly Phe Asp Glu Arg
1185                1190                1195                1200

His Ala Tyr Ile Gly Gly Met Phe Gly Ala Gly Ile Tyr Phe Ala Glu
                1205                1210                1215

Asn Ser Ser Lys Ser Asn Gln Tyr Val Tyr Gly Ile Gly Gly Gly Thr
            1220                1225                1230

Gly Cys Pro Thr His Lys Asp Arg Ser Cys Tyr Ile Cys His Arg Gln
            1235                1240                1245

Met Leu Phe Cys Arg Val Thr Leu Gly Lys Ser Phe Leu Gln Phe Ser
            1250                1255                1260

Thr Met Lys Met Ala His Ala Pro Pro Gly His His Ser Val Ile Gly
1265                1270                1275                1280

Arg Pro Ser Val Asn Gly Leu Ala Tyr Ala Glu Tyr Val Ile Tyr Arg
                1285                1290                1295
```

```
Gly Glu Gln Ala Tyr Pro Glu Tyr Leu Ile Thr Tyr Gln Ile Met Lys
        1300                1305                1310

Pro Glu Ala Pro Ser Gln Thr Ala Thr Ala Ala Glu Gln Lys Thr
        1315                1320                1325
```

(2) INFORMATION FOR SEQ ID NO: 3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (xi) SEQUENCE DESCRIPTION: SEQ ID NO: 3:

TTGCGGCCGC AGACGAACTC CTAGAAGCT                                29

(2) INFORMATION FOR SEQ ID NO: 4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (xi) SEQUENCE DESCRIPTION: SEQ ID NO: 4:

GCGGGCCCTA TCGAATGACA TTGTATCTGT                              30

(2) INFORMATION FOR SEQ ID NO: 5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (xi) SEQUENCE DESCRIPTION: SEQ ID NO: 5:

TTGCGGCCGC GGCGGCGTCG CGTCGCT                                   27

(2) INFORMATION FOR SEQ ID NO: 6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PRIMER"

(iii) HYPOTHETICAL: NO (xi) SEQUENCE DESCRIPTION: SEQ ID NO: 6:

TGCGGCGTCC ACCACGGT                                              18

(2) INFORMATION FOR SEQ ID NO: 7:

(i) SEQUENCE CHARACTERISTICS:
        (A) LENGTH: 4491 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 6..2027

(xi) SEQUENCE DESCRIPTION: SEQ ID NO: 7:

```
CGAAG ATG GCG GCG TCG CGT CGC TCT CAG CAT CAT CAC CAC CAT CAT         47
      Met Ala Ala Ser Arg Arg Ser Gln His His His His His His
      1               5                  10

CAA CAA CAG CTC CAG CCC GCC CCA GGG GCT TCA GCG CCG CCG CCG CCA        95
Gln Gln Gln Leu Gln Pro Ala Pro Gly Ala Ser Ala Pro Pro Pro Pro
 15              20                  25                  30

CCT CCT CCC CCA CTC AGC CCT GGC CTG GCC CCG GGG ACC ACC CCA GCC       143
Pro Pro Pro Pro Leu Ser Pro Gly Leu Ala Pro Gly Thr Thr Pro Ala
             35                  40                  45

TCT CCC ACG GCC AGC GGC CTG GCC CCC TTC GCC TCC CCG CGG CAC GGC       191
Ser Pro Thr Ala Ser Gly Leu Ala Pro Phe Ala Ser Pro Arg His Gly
         50                  55                  60

CTA GCG CTG CCG GAG GGG GAT GGC AGT CGG GAT CCG CCC GAC AGG CCC       239
Leu Ala Leu Pro Glu Gly Asp Gly Ser Arg Asp Pro Pro Asp Arg Pro
     65                  70                  75

CGA TCC CCG GAC CCG GTT GAC GGT ACC AGC TGT TGC AGT ACC ACC AGC       287
Arg Ser Pro Asp Pro Val Asp Gly Thr Ser Cys Cys Ser Thr Thr Ser
 80                  85                  90

ACA ATC TGT ACC GTC GCC GCC GCT CCC GTG GTC CCA GCG GTT TCT ACT       335
Thr Ile Cys Thr Val Ala Ala Ala Pro Val Val Pro Ala Val Ser Thr
 95                 100                 105                 110

TCA TCT GCC GCT GGG GTC GCT CCC AAC CCA GCC GGC AGT GGC AGT AAC       383
Ser Ser Ala Ala Gly Val Ala Pro Asn Pro Ala Gly Ser Gly Ser Asn
                115                 120                 125

AAT TCA CCG TCG TCC TCT TCT TCC CCG ACT TCT TCC TCA TCT TCC TCT       431
Asn Ser Pro Ser Ser Ser Ser Ser Pro Thr Ser Ser Ser Ser Ser Ser
            130                 135                 140

CCA TCC TCC CCT GGA TCG AGC TTG GCG GAG AGC CCC GAG GCG GCC GGA       479
Pro Ser Ser Pro Gly Ser Ser Leu Ala Glu Ser Pro Glu Ala Ala Gly
        145                 150                 155

GTT AGC AGC ACA GCA CCA CTG GGG CCT GGG GCA GCA GGA CCT GGG ACA       527
Val Ser Ser Thr Ala Pro Leu Gly Pro Gly Ala Ala Gly Pro Gly Thr
    160                 165                 170

GGG GTC CCA GCA GTG AGC GGG GCC CTA CGG GAA CTG CTG GAG GCC TGT       575
Gly Val Pro Ala Val Ser Gly Ala Leu Arg Glu Leu Leu Glu Ala Cys
175                 180                 185                 190

CGC AAT GGG GAC GTG TCC CGG GTA AAG AGG CTG GTG GAC GCG GCA AAC       623
Arg Asn Gly Asp Val Ser Arg Val Lys Arg Leu Val Asp Ala Ala Asn
                195                 200                 205

GTA AAT GCA AAG GAC ATG GCC GGC CGG AAG TCT TCT CCC CTG CAC TTC       671
Val Asn Ala Lys Asp Met Ala Gly Arg Lys Ser Ser Pro Leu His Phe
            210                 215                 220

GCT GCA GGT TTT GGA AGG AAG GAT GTT GTA GAA CAC TTA CTA CAG ATG       719
Ala Ala Gly Phe Gly Arg Lys Asp Val Val Glu His Leu Leu Gln Met
        225                 230                 235
```

```
GGT GCT AAT GTC CAC GCT CGT GAT GAT GGA GGT CTC ATC CCG CTT CAT        767
Gly Ala Asn Val His Ala Arg Asp Asp Gly Gly Leu Ile Pro Leu His
        240                 245                 250

AAT GCC TGT TCT TTT GGC CAT GCT GAG GTT GTG AGT CTG TTA TTG TGC        815
Asn Ala Cys Ser Phe Gly His Ala Glu Val Val Ser Leu Leu Leu Cys
255                 260                 265                 270

CAA GGA GCT GAT CCA AAT GCC AGG GAT AAC TGG AAC TAT ACA CCT CTG        863
Gln Gly Ala Asp Pro Asn Ala Arg Asp Asn Trp Asn Tyr Thr Pro Leu
                275                 280                 285

CAT GAA GCT GCT ATT AAA GGG AAG ATC GAT GTG TGC ATT GTG CTG CTG        911
His Glu Ala Ala Ile Lys Gly Lys Ile Asp Val Cys Ile Val Leu Leu
        290                 295                 300

CAG CAC GGA GCT GAC CCA AAC ATT CGG AAC ACT GAT GGG AAA TCA GCC        959
Gln His Gly Ala Asp Pro Asn Ile Arg Asn Thr Asp Gly Lys Ser Ala
            305                 310                 315

CTG GAC CTG GCA GAT CCT TCA GCA AAA GCT GTC CTT ACA GGT GAA TAC       1007
Leu Asp Leu Ala Asp Pro Ser Ala Lys Ala Val Leu Thr Gly Glu Tyr
320                 325                 330

AAG AAA GAC GAA CTC CTA GAA GCT GCT AGG AGT GGT AAT GAA GAA AAA       1055
Lys Lys Asp Glu Leu Leu Glu Ala Ala Arg Ser Gly Asn Glu Glu Lys
335                 340                 345                 350

CTA ATG GCT TTA CTG ACT CCT CTA AAT GTG AAT TGC CAT GCA AGT GAT       1103
Leu Met Ala Leu Leu Thr Pro Leu Asn Val Asn Cys His Ala Ser Asp
                355                 360                 365

GGG CGA AAG TCG ACT CCT TTA CAT CTA GCA GCG GGC TAC AAC AGA GTT       1151
Gly Arg Lys Ser Thr Pro Leu His Leu Ala Ala Gly Tyr Asn Arg Val
        370                 375                 380

CGA ATA GTT CAG CTT CTT CTT CAG CAT GGT GCT GAT GTT CAT GCA AAA       1199
Arg Ile Val Gln Leu Leu Leu Gln His Gly Ala Asp Val His Ala Lys
            385                 390                 395

GAC AAA GGT GGA CTT GTG CCT CTT CAT AAT GCA TGT TCA TAT GGA CAT       1247
Asp Lys Gly Gly Leu Val Pro Leu His Asn Ala Cys Ser Tyr Gly His
400                 405                 410

TAT GAA GTC ACA GAA CTG CTA CTA AAG CAT GGA GCT TGT GTT AAT GCC       1295
Tyr Glu Val Thr Glu Leu Leu Leu Lys His Gly Ala Cys Val Asn Ala
415                 420                 425                 430

ATG GAT CTC TGG CAG TTT ACT CCA CTG CAC GAG GCT GCT TCC AAG AAC       1343
Met Asp Leu Trp Gln Phe Thr Pro Leu His Glu Ala Ala Ser Lys Asn
                435                 440                 445

CGT GTA GAA GTC TGC TCT TTG TTA CTT AGC CAT GGC GCT GAT CCT ACG       1391
Arg Val Glu Val Cys Ser Leu Leu Leu Ser His Gly Ala Asp Pro Thr
        450                 455                 460

TTA GTC AAC TGC CAT GGC AAA AGT GCT GTG GAT ATG GCT CCA ACT CCG       1439
Leu Val Asn Cys His Gly Lys Ser Ala Val Asp Met Ala Pro Thr Pro
            465                 470                 475

GAG CTT AGG GAG AGA TTG ACT TAT GAA TTT AAA GGT CAT TCT TTA CTA       1487
Glu Leu Arg Glu Arg Leu Thr Tyr Glu Phe Lys Gly His Ser Leu Leu
480                 485                 490

CAA GCA GCC AGA GAA GCA GAC TTA GCT AAA GTT AAA AAA ACA CTC GCT       1535
Gln Ala Ala Arg Glu Ala Asp Leu Ala Lys Val Lys Lys Thr Leu Ala
495                 500                 505                 510

CTG GAA ATC ATT AAT TTC AAA CAA CCG CAG TCT CAT GAA ACA GCA CTG       1583
Leu Glu Ile Ile Asn Phe Lys Gln Pro Gln Ser His Glu Thr Ala Leu
                515                 520                 525

CAC TGT GCT GTG GCC TCT CTG CAT CCC AAA CGT AAA CAA GTG ACA GAA       1631
His Cys Ala Val Ala Ser Leu His Pro Lys Arg Lys Gln Val Thr Glu
        530                 535                 540

TTG TTA CTT AGA AAA GGA GCA AAT GTT AAT GAA AAA AAT AAA GAT TTC       1679
Leu Leu Leu Arg Lys Gly Ala Asn Val Asn Glu Lys Asn Lys Asp Phe
            545                 550                 555
```

-continued

```
ATG ACT CCC CTG CAT GTT GCA GCC GAA AGA GCC CAT AAT GAT GTC ATG    1727
Met Thr Pro Leu His Val Ala Ala Glu Arg Ala His Asn Asp Val Met
        560                 565                 570

GAA GTT CTG CAT AAG CAT GGC GCC AAG ATG AAT GCA CTG GAC ACC CTT    1775
Glu Val Leu His Lys His Gly Ala Lys Met Asn Ala Leu Asp Thr Leu
575                 580                 585                 590

GGT CAG ACT GCT TTG CAT AGA GCC GCC CTA GCA GGC CAC CTG CAG ACC    1823
Gly Gln Thr Ala Leu His Arg Ala Ala Leu Ala Gly His Leu Gln Thr
                    595                 600                 605

TGC CGC CTC CTG CTG AGT TAC GGC TCT GAC CCC TCC ATC ATC TCC TTA    1871
Cys Arg Leu Leu Leu Ser Tyr Gly Ser Asp Pro Ser Ile Ile Ser Leu
            610                 615                 620

CAA GGC TTC ACA GCA GCA CAG ATG GGC AAT GAA GCA GTG CAG CAG ATT    1919
Gln Gly Phe Thr Ala Ala Gln Met Gly Asn Glu Ala Val Gln Gln Ile
        625                 630                 635

CTG AGT GTG AGT TAC GGC TCT GAC CCC TCC ATC ATC TCC TTA CAA GGC    1967
Leu Ser Val Ser Tyr Gly Ser Asp Pro Ser Ile Ile Ser Leu Gln Gly
640                 645                 650

TTC ACA GCA GCA CAG ATG GGC AAT GAA GCA GTG CAG CAG ATT CTG AGT    2015
Phe Thr Ala Ala Gln Met Gly Asn Glu Ala Val Gln Gln Ile Leu Ser
655                 660                 665                 670

GGT CAT TCG TAG ATAGTGATCA TTCTACTTCA GCCTTAATGG TGATCTTGAG        2067
Gly His Ser  *

ACGGGAAGAT TTAGAAGGAA ATCTATCCAG CATGTCTTCA CTGTCAACAT GAAGAGTACA  2127

CCTATACGTA CTTCTGATGT TGATTATCGA CTCTTAGAGG CATCTAAAGC TGGAGACTTG  2187

GAAACTGTGA AGCAACTTTG CAGCTCTCAA AATGTGAATT GTAGAGACTT AGAGGGCCGG  2247

CATTCCACGC CCTTACACTT CGCAGCAGGC TACAACAGAG TACACCTATA CGTACTTCTG  2307

ATGTTGATTA TCGACTCTTA GAGGCATCTA AAGCTGGAGA CTTGGAAACT GTGAAGCAAC  2367

TTTGCAGCTC TCAAAATGTG AATTGTAGAG ACTTAGAGGG CCGGCATTCC ACGCCCTTAC  2427

ACTTCGCAGC AGGCTACAAC CGCGTGTCTG TTGTAGAGTA CCTGCTACAC CACGGTGCCG  2487

ATGTCCATGC CAAAGACAAG GGTGGCTTGG TGCCCCTTCA TAATGCCTGT TCATATGGAC  2547

ACTATGAGGT GGCTGAGCTT TTAGTAAGGC ATGGGGCTTC TGTCAATGTG GCGGACTTAT  2607

GGAAATTTAC CCCTCTCCAT GAAGCAGCAG CTAAAGGAAA GTATGAAATC TGCAAGCTCC  2667

TTTTAAAACA TGGAGCAGAT CCAACTAAAA AGAACAGAGA TGGAAATACA CCTTTGGATT  2727

TGGTAAAGGA AGGAGACACA GATATTCAGG ACTTACTGAA AGGGGATGCT GCTTTGTTGG  2787

ATGCTGCCAA GAAGGGCTGC CTGGCAAGAG TGCAGAAGCT CTGTACCCCA GAGAATATCA  2847

ACTGCAGAGA CACCCAGGGC AGAAATTCAA CCCCTCTGCA CCTGGCAGCA GGCTATAATA  2907

ACCTGGAAGT AGCTGAATAT CTTCTAGAGC ATGGAGCTGA TGTTAATGCC CAGGACAAGG  2967

GTGGTTTAAT TCCTCTTCAT AATGCGGCAT CTTATGGGCA TGTTGACATA GCGGCTTTAT  3027

TGATAAAATA CAACACGTGT GTAAATGCAA CAGATAAGTG GGCGTTTACT CCCCTCCATG  3087

AAGCAGCCCA GAAAGGAAGG ACGCAGCTGT GCGCCCTCCT CCTAGCGCAT GGTGCAGACC  3147

CCACCATGAA GAACCAGGAA GGCCAGACGC CTCTGGATCT GGCAACAGCT GACGATATCA  3207

GAGCTTTGCT GATAGATGCC ATGCCCCAG AGGCCTTACC TACCTGTTTT AAACCTCAGG   3267

CTACTGTAGT GAGTGCCTCT CTGATCTCAC CAGCATCCAC CCCCTCCTGC CTCTCGGCTG  3327

CCAGCAGCAT AGACAACCTC ACTGGCCCTT TAGCAGAGTT GGCCGTAGGA GGAGCCTCCA  3387

ATGCAGGGGA TGGCGCCGCG GGAACAGAAA GGAAGGAAGG AGAAGTTGCT GGTCTTGACA  3447

TGAATATCAG CCAATTTCTA AAAAGCCTTG GCCTTGAACA CCTTCGGGAT ATCTTTGAAA  3507
```

-continued

```
CAGAACAGAT TACACTAGAT GTGTTGGCTG ATATGGGTCA TGAAGAGTTG AAAGAAATAG        3567

GCATCAATGC ATATGGGCAC CGCCACAAAT TAATCAAAGG AGTAGAAAGA CTCTTAGGTG        3627

GACAACAAGG CACCAATCCT TATTTGACTT TTCACTGTGT TAATCAGGGA ACGATTTTGC        3687

TGGATCTTGC TCCAGAAGAT AAAGAATATC AGTCAGTGGA AGAAGAGATG CAAAGTACTA        3747

TTCGAGAACA CAGAGATGGT GGTAATGCTG GCGGCATCTT CAACAGATAC AATGTCATTC        3807

GAATTCAAAA AGTTGTCAAC AAGAAGTTGA GGGAGCGGTT CTGCCACCGA CAGAAGGAAG        3867

TGTCTGAGGA GAATCACAAC CATCACAATG AGCGCATGTT GTTTCATGGT TCTCCTTTCA        3927

TTAATGCCAT TATTCATAAA GGGTTTGATG AGCGACATGC ATACATAGGA GGAATGTTTG        3987

GGGCCGGGAT TTATTTTGCT GAAAACTCCT CAAAAAGCAA CCAATATGTT TATGGAATTG        4047

GAGGAGGAAC AGGCTGCCCT ACACACAAGG ACAGGTCATG CTATATATGT CACAGACAAA        4107

TGCTCTTCTG TAGAGTGACC CTTGGGAAAT CCTTTCTGCA GTTAGCACC ATGAAAATGG         4167

CCCACGCGCC TCCAGGGCAC CACTCAGTCA TTGGTAGACC GAGCGTCAAT GGGCTGGCAT        4227

ATGCTGAATA TGTCATCTAC AGAGGAGAAC AGGCATACCC AGAGTATCTT ATCACTTACC        4287

AGATCATGAA GCCAGAAGCC CCTTCCCAGA CCGCAACAGC CGCAGAGCAG AAGACCTAGT        4347

GAATGCCTGC TGGTGAAGGC CAGATCAGAT TTCAACCTGG GACTGGATTA CAGAGGATTG        4407

TTTCTAATAA CAACATCAAT ATTCTAGAAG TCCCTGACAG CCTAGAAATA AGCTGTTTGT        4467

CTTCTATAAA GCATTGCTAT AGTG                                              4491
```

(2) INFORMATION FOR SEQ ID NO: 8:

(i) SEQUENCE CHARACTERISTICS:
        (A) LENGTH: 673 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Ala Ala Ser Arg Arg Ser Gln His His His His His Gln Gln
  1               5                  10                  15

Gln Leu Gln Pro Ala Pro Gly Ala Ser Ala Pro Pro Pro Pro Pro
                 20                  25                  30

Pro Pro Leu Ser Pro Gly Leu Ala Pro Gly Thr Thr Pro Ala Ser Pro
             35                  40                  45

Thr Ala Ser Gly Leu Ala Pro Phe Ala Ser Pro Arg His Gly Leu Ala
     50                  55                  60

Leu Pro Glu Gly Asp Gly Ser Arg Asp Pro Pro Asp Arg Pro Arg Ser
 65                  70                  75                  80

Pro Asp Pro Val Asp Gly Thr Ser Cys Cys Ser Thr Thr Ser Thr Ile
                 85                  90                  95

Cys Thr Val Ala Ala Ala Pro Val Val Pro Ala Val Ser Thr Ser Ser
                100                 105                 110

Ala Ala Gly Val Ala Pro Asn Pro Ala Gly Ser Gly Ser Asn Asn Ser
            115                 120                 125

Pro Ser Ser Ser Ser Pro Thr Ser Ser Ser Ser Ser Pro Ser
        130                 135                 140

Ser Pro Gly Ser Ser Leu Ala Glu Ser Pro Glu Ala Ala Gly Val Ser
145                 150                 155                 160

Ser Thr Ala Pro Leu Gly Pro Gly Ala Ala Gly Pro Gly Thr Gly Val
                165                 170                 175
```

-continued

```
Pro Ala Val Ser Gly Ala Leu Arg Glu Leu Leu Glu Ala Cys Arg Asn
            180                 185                 190
Gly Asp Val Ser Arg Val Lys Arg Leu Val Asp Ala Ala Asn Val Asn
            195                 200                 205
Ala Lys Asp Met Ala Gly Arg Lys Ser Ser Pro Leu His Phe Ala Ala
            210                 215                 220
Gly Phe Gly Arg Lys Asp Val Val Glu His Leu Leu Gln Met Gly Ala
225                 230                 235                 240
Asn Val His Ala Arg Asp Asp Gly Gly Leu Ile Pro Leu His Asn Ala
                245                 250                 255
Cys Ser Phe Gly His Ala Glu Val Val Ser Leu Leu Leu Cys Gln Gly
            260                 265                 270
Ala Asp Pro Asn Ala Arg Asp Asn Trp Asn Tyr Thr Pro Leu His Glu
            275                 280                 285
Ala Ala Ile Lys Gly Lys Ile Asp Val Cys Ile Val Leu Leu Gln His
            290                 295                 300
Gly Ala Asp Pro Asn Ile Arg Asn Thr Asp Gly Lys Ser Ala Leu Asp
305                 310                 315                 320
Leu Ala Asp Pro Ser Ala Lys Ala Val Leu Thr Gly Glu Tyr Lys Lys
                325                 330                 335
Asp Glu Leu Leu Glu Ala Ala Arg Ser Gly Asn Glu Glu Lys Leu Met
            340                 345                 350
Ala Leu Leu Thr Pro Leu Asn Val Asn Cys His Ala Ser Asp Gly Arg
            355                 360                 365
Lys Ser Thr Pro Leu His Leu Ala Ala Gly Tyr Asn Arg Val Arg Ile
            370                 375                 380
Val Gln Leu Leu Leu Gln His Gly Ala Asp Val His Ala Lys Asp Lys
385                 390                 395                 400
Gly Gly Leu Val Pro Leu His Asn Ala Cys Ser Tyr Gly His Tyr Glu
                405                 410                 415
Val Thr Glu Leu Leu Leu Lys His Gly Ala Cys Val Asn Ala Met Asp
            420                 425                 430
Leu Trp Gln Phe Thr Pro Leu His Glu Ala Ala Ser Lys Asn Arg Val
            435                 440                 445
Glu Val Cys Ser Leu Leu Leu Ser His Gly Ala Asp Pro Thr Leu Val
            450                 455                 460
Asn Cys His Gly Lys Ser Ala Val Asp Met Ala Pro Thr Pro Glu Leu
465                 470                 475                 480
Arg Glu Arg Leu Thr Tyr Glu Phe Lys Gly His Ser Leu Leu Gln Ala
                485                 490                 495
Ala Arg Glu Ala Asp Leu Ala Lys Val Lys Lys Thr Leu Ala Leu Glu
            500                 505                 510
Ile Ile Asn Phe Lys Gln Pro Gln Ser His Glu Thr Ala Leu His Cys
            515                 520                 525
Ala Val Ala Ser Leu His Pro Lys Arg Lys Gln Val Thr Glu Leu Leu
            530                 535                 540
Leu Arg Lys Gly Ala Asn Val Asn Glu Lys Asn Lys Asp Phe Met Thr
545                 550                 555                 560
Pro Leu His Val Ala Ala Glu Arg Ala His Asn Asp Val Met Glu Val
                565                 570                 575
Leu His Lys His Gly Ala Lys Met Asn Ala Leu Asp Thr Leu Gly Gln
            580                 585                 590
```

```
Thr Ala Leu His Arg Ala Ala Leu Ala Gly His Leu Gln Thr Cys Arg
        595                 600                 605

Leu Leu Leu Ser Tyr Gly Ser Asp Pro Ser Ile Ile Ser Leu Gln Gly
        610                 615                 620

Phe Thr Ala Ala Gln Met Gly Asn Glu Ala Val Gln Gln Ile Leu Ser
625                 630                 635                 640

Val Ser Tyr Gly Ser Asp Pro Ser Ile Ile Ser Leu Gln Gly Phe Thr
                645                 650                 655

Ala Ala Gln Met Gly Asn Glu Ala Val Gln Gln Ile Leu Ser Gly His
                660                 665                 670

Ser
```

(2) INFORMATION FOR SEQ ID NO: 9:

(i) SEQUENCE CHARACTERISTICS:
        (A) LENGTH: 4657 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 6..2855

(xi) SEQUENCE DESCRIPTION: SEQ ID NO: 9:

```
CGAAG ATG GCG GCG TCG CGT CGC TCT CAG CAT CAT CAC CAC CAT CAT         47
      Met Ala Ala Ser Arg Arg Ser Gln His His His His His His
      1               5                   10

CAA CAA CAG CTC CAG CCC GCC CCA GGG GCT TCA GCG CCG CCG CCG CCA        95
Gln Gln Gln Leu Gln Pro Ala Pro Gly Ala Ser Ala Pro Pro Pro Pro
15                  20                  25                  30

CCT CCT CCC CCA CTC AGC CCT GGC CTG GCC CCG GGG ACC ACC CCA GCC       143
Pro Pro Pro Pro Leu Ser Pro Gly Leu Ala Pro Gly Thr Thr Pro Ala
                35                  40                  45

TCT CCC ACG GCC AGC GGC CTG GCC CCC TTC GCC TCC CCG CGG CAC GGC       191
Ser Pro Thr Ala Ser Gly Leu Ala Pro Phe Ala Ser Pro Arg His Gly
            50                  55                  60

CTA GCG CTG CCG GAG GGG GAT GGC AGT CGG GAT CCG CCC GAC AGG CCC       239
Leu Ala Leu Pro Glu Gly Asp Gly Ser Arg Asp Pro Pro Asp Arg Pro
        65                  70                  75

CGA TCC CCG GAC CCG GTT GAC GGT ACC AGC TGT TGC AGT ACC ACC AGC       287
Arg Ser Pro Asp Pro Val Asp Gly Thr Ser Cys Cys Ser Thr Thr Ser
    80                  85                  90

ACA ATC TGT ACC GTC GCC GCC GCT CCC GTG GTC CCA GCG GTT TCT ACT       335
Thr Ile Cys Thr Val Ala Ala Ala Pro Val Val Pro Ala Val Ser Thr
95                  100                 105                 110

TCA TCT GCC GCT GGG GTC GCT CCC AAC CCA GCC GGC AGT GGC AGT AAC       383
Ser Ser Ala Ala Gly Val Ala Pro Asn Pro Ala Gly Ser Gly Ser Asn
                115                 120                 125

AAT TCA CCG TCG TCC TCT TCT TCC CCG ACT TCT TCC TCA TCT TCC TCT       431
Asn Ser Pro Ser Ser Ser Ser Ser Pro Thr Ser Ser Ser Ser Ser Ser
            130                 135                 140

CCA TCC TCC CCT GGA TCG AGC TTG GCG GAG AGC CCC GAG GCG GCC GGA       479
Pro Ser Ser Pro Gly Ser Ser Leu Ala Glu Ser Pro Glu Ala Ala Gly
        145                 150                 155

GTT AGC AGC ACA GCA CCA CTG GGG CCT GGG GCA GCA GGA CCT GGG ACA       527
Val Ser Ser Thr Ala Pro Leu Gly Pro Gly Ala Ala Gly Pro Gly Thr
    160                 165                 170
```

```
GGG GTC CCA GCA GTG AGC GGG GCC CTA CGG GAA CTG CTG GAG GCC TGT      575
Gly Val Pro Ala Val Ser Gly Ala Leu Arg Glu Leu Leu Glu Ala Cys
175             180                 185                 190

CGC AAT GGG GAC GTG TCC CGG GTA AAG AGG CTG GTG GAC GCG GCA AAC      623
Arg Asn Gly Asp Val Ser Arg Val Lys Arg Leu Val Asp Ala Ala Asn
                195                 200                 205

GTA AAT GCA AAG GAC ATG GCC GGC CGG AAG TCT TCT CCC CTG CAC TTC      671
Val Asn Ala Lys Asp Met Ala Gly Arg Lys Ser Ser Pro Leu His Phe
        210                 215                 220

GCT GCA GGT TTT GGA AGG AAG GAT GTT GTA GAA CAC TTA CTA CAG ATG      719
Ala Ala Gly Phe Gly Arg Lys Asp Val Val Glu His Leu Leu Gln Met
            225                 230                 235

GGT GCT AAT GTC CAC GCT CGT GAT GAT GGA GGT CTC ATC CCG CTT CAT      767
Gly Ala Asn Val His Ala Arg Asp Asp Gly Gly Leu Ile Pro Leu His
240                 245                 250

AAT GCC TGT TCT TTT GGC CAT GCT GAG GTT GTG AGT CTG TTA TTG TGC      815
Asn Ala Cys Ser Phe Gly His Ala Glu Val Val Ser Leu Leu Leu Cys
255                 260                 265                 270

CAA GGA GCT GAT CCA AAT GCC AGG GAT AAC TGG AAC TAT ACA CCT CTG      863
Gln Gly Ala Asp Pro Asn Ala Arg Asp Asn Trp Asn Tyr Thr Pro Leu
                275                 280                 285

CAT GAA GCT GCT ATT AAA GGG AAG ATC GAT GTG TGC ATT GTG CTG CTG      911
His Glu Ala Ala Ile Lys Gly Lys Ile Asp Val Cys Ile Val Leu Leu
            290                 295                 300

CAG CAC GGA GCT GAC CCA AAC ATT CGG AAC ACT GAT GGG AAA TCA GCC      959
Gln His Gly Ala Asp Pro Asn Ile Arg Asn Thr Asp Gly Lys Ser Ala
        305                 310                 315

CTG GAC CTG GCA GAT CCT TCA GCA AAA GCT GTC CTT ACA GGT GAA TAC     1007
Leu Asp Leu Ala Asp Pro Ser Ala Lys Ala Val Leu Thr Gly Glu Tyr
320                 325                 330

AAG AAA GAC GAA CTC CTA GAA GCT GCT AGG AGT GGT AAT GAA GAA AAA     1055
Lys Lys Asp Glu Leu Leu Glu Ala Ala Arg Ser Gly Asn Glu Glu Lys
335                 340                 345                 350

CTA ATG GCT TTA CTG ACT CCT CTA AAT GTG AAT TGC CAT GCA AGT GAT     1103
Leu Met Ala Leu Leu Thr Pro Leu Asn Val Asn Cys His Ala Ser Asp
                355                 360                 365

GGG CGA AAG TCG ACT CCT TTA CAT CTA GCA GCG GGC TAC AAC AGA GTT     1151
Gly Arg Lys Ser Thr Pro Leu His Leu Ala Ala Gly Tyr Asn Arg Val
            370                 375                 380

CGA ATA GTT CAG CTT CTT CTT CAG CAT GGT GCT GAT GTT CAT GCA AAA     1199
Arg Ile Val Gln Leu Leu Leu Gln His Gly Ala Asp Val His Ala Lys
        385                 390                 395

GAC AAA GGT GGA CTT GTG CCT CTT CAT AAT GCA TGT TCA TAT GGA CAT     1247
Asp Lys Gly Gly Leu Val Pro Leu His Asn Ala Cys Ser Tyr Gly His
400                 405                 410

TAT GAA GTC ACA GAA CTG CTA CTA AAG CAT GGA GCT TGT GTT AAT GCC     1295
Tyr Glu Val Thr Glu Leu Leu Leu Lys His Gly Ala Cys Val Asn Ala
415                 420                 425                 430

ATG GAT CTC TGG CAG TTT ACT CCA CTG CAC GAG GCT GCT TCC AAG AAC     1343
Met Asp Leu Trp Gln Phe Thr Pro Leu His Glu Ala Ala Ser Lys Asn
                435                 440                 445

CGT GTA GAA GTC TGC TCT TTG TTA CTT AGC CAT GGC GCT GAT CCT ACG     1391
Arg Val Glu Val Cys Ser Leu Leu Leu Ser His Gly Ala Asp Pro Thr
            450                 455                 460

TTA GTC AAC TGC CAT GGC AAA AGT GCT GTG GAT ATG GCT CCA ACT CCG     1439
Leu Val Asn Cys His Gly Lys Ser Ala Val Asp Met Ala Pro Thr Pro
        465                 470                 475

GAG CTT AGG GAG AGA TTG ACT TAT GAA TTT AAA GGT CAT TCT TTA CTA     1487
Glu Leu Arg Glu Arg Leu Thr Tyr Glu Phe Lys Gly His Ser Leu Leu
```

```
                    480                 485                 490
CAA GCA GCC AGA GAA GCA GAC TTA GCT AAA GTT AAA AAA ACA CTC GCT    1535
Gln Ala Ala Arg Glu Ala Asp Leu Ala Lys Val Lys Lys Thr Leu Ala
495             500                 505                 510

CTG GAA ATC ATT AAT TTC AAA CAA CCG CAG TCT CAT GAA ACA GCA CTG    1583
Leu Glu Ile Ile Asn Phe Lys Gln Pro Gln Ser His Glu Thr Ala Leu
                515                 520                 525

CAC TGT GCT GTG GCC TCT CTG CAT CCC AAA CGT AAA CAA GTG ACA GAA    1631
His Cys Ala Val Ala Ser Leu His Pro Lys Arg Lys Gln Val Thr Glu
            530                 535                 540

TTG TTA CTT AGA AAA GGA GCA AAT GTT AAT GAA AAA AAT AAA GAT TTC    1679
Leu Leu Leu Arg Lys Gly Ala Asn Val Asn Glu Lys Asn Lys Asp Phe
        545                 550                 555

ATG ACT CCC CTG CAT GTT GCA GCC GAA AGA GCC CAT AAT GAT GTC ATG    1727
Met Thr Pro Leu His Val Ala Ala Glu Arg Ala His Asn Asp Val Met
    560                 565                 570

GAA GTT CTG CAT AAG CAT GGC GCC AAG ATG AAT GCA CTG GAC ACC CTT    1775
Glu Val Leu His Lys His Gly Ala Lys Met Asn Ala Leu Asp Thr Leu
575             580                 585                 590

GGT CAG ACT GCT TTG CAT AGA GCC GCC CTA GCA GGC CAC CTG CAG ACC    1823
Gly Gln Thr Ala Leu His Arg Ala Ala Leu Ala Gly His Leu Gln Thr
                595                 600                 605

TGC CGC CTC CTG CTG AGT TAC GGC TCT GAC CCC TCC ATC ATC TCC TTA    1871
Cys Arg Leu Leu Leu Ser Tyr Gly Ser Asp Pro Ser Ile Ile Ser Leu
            610                 615                 620

CAA GGC TTC ACA GCA GCA CAG ATG GGC AAT GAA GCA GTG CAG CAG ATT    1919
Gln Gly Phe Thr Ala Ala Gln Met Gly Asn Glu Ala Val Gln Gln Ile
        625                 630                 635

CTG AGT GAG AGT ACA CCT ATA CGT ACT TCT GAT GTT GAT TAT CGA CTC    1967
Leu Ser Glu Ser Thr Pro Ile Arg Thr Ser Asp Val Asp Tyr Arg Leu
    640                 645                 650

TTA GAG GCA TCT AAA GCT GGA GAC TTG GAA ACT GTG AAG CAA CTT TGC    2015
Leu Glu Ala Ser Lys Ala Gly Asp Leu Glu Thr Val Lys Gln Leu Cys
655             660                 665                 670

AGC TCT CAA AAT GTG AAT TGT AGA GAC TTA GAG GGC CGG CAT TCC ACG    2063
Ser Ser Gln Asn Val Asn Cys Arg Asp Leu Glu Gly Arg His Ser Thr
                675                 680                 685

CCC TTA CAC TTC GCA GCA GGC TAC AAC CGC GTG TCT GTT GTA GAG TAC    2111
Pro Leu His Phe Ala Ala Gly Tyr Asn Arg Val Ser Val Val Glu Tyr
            690                 695                 700

CTG CTA CAC CAC GGT GCC GAT GTC CAT GCC AAA GAC AAG GGT GGC TTG    2159
Leu Leu His His Gly Ala Asp Val His Ala Lys Asp Lys Gly Gly Leu
        705                 710                 715

GTG CCC CTT CAT AAT GCC TGT TCA TAT GGA CAC TAT GAG GTG GCT GAG    2207
Val Pro Leu His Asn Ala Cys Ser Tyr Gly His Tyr Glu Val Ala Glu
    720                 725                 730

CTT TTA GTA AGG CAT GGG GCT TCT GTC AAT GTG GCG GAC TTA TGG AAA    2255
Leu Leu Val Arg His Gly Ala Ser Val Asn Val Ala Asp Leu Trp Lys
735             740                 745                 750

TTT ACC CCT CTC CAT GAA GCA GCA GCT AAA GGA AAG TAT GAA ATC TGC    2303
Phe Thr Pro Leu His Glu Ala Ala Ala Lys Gly Lys Tyr Glu Ile Cys
                755                 760                 765

AAG CTC CTT TTA AAA CAT GGA GCA GAT CCA ACT AAA AAG AAC AGA GAT    2351
Lys Leu Leu Leu Lys His Gly Ala Asp Pro Thr Lys Lys Asn Arg Asp
            770                 775                 780

GGA AAT ACA CCT TTG GAT TTG GTA AAG GAA GGA GAC ACA GAT ATT CAG    2399
Gly Asn Thr Pro Leu Asp Leu Val Lys Glu Gly Asp Thr Asp Ile Gln
        785                 790                 795

GAC TTA CTG AAA GGG GAT GCT GCT TTG TTG GAT GCT GCC AAG AAG GGC    2447
```

```
                Asp Leu Leu Lys Gly Asp Ala Ala Leu Leu Asp Ala Ala Lys Lys Gly
                    800                 805                 810

TGC CTG GCA AGA GTG CAG AAG CTC TGT ACC CCA GAG AAT ATC AAC TGC            2495
Cys Leu Ala Arg Val Gln Lys Leu Cys Thr Pro Glu Asn Ile Asn Cys
815                 820                 825                 830

AGA GAC ACC CAG GGC AGA AAT TCA ACC CCT CTG CAC CTG GCA GCA GGC            2543
Arg Asp Thr Gln Gly Arg Asn Ser Thr Pro Leu His Leu Ala Ala Gly
                835                 840                 845

TAT AAT AAC CTG GAA GTA GCT GAA TAT CTT CTA GAG CAT GGA GCT GAT            2591
Tyr Asn Asn Leu Glu Val Ala Glu Tyr Leu Leu Glu His Gly Ala Asp
            850                 855                 860

GTT AAT GCC CAG GAC AAG GGT GGT TTA ATT CCT CTT CAT AAT GCG GCA            2639
Val Asn Ala Gln Asp Lys Gly Gly Leu Ile Pro Leu His Asn Ala Ala
        865                 870                 875

TCT TAT GGG GGC TGC CTG GCA AGA GTG CAG AAG CTC TGT ACC CCA GAG            2687
Ser Tyr Gly Gly Cys Leu Ala Arg Val Gln Lys Leu Cys Thr Pro Glu
    880                 885                 890

AAT ATC AAC TGC AGA GAC ACC CAG GGC AGA AAT TCA ACC CCT CTG CAC            2735
Asn Ile Asn Cys Arg Asp Thr Gln Gly Arg Asn Ser Thr Pro Leu His
895                 900                 905                 910

CTG GCA GCA GGC TAT AAT AAC CTG GAA GTA GCT GAA TAT CTT CTA GAG            2783
Leu Ala Ala Gly Tyr Asn Asn Leu Glu Val Ala Glu Tyr Leu Leu Glu
                915                 920                 925

CAT GGA GCT GAT GTT AAT GCC CAG GAC AAG GGT GGT TTA ATT CCT CTT            2831
His Gly Ala Asp Val Asn Ala Gln Asp Lys Gly Gly Leu Ile Pro Leu
            930                 935                 940

CAT AAT GCG GCA TCT TAT GGG TAG TAAAAGTTGG ATTCCAAGAC CTCCTTTCCA           2885
His Asn Ala Ala Ser Tyr Gly  *
        945                 950

GCTTGTTGTA ATGATTAAAT GAGACCATGC ATGTGGAAAT TGCATTAACT AATGTAAGGC          2945

ATTATAAAAA TGCAAGCATG TTGACATAGC GGCTTTATTG ATAAAATACA ACACGTGTGT          3005

AAATGCAACA GATAAGTGGG CGTTTACTCC CCTCCATGAA GCAGCCCAGA AGGAAGGAC           3065

GCAGCTGTGC GCCCTCCTCC TAGCGCATGG TGCAGACCCC ACCATGAAGA ACCAGGAAGG          3125

CCAGACGCCT CTGGATCTGG CAACAGCTGA CGATATCAGA GCTTTGCATG TTGACATAGC          3185

GGCTTTATTG ATAAAATACA ACACGTGTGT AAATGCAACA GATAAGTGGG CGTTTACTCC          3245

CCTCCATGAA GCAGCCCAGA AGGAAGGAC GCAGCTGTGC GCCCTCCTCC TAGCGCATGG           3305

TGCAGACCCC ACCATGAAGA ACCAGGAAGG CCAGACGCCT CTGGATCTGG CAACAGCTGA          3365

CGATATCAGA GCTTTGCTGA TAGATGCCAT GCCCCCAGAG GCCTTACCTA CCTGTTTTAA          3425

ACCTCAGGCT ACTGTAGTGA GTGCCTCTCT GATCTCACCA GCATCCACCC CCTCCTGCCT          3485

CTCGGCTGCC AGCAGCATAG ACAACCTCAC TGGCCCTTTA GCAGAGTTGG CCGTAGGAGG          3545

AGCCTCCAAT GCAGGGGATG CGCCGCGGG AACAGAAAGG AAGGAAGGAG AAGTTGCTGG          3605

TCTTGACATG AATATCAGCC AATTTCTAAA AGCCTTGGC CTTGAACACC TTCGGGATAT          3665

CTTTGAAACA GAACAGATTA CACTAGATGT GTTGGCTGAT ATGGGTCATG AAGAGTTGAA          3725

AGAAATAGGC ATCAATGCAT ATGGGCACCG CCACAAATTA ATCAAAGGAG TAGAAAGACT          3785

CTTAGGTGGA CAACAAGGCA CCAATCCTTA TTTGACTTTT CACTGTGTTA ATCAGGGAAC          3845

GATTTTGCTG GATCTTGCTC CAGAAGATAA AGAATATCAG TCAGTGGAAG AAGAGATGCA          3905

AAGTACTATT CGAGAACACA GAGATGGTGG TAATGCTGGC GGCATCTTCA ACAGATACAA          3965

TGTCATTCGA ATTCAAAAAG TTGTCAACAA GAAGTTGAGG GAGCGGTTCT GCCACCGACA          4025

GAAGGAAGTG TCTGAGGAGA ATCACAACCA TCACAATGAG CGCATGTTGT TTCATGGTTC          4085
```

```
TCCTTTCATT AATGCCATTA TTCATAAAGG GTTTGATGAG CGACATGCAT ACATAGGAGG      4145

AATGTTTGGG GCCGGGATTT ATTTTGCTGA AAACTCCTCA AAAAGCAACC AATATGTTTA      4205

TGGAATTGGA GGAGGAACAG GCTGCCCTAC ACACAAGGAC AGGTCATGCT ATATATGTCA      4265

CAGACAAATG CTCTTCTGTA GAGTGACCCT TGGGAAATCC TTTCTGCAGT TTAGCACCAT      4325

GAAAATGGCC CACGCGCCTC CAGGGCACCA CTCAGTCATT GGTAGACCGA GCGTCAATGG      4385

GCTGGCATAT GCTGAATATG TCATCTACAG AGGAGAACAG GCATACCCAG AGTATCTTAT      4445

CACTTACCAG ATCATGAAGC CAGAAGCCCC TTCCCAGACC GCAACAGCCG CAGAGCAGAA      4505

GACCTAGTGA ATGCCTGCTG GTGAAGGCCA GATCAGATTT CAACCTGGGA CTGGATTACA      4565

GAGGATTGTT TCTAATAACA ACATCAATAT TCTAGAAGTC CCTGACAGCC TAGAAATAAG      4625

CTGTTTGTCT TCTATAAAGC ATTGCTATAG TG                                   4657
```

(2) INFORMATION FOR SEQ ID NO: 10:

(i) SEQUENCE CHARACTERISTICS:
        (A) LENGTH: 949 amino acids
        (B) TYPE: amino acid
        (D) TOPOLOGY: linear (ii) MOLECULE TYPE: protein (xi) SEQUENCE DESCRIPTION: SEQ ID NO: 10:

```
Met Ala Ala Ser Arg Arg Ser Gln His His His His His Gln Gln
 1               5                  10                  15

Gln Leu Gln Pro Ala Pro Gly Ala Ser Ala Pro Pro Pro Pro Pro
                20                  25                  30

Pro Pro Leu Ser Pro Gly Leu Ala Pro Gly Thr Thr Pro Ala Ser Pro
         35                  40                  45

Thr Ala Ser Gly Leu Ala Pro Phe Ala Ser Pro Arg His Gly Leu Ala
         50                  55                  60

Leu Pro Glu Gly Asp Gly Ser Arg Asp Pro Pro Asp Arg Pro Arg Ser
65                  70                  75                  80

Pro Asp Pro Val Asp Gly Thr Ser Cys Cys Ser Thr Thr Ser Thr Ile
                85                  90                  95

Cys Thr Val Ala Ala Ala Pro Val Val Pro Ala Val Ser Thr Ser Ser
                100                 105                 110

Ala Ala Gly Val Ala Pro Asn Pro Ala Gly Ser Gly Ser Asn Asn Ser
            115                 120                 125

Pro Ser Ser Ser Ser Pro Thr Ser Ser Ser Ser Ser Pro Ser
130                 135                 140

Ser Pro Gly Ser Ser Leu Ala Glu Ser Pro Glu Ala Ala Gly Val Ser
145                 150                 155                 160

Ser Thr Ala Pro Leu Gly Pro Gly Ala Ala Gly Pro Gly Thr Gly Val
                165                 170                 175

Pro Ala Val Ser Gly Ala Leu Arg Glu Leu Leu Glu Ala Cys Arg Asn
                180                 185                 190

Gly Asp Val Ser Arg Val Lys Arg Leu Val Asp Ala Ala Asn Val Asn
            195                 200                 205

Ala Lys Asp Met Ala Gly Arg Lys Ser Ser Pro Leu His Phe Ala Ala
    210                 215                 220

Gly Phe Gly Arg Lys Asp Val Val Glu His Leu Leu Gln Met Gly Ala
225                 230                 235                 240

Asn Val His Ala Arg Asp Asp Gly Gly Leu Ile Pro Leu His Asn Ala
                245                 250                 255
```

-continued

```
Cys Ser Phe Gly His Ala Glu Val Val Ser Leu Leu Leu Cys Gln Gly
            260                 265                 270

Ala Asp Pro Asn Ala Arg Asp Asn Trp Asn Tyr Thr Pro Leu His Glu
            275                 280                 285

Ala Ala Ile Lys Gly Lys Ile Asp Val Cys Ile Val Leu Leu Gln His
            290                 295                 300

Gly Ala Asp Pro Asn Ile Arg Asn Thr Asp Gly Lys Ser Ala Leu Asp
305                 310                 315                 320

Leu Ala Asp Pro Ser Ala Lys Ala Val Leu Thr Gly Glu Tyr Lys Lys
                    325                 330                 335

Asp Glu Leu Leu Glu Ala Ala Arg Ser Gly Asn Glu Glu Lys Leu Met
                340                 345                 350

Ala Leu Leu Thr Pro Leu Asn Val Asn Cys His Ala Ser Asp Gly Arg
            355                 360                 365

Lys Ser Thr Pro Leu His Leu Ala Ala Gly Tyr Asn Arg Val Arg Ile
            370                 375                 380

Val Gln Leu Leu Leu Gln His Gly Ala Asp Val His Ala Lys Asp Lys
385                 390                 395                 400

Gly Gly Leu Val Pro Leu His Asn Ala Cys Ser Tyr Gly His Tyr Glu
                    405                 410                 415

Val Thr Glu Leu Leu Lys His Gly Ala Cys Val Asn Ala Met Asp
                420                 425                 430

Leu Trp Gln Phe Thr Pro Leu His Glu Ala Ala Ser Lys Asn Arg Val
            435                 440                 445

Glu Val Cys Ser Leu Leu Leu Ser His Gly Ala Asp Pro Thr Leu Val
            450                 455                 460

Asn Cys His Gly Lys Ser Ala Val Asp Met Ala Pro Thr Pro Glu Leu
465                 470                 475                 480

Arg Glu Arg Leu Thr Tyr Glu Phe Lys Gly His Ser Leu Leu Gln Ala
                    485                 490                 495

Ala Arg Glu Ala Asp Leu Ala Lys Val Lys Lys Thr Leu Ala Leu Glu
                500                 505                 510

Ile Ile Asn Phe Lys Gln Pro Gln Ser His Glu Thr Ala Leu His Cys
            515                 520                 525

Ala Val Ala Ser Leu His Pro Lys Arg Lys Gln Val Thr Glu Leu Leu
            530                 535                 540

Leu Arg Lys Gly Ala Asn Val Asn Glu Lys Asn Lys Asp Phe Met Thr
545                 550                 555                 560

Pro Leu His Val Ala Ala Glu Arg Ala His Asn Asp Val Met Glu Val
                    565                 570                 575

Leu His Lys His Gly Ala Lys Met Asn Ala Leu Asp Thr Leu Gly Gln
                580                 585                 590

Thr Ala Leu His Arg Ala Ala Leu Ala Gly His Leu Gln Thr Cys Arg
            595                 600                 605

Leu Leu Leu Ser Tyr Gly Ser Asp Pro Ser Ile Ile Ser Leu Gln Gly
            610                 615                 620

Phe Thr Ala Ala Gln Met Gly Asn Glu Ala Val Gln Gln Ile Leu Ser
625                 630                 635                 640

Glu Ser Thr Pro Ile Arg Thr Ser Asp Val Asp Tyr Arg Leu Leu Glu
                    645                 650                 655

Ala Ser Lys Ala Gly Asp Leu Glu Thr Val Lys Gln Leu Cys Ser Ser
                660                 665                 670
```

```
Gln Asn Val Asn Cys Arg Asp Leu Glu Gly Arg His Ser Thr Pro Leu
            675                 680                 685
His Phe Ala Ala Gly Tyr Asn Arg Val Ser Val Glu Tyr Leu Leu
        690                 695                 700
His His Gly Ala Asp Val His Ala Lys Asp Lys Gly Gly Leu Val Pro
705                 710                 715                 720
Leu His Asn Ala Cys Ser Tyr Gly His Tyr Glu Val Ala Glu Leu Leu
            725                 730                 735
Val Arg His Gly Ala Ser Val Asn Val Ala Asp Leu Trp Lys Phe Thr
            740                 745                 750
Pro Leu His Glu Ala Ala Lys Gly Lys Tyr Glu Ile Cys Lys Leu
            755                 760                 765
Leu Leu Lys His Gly Ala Asp Pro Thr Lys Lys Asn Arg Asp Gly Asn
            770                 775                 780
Thr Pro Leu Asp Leu Val Lys Glu Gly Asp Thr Asp Ile Gln Asp Leu
785                 790                 795                 800
Leu Lys Gly Asp Ala Ala Leu Leu Asp Ala Ala Lys Lys Gly Cys Leu
            805                 810                 815
Ala Arg Val Gln Lys Leu Cys Thr Pro Glu Asn Ile Asn Cys Arg Asp
            820                 825                 830
Thr Gln Gly Arg Asn Ser Thr Pro Leu His Leu Ala Ala Gly Tyr Asn
            835                 840                 845
Asn Leu Glu Val Ala Glu Tyr Leu Leu Glu His Gly Ala Asp Val Asn
            850                 855                 860
Ala Gln Asp Lys Gly Gly Leu Ile Pro Leu His Asn Ala Ala Ser Tyr
865                 870                 875                 880
Gly Gly Cys Leu Ala Arg Val Gln Lys Leu Cys Thr Pro Glu Asn Ile
            885                 890                 895
Asn Cys Arg Asp Thr Gln Gly Arg Asn Ser Thr Pro Leu His Leu Ala
            900                 905                 910
Ala Gly Tyr Asn Asn Leu Glu Val Ala Glu Tyr Leu Leu Glu His Gly
            915                 920                 925
Ala Asp Val Asn Ala Gln Asp Lys Gly Gly Leu Ile Pro Leu His Asn
        930                 935                 940
Ala Ala Ser Tyr Gly
945             950
```

(2) INFORMATION FOR SEQ ID NO: 11:

(i) SEQUENCE CHARACTERISTICS:
        (A) LENGTH: 357 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (xi) SEQUENCE DESCRIPTION: SEQ ID NO: 11:

```
TGAGTTACGG CTCTGACCCC TCCATCATCT CCTTACAAGG CTTCACAGCA GCACAGATGG      60

GCAATGAAGC AGTGCAGCAG ATTCTGAGTG GTCATTCGTA GATAGTGATC ATTCTACTTC     120

AGCCTTAATG GTGATCTTGA GACGGGAAGA TTTAGAAGGA AATCTATCCA GCATGTCTTC     180

ACTGTCAACA TGAAGAGTAC ACCTATACGT ACTTCTGATG TTGATTATCG ACTCTTAGAG     240

GCATCTAAAG CTGGAGACTT GGAAACTGTG AAGCAACTTT GCAGCTCTCA AAATGTGAAT     300
```

-continued

```
TGTAGAGACT TAGAGGGCCG GCATTCCACG CCCTTACACT TCGCAGCAGG CTACAAC        357

(2) INFORMATION FOR SEQ ID NO: 12:

(i) SEQUENCE CHARACTERISTICS:
        (A) LENGTH: 523 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (xi) SEQUENCE DESCRIPTION: SEQ ID NO: 12:

GGCTGCCTGG CAAGAGTGCA GAAGCTCTGT ACCCCAGAGA ATATCAACTG CAGAGACACC         60

CAGGGCAGAA ATTCAACCCC TCTGCACCTG GCAGCAGGCT ATAATAACCT GGAAGTAGCT        120

GAATATCTTC TAGAGCATGG AGCTGATGTT AATGCCCAGG ACAAGGGTGG TTTAATTCCT        180

CTTCATAATG CGGCATCTTA TGGGTAGTAA AAGTTGGATT CCAAGACCTC CTTTCCAGCT        240

TGTTGTAATG ATTAAATGAG ACCATGCATG TGGAAATTGC ATTAACTAAT GTAAGGCATT        300

ATAAAAATGC AAGCATGTTG ACATAGCGGC TTTATTGATA AAATACAACA CGTGTGTAAA        360

TGCAACAGAT AAGTGGGCGT TTACTCCCCT CCATGAAGCA GCCCAGAAAG GAAGGACGCA        420

GCTGTGCGCC CTCCTCCTAG CGCATGGTGC AGACCCCACC ATGAAGAACC AGGAAGGCCA        480

GACGCCTCTG GATCTGGCAA CAGCTGACGA TATCAGAGCT TTG                         523
```

TRF1 BINDING PROTEIN, METHODS OF USE THEREOF

CROSS-REFERENCE TO RELATED APPLICATIONS

The present Application is a Continuation-In-Part of U.S. Ser. No. 09/135,233 filed Aug. 17, 1998, now abandoned, which is a Continuation-In-Part of U.S. Ser. No. 09/095,225 filed Jun. 10, 1998, now abandoned, the disclosures of which are hereby incorporated by reference in their entireties. Applicants claim the benefits of these Application under 35 U.S.C. § 120.

GOVERNMENTAL SUPPORT

The research leading to the present invention was supported, at least in part, by a grant from the National Institutes of Health, Grant No. GM 49046. Accordingly, the Government may have certain rights in the invention.

FIELD OF THE INVENTION

The present invention relates generally to a unique vertebrate protein, tankyrase that binds to telomeric repeat binding factor 1 (TRF1), to the nucleic acids encoding tankyrases, and to therapeutic methods of use thereof. The tankyrases may also have a particular use in developing drugs that can counteract the telomere shortening associated with aging and certain diseases such as ataxia telangiectasia.

BACKGROUND OF THE INVENTION

Telomeres are terminal structural elements found at the end of chromosomes [Muller, *The Collecting Net-Woods Hole*, 13:181–195 (1939)] that protect natural double-stranded DNA ends from degradation, fusion, and recombination with chromosome-internal DNA [McClintock, *Genetics*, 26:234–282 (1941); Lundblad et al., *Cell*, 87:369–375 (1996)]. Telomeres are also thought to play a role in the architecture of the nucleus [Agard et al., *Nature*, 302:676–681 (1983); Rabl, *Morphol. J.*, 10:214–330 (1885)], and to provide a solution to the end-replication problem that arises as a consequence of successive replication of linear DNA by DNA polymerases which would otherwise result with progressively shorter terminal sequences [Watson, *Nature*, 239:197–201 (1972)]. In tetrahymena, impaired telomere function leads to a defect in cytokinesis and to cell death [Yu et al., *Nature*, 344:126–132 (1990)]. Similarly, in yeast, loss of a single telomere results in cell cycle arrest and chromosome instability [Sandell and Zakian, *Cell*, 75:729–741 (1993)] and cells undergoing generalized telomere shortening eventually senesce [Lundblad and Szostak, *Cell*, 57:633–643 (1989); Singer and Gottschling, *Science*, 266:404–409 (1994)].

A ribonucleoprotein reverse transcriptase, telomerase, can elongate telomeres using an internal RNA component as template for the addition of the appropriate G-rich sequence to the 3' telomere termini [Greider and Blackburn, *Cell*, 43:405–413 (1985)]. This activity is thought to compensate for the inability of polymerases to replicate chromosome ends, but other mechanisms of telomere maintenance may operate as well [Pluta et al., *Nature*, 337:429–433 (1989)].

Telomeres contain a tandem array of repeat sequences, typically five to eight base pairs long, that are G-rich in the strand that extends to the end of the chromosome DNA. These repeat units appear to be both necessary and sufficient for telomere function [Lundblad and Szostak, *Cell*, 57:633–643 (1989); Szostak et al., *Cell*, 36:459–568 (1982)]. All telomeres of a single genome are composed of the same repeats and these sequences are highly conserved across species. For instance, Oxytricha chromosomes terminate in TTTTGGGG repeats [Klobutcher et al., *Proc. Natl. Acad. Sci. USA*, 78:3015–3019 (1981)], Tetrahymena utilizes an array of $(TTGGGG)_n$ [Blackburn et al., *J. Mol. Biol.*, 120:33–53 (1978)], and plant chromosomes carry the sequence $(TTTAGGG)_n$ [Richards et al., *Cell*, 53:127–136 (1988)]. Telomeres of trypanosomes and all vertebrates, including mammals, contain the repeat sequence TTAGGG [Blackburn et al., *Cell*, 36:447–458 (1984); Brown, *Nature*, 338:774–776 (1986); Cross et al., *Nature*, 338:771–774 (1989); Moyzis et al., *Proc. Natl. Acad. Sci. USA*, 85:6622–6626 (1988); Van der Ploeg et al., *Cell*, 36:459–468 (1984)]. This 6 basepair sequence is repeated in long tandem arrays at the chromosome ends, which may be as long as 100 kb in the mouse, and varies from 2 to 30 kb in humans [de Lange, Telomere Dynamics and Genome Instability in Human Cancer, In Telomeres, Blackburn and Greider eds., Cold Spring Harbor Press; 265–295 (1995)].

During the development of human somatic tissue, telomeres undergo progressive shortening; in contrast, sperm telomeres increase with donor age [Broccoli et al., *Proc. Natl. Acad. Sci. USA*, 92:9082–9086 (1995); de Lange, *Proc. Natl. Acad. Sci. USA*, 91:2882–2885 (1994)]. Most if not all human somatic tissue chromosomes lose terminal TTAGGG repeats with each division, e.g., about 15–40 basepairs per year in the skin and blood. It is unclear what effect this diminution has since human telomeres are between 6–10 kb at birth. On the other hand, it is not yet known how many kilobases of TTAGGG repeats are necessary for optimal telomere function.

Primary human fibroblasts grown in culture lose about 50 basepairs of telomeric DNA per doubling (PD) before they stop dividing at a senescence stage [Allsopp et al., *Proc. Natl. Acad. Sci. USA*, 89:10114–10118 (1992)]. Importantly, there is an excellent correlation between the number of divisions that the cells go through and their initial telomere length. Indeed, it has been suggested that the correlation represents a molecular clock, which limits the potential of primary cells to replicate [Harley et al., *Nature* (London), 345:458–460 (1990); Harley et al., *Exp. Gerontol*, 27:375–382 (1992)]. Thus, immortalization of human somatic cells involves a mechanism to halt telomere shortening [Bodnar et al., *Science*, 279:349–352 (1998)].

Changes in telomeric dynamics also appear to play a role in the malignant transformation of human cells [Counter et al., *EMBO J.*, 11:1921–1929 (1992); Counter et al., *Proc. Natl. Acad. Sci. USA*, 91:2900–2904 (1994); Kim et al., *Science*, 266:2011–2015 (1994)]. For example, telomeres of tumor cells are generally significantly shorter than those of the corresponding normal cells [de Lange et al., *Mol. Cell Biol.*, 10:518–527 (1990)]. Telomerase activation appears to be an obligatory step in the immortalization of human cells [de Lange, *Proc. Natl. Acad. Sci. USA*, 91:2882–2885 (1994); Counter et al., *EMBO J.*, 11:1921–1929 (1992); Counter et al., *Proc. Natl. Acad. Sci.*, 91:2900–2904 (1994); Kim et al., *Science*, 266:2011–2015 (1994); Bodnar et al., *Science*, 279:349–352 (1998)].

Hanish et al. [*Proc. Natl. Acad. Sci. USA*, 91:8861–8865 (1994)] examined the requirements for the formation of human telomeres from TTAGGG seeds, and found that telomere formation was not correlated with the ability of human telomerase to elongate telomeric sequences in vitro, and did not appear to be a result of homologous recombination. Rather, the sequence dependence of telomere formation matched the in vitro binding requirements for TRF1, a telomeric TTAGGG repeat binding protein that is associated with human and mouse telomeres in interphase and in mitosis.

Indeed, several observations suggest the existence of regulatory mechanisms to control telomere length. Mammalian telomeres show a species-specific length setting [Kipling and Cooke, *Nature*, 347:400–402 (1990)] indicating a mechanism to control telomere length in the germline. Mammalian cells also have a mechanism to measure and regulate the length of individual telomeres. For example, in telomere seed experiments the final length of individual newly-formed telomeres matches the length of the host cell telomeres [Barnett et al., *Nucl. Acids Res.*, 21:27–36 (1993); Hanish et al., *Proc. Natl. Acad. Sci. USA*, 91:8861–8865 (1994)]. Telomere length regulation is also apparent in several human cell lines, which maintain their telomeres at a stable length setting despite high levels of telomerase [Counter et al., *EMBO J.*, 11:1921–1929 (1992)]. Thus, cells can monitor and modulate individual telomeres, a process that is likely to involve proteins bound to the TTAGGG repeats at chromosome ends.

Another process likely to be mediated by TTAGGG binding proteins is the protective cap function of telomeres. Telomeres are protected from the cellular surveillance systems that monitor DNA damage. Thus, cells can distinguish natural chromosome ends (telomeres) from double strand breaks (resulting from DNA damage).

The only known protein components of mammalian telomeres are the TRF proteins, duplex TTAGGG repeat binding factors that are localized at telomeres in interphase and metaphase chromosomes [Zhong et al., *Mol. Cell. Biol.*, 13:4834–4943 (1992); Chong et al., *Science*, 270:1663–1667 (1995); Ludérus et al., *J. Cell Biol.*, 135:867–881 (1996); Broccoli et al., *Hum. Mol. Genetics*, 6:69–76 (1997); see Smith and de Lange, *Trends in Genetics*, 13:21–26 (1997) for review; Broccoli et al., *Nature Gen.*, 17:231–235 (1997); Bilaud et al., *Nature Gen.*, 17:236–239 (1997); van Steensel et al., *Cell*, 92:401–413 (1998)]. Thus far, only two human telomeric DNA binding proteins have been identified, TRF1 and TRF2 [U.S. Pat. No. 5,733,730, Issued Mar. 31, 1998, and U.S. patent application Ser. Nos. 08/938,052, filed Sep. 26, 1997, and 09/018,635 filed Feb. 4, 1998, all of which are whereby incorporated by reference in their entireties]. TRF1 was isolated as a double-stranded TTAGGG-repeat binding protein from HeLa cells [Chong et al., *Science*, 270:1663–1667 (1995)]. This factor contains three recognizable domains: an acidic N-terminal domain, a dimerization domain, and a C-terminal three helix bundle similar to the Myb and homeodomain DNA-binding folds [Bianchi et al., *EMBO J.*, 16:1785–1794 (1997); Chong et al., *Science*, 270:1663–1667 (1995); reviewed in Konig and Rhodes, *Cell*, 85:125–136 (1996); Smith and de Lange, *Trends in Genetics*, 13:21–26 (1997)]. A second factor, TRF2, is related to TRF1 in its dimerization domain and the C-terminal Myb motif, but differs in that its N-terminus is basic rather than acidic [Bilaud et al., *Nature Gen.*, 17:236–239 (1997); Broccoli et al., *Nature Gen.*, 17:231–235 (1997)]. Despite their related dimerization domains, the proteins do not interact with each other [Broccoli, et al., *Nature Gen.*, 17:231–235 (1997)], and probably exist predominantly as homodimers. Both proteins bind specifically to double-stranded TTAGGG repeats in vitro and are located at telomeres in vivo. The two TRFs are ubiquitously expressed and current evidence indicates that most human telomeres contain both factors bound simultaneously throughout the cell cycle [Broccoli et al., *Nature Gen.*, 17:231–235 (1997); Chong et al., *Science*, 270:1663–1667 (1995); Smith and de Lange, *Trends in Genetics*, 13:21–26 (1997)]. Two other double-stranded telomeric-repeat binding proteins have been identified; Rap1p in *S. cerevisia* [Reviewed in Shore, *Trends Gen.*, 10:408–412 (1994) and Taz1p in *S. pombe* [Cooper et al., *Nature*, 385:744–474 (1997)]. Both have Myb type DNA-binding domains [Cooper et al., *Nature*, 385:744–747 (1997); Konig et al., *Cell*, 85:125–136 (1996)]. In addition, Taz1p shows weak overall homology with TFR1 and shares its acidic nature [Cooper et al., *Nature*, 385:744–747 (1997)].

Recent studies have shown that TRF2 plays a key role in the protective activity of telomeres by inhibiting end-to-end fusions [van Steensel et al., *Cell*, 92:401–413 (1998)]. Previous studies had indicated that TRF1 plays a different role in telomere biology, functioning as a negative regulator of telomere length maintenance Ivan Steensel and de Lange, *Nature*, 385:740–743 (1997)]. Thus, long-term overexpression of TRF1 in a telomerase-positive tumor cell line resulted in progressive telomere shortening. Conversely, removal of TRF1 from the telomere (through expression of a dominant negative mutant) induced telomere elongation. In these experiments TRF1 did not detectably alter the activity of telomerase in cell extracts. Based on these observations it was proposed that TRF 1 negatively regulates telomerase at the level of individual telomeres; an increase in the amount of TRF1 at the telomere would create a negative signal for telomerase, whereas, a decrease would send a positive signal to telomerase [van Steensel and de Lange, *Nature*, 385:740–743 (1997)]. Interestingly, a similar mechanism of telomere length regulation exists in yeasts where it has been shown that Taz1p and Rap1p function as negative regulators of telomere length. As is the case for yeast telomere length regulation, the mechanism by which TRF1 controls telomere synthesis by telomerase is not fully understood [Conrad et al., *Cell*, 63:739–750 (1990); Cooper et al., *Nature*, 385:744–747 (1997); Lustig et al., Science, 250:549–553 (1990); Marcand et al., *Science*, 275:986–990 (1997); McEachern and Blackburn, *Nature*, 376:403–409 (1995)].

Indeed, telomere homeostasis involves a balance of lengthening and shortening activities. The telomerase catalytic subunit produces the lengthening activity, whereas other proteins including the telomere binding protein TRF1 are involved in establishing a telomere length equilibrium. Recently Bodnar et al. [*Science* 279:349–352 (1998)] have shown that extremely low levels of telomerase activity are insufficient to prevent telomere shortening; a result that is consistent with the observation that stem cells have low but detectable telomerase activity, yet continue to exhibit shortening of their telomeres throughout life.

Therefore, there is a need to isolate additional proteins, preferably enzymes involved in telomere homeostasis. Furthermore, there is a need to characterize such proteins. In addition, there is a need to design and develop drug screens to identify agents that modulate such proteins and thus can act as effectors on the important process of telomere length homeostasis.

The citation of any reference herein should not be construed as an admission that such reference is available as "Prior Art" to the instant application.

SUMMARY OF THE INVENTION

The present invention provides an isolated and/or recombinant nucleic acid encoding a protein, tankyrase, that binds to TRF1. In another embodiment, the nucleic acid encodes a tankyrase-related protein. In one embodiment the nucleic acid encodes a tankyrase or a tankyrase-related protein that has an amino acid sequence that has at least 25% identity with that of SEQ ID NO:2. In another embodiment the nucleic acid encodes a tankyrase or tankyrase-related protein comprising at least two, preferably three and more preferably all of the following domains: a domain that consists of homopolymeric tracts of histidine, proline and serine (HPS) preferably at the amino terminal end of the protein, an ankyrin-specific (ANK) repeat consensus domain, a sterile alpha motif (SAM) motif, and a poly(ADP-ribose) polymerase (PARP)-related domain. Preferably the order of the domains is identical to that found in human tankyrase having the amino acid sequence of SEQ ID NO:2. The tankyrase is preferably an animal protein, more preferably a vertebrate protein, and even more preferably a mammalian protein. In the most preferred embodiment the tankyrase is a human protein. In one such embodiment the protein is about 142-kDaltons and contains 24 ANK repeats, a SAM motif, a PARP-related domain, and an N-terminal domain rich in proline, histidine and serine (HPS). In another such embodiment tankyrase is a protein that is relatively enriched in the nuclear envelope fraction and in a tight association with the nuclear envelope e.g., remaining bound to the nuclear envelope even after extraction with 0.5 M NaCl and 8 M urea. In a particular embodiment of this type the nucleic acid encodes a tankyrase that is a human protein comprising the amino acid sequence of SEQ ID NO:2.In a related embodiment of this type the nucleic acid encodes a tankyrase comprising the amino acid sequence of SEQ ID NO:2 with a conservative amino acid substitution. In a more particular embodiment the nucleic acid comprises the coding sequence of SEQ ID NO:1. All of the recombinant and/or isolated nucleic acids of the present invention can further comprise a heterologous nucleotide sequence.

The present invention also provides nucleic acids, e.g., recombinant DNA molecules that comprise a nucleotide sequence encoding a fragment of a tankyrase that can bind to the acidic domain of a TRF1. In a preferred embodiment the fragment comprises at least a portion of the ANK repeat consensus domain of the tankyrase. In a particular embodiment of this type the nucleic acid encodes a fragment of the tankyrase that comprises the amino acids 436 to 796 of SEQ ID NO:2. In a related embodiment of this type the nucleic acid encodes a fragment of the tankyrase that comprises the amino acids 436 to 796 of SEQ ID NO:2 with a conservative amino acid substitution. In another such embodiment the nucleic acid encodes a fragment of the tankyrase that comprises the amino acids 181 to 1005 of SEQ ID NO:2. In a related embodiment of this type the nucleic acid encodes a fragment of the tankyrase that comprises the amino acids 181 to 1005 of SEQ ID NO:2 with a conservative amino acid substitution. In still another embodiment of this type, the nucleic acid encodes a fragment of the tankyrase that comprises the amino acids 336 to 1163 of SEQ ID NO:2. In a related embodiment of this type the nucleic acid encodes a fragment of the tankyrase that comprises the amino acids 336 to 1163 of SEQ ID NO:2 with a conservative amino acid substitution.

In another embodiment a nucleic acid, e.g., a recombinant DNA molecule comprises a nucleotide sequence encoding a fragment of a tankyrase comprising a PARP-related domain.

In one such embodiment the nucleic acid comprises a nucleotide sequence encoding a fragment of a tankyrase comprising the amino acids 1159 to 1314 of SEQ ID NO:2. In another such embodiment the nucleic acid comprises a nucleotide sequence encoding a fragment of a tankyrase comprising the amino acids 1159 to 1314 of SEQ ID NO:2 with a conservative amino acid substitution.

In still another embodiment a nucleic acid e.g., a recombinant DNA molecule, comprises a nucleotide sequence encoding a fragment of a tankyrase comprising a SAM motif. In one such embodiment the nucleic acid comprises a nucleotide sequence encoding a fragment of a tankyrase comprising the amino acids 1023 to 1088 of SEQ ID NO:2. In another such embodiment the nucleic acid comprises a nucleotide sequence encoding a fragment of a tankyrase comprising the amino acids 1023 to 1088 of SEQ ID NO:2 with a conservative amino acid substitution. As is true for all of the nucleic acids of the present invention, all of the recombinant DNA molecules encoding fragments of a tankyrase can further comprise a heterologous nucleotide sequence.

In yet another embodiment, a nucleic acid, e.g., a recombinant DNA molecule comprises a nucleotide sequence encoding a fragment of tankyrase comprising an HPS domain. In one such embodiment the nucleic acid comprises a nucleotide sequence encoding a fragment of a tankyrase comprising the amino acids 1–180 of SEQ ID NO:2. In another such embodiment the nucleic acid comprises a nucleotide sequence encoding a fragment of a tankyrase comprising the amino acids 1–180 of SEQ ID NO:2 with a conservative amino acid substitution.

The present invention also provides nucleic acids, e.g., recombinant DNA molecules that comprise a nucleotide sequence encoding a truncated tankyrase. In one such embodiment the nucleotide sequence comprises the coding sequence for amino acid residues 1–640 of SEQ ID NO:2. In another embodiment, the nucleotide sequence comprises the coding sequence for amino acid residues 1–881 of SEQ ID NO:2. In one embodiment the nucleotide sequence encodes SEQ ID NO:8 or SEQ ID NO:8 with a conservative amino acid substitution. In a particular embodiment of this type the nucleic acid has the nucleotide sequence of SEQ ID NO:7. In another embodiment the nucleotide sequence encodes SEQ ID NO:10 or SEQ ID NO:10 with a conservative amino acid substitution. In a particular embodiment of this type the nucleic acid has the nucleotide sequence of SEQ ID NO:9.

Nucleic acids that hybridize to the nucleotide sequences that encode the tankyrases, fragments thereof including truncated tankyrases, tankyrase-related proteins, and fragments thereof are also included in the present invention. In one such embodiment the nucleic acid is at least about 24 nucleotides, preferably at least about 48 nucleotides, and more preferably at least about 96 nucleotides. In a preferred embodiment of this type, the nucleic acid encodes a tankyrase which has at least one functional activity, preferably two and more preferably all, of the activities of human tankyrase as disclosed herein. In a particular embodiment the nucleic acid hybridizes to SEQ ID NO:1 under moderately stringent conditions. In a preferred embodiment of this type, the nucleic acid hybridizes to SEQ ID NO:1 under high stringency conditions.

The present invention further provides a nucleic acid that comprises about 15 or more, preferably about 24 or more, and more preferably about 36 or more consecutive nucleotides from SEQ ID NO:1. In a preferred embodiment of this type, the nucleic acid encodes a tankyrase which has at least one functional activity, preferably two, and more preferably all of the functional activities of human tankyrase as disclosed herein.

In addition, the present invention also provides nucleotide probes for the isolated and/or recombinant nucleic acids of the present invention. In a preferred embodiment of this type the nucleotide probe is for SEQ ID NO:1. Another nucleic acid that can be used as a probe contains the nucleotide sequence of SEQ ID NO:11. Still another nucleic acid that can be used as a probe contains the nucleotide sequence of SEQ ID NO:12.

All of the nucleic acids of the present invention can be comprised by a recombinant DNA molecule that is operatively linked to an expression control sequence. The present invention further provides expression vectors containing the recombinant DNA molecules of the present invention. In addition the present invention also provides methods of expressing a recombinant tankyrase protein or fragment thereof in a cell containing an expression vector of present invention. One such embodiment comprises culturing the cell in an appropriate cell culture medium under conditions that provide for expression of recombinant tankyrase or fragment thereof by the cell. Such methods can further include the step of purifying the recombinant tankyrase or fragment thereof. The purified form of the recombinant tankyrases or fragments thereof are also included as part of the present invention. In one preferred embodiment the nucleic acid encodes SEQ ID NO:2. In another preferred embodiment, the nucleic acid encodes a fragment of the tankyrase that comprises the amino acids 436 to 796 of SEQ ID NO:2.

Another aspect of the present invention provides an isolated and/or recombinant protein, tankyrase, that binds to TRF1. In another embodiment, the isolated and/or recombinant protein is a tankyrase-related protein. In one embodiment the tankyrase or tankyrase-related protein has an amino acid sequence that has at least 25% identity with that of SEQ ID NO:2. In another embodiment the tankyrase or tankyrase-related protein comprises at least two, preferably three, and more preferably all of the following domains: a domain rich in homopolymeric tracts of histidine, proline, and serine (HPS) which is preferably at the amino-terminal end of the protein, an ankyrin-specific (ANK) repeat consensus domain, a sterile alpha motif (SAM) motif, and a poly(ADP-ribose) polymerase (PARP)-related domain. The tankyrase is preferably an animal protein, more preferably a vertebrate protein, and even more preferably a mammalian protein. In the most preferred embodiment the tankyrase is a human protein. In one such embodiment the protein is about 142-kDaltons and contains about 24 ANK repeats, a SAM motif, an amino-terminus rich in histidine, proline and serine (i.e., an HPS domain), and a PARP-related domain. In another such embodiment the tankyrase is a protein that is relatively enriched in the nuclear envelope fraction and in a tight association with the nuclear envelope e.g., remaining bound to the nuclear envelope even after extraction with 0.5 M NaCl and 8 M urea.

In another embodiment the present invention provides a tankyrase that is a human protein comprising the amino acid sequence of SEQ ID NO:2. In a related embodiment of this type the tankyrase comprises the amino acid sequence of SEQ ID NO:2 with a conservative amino acid substitution. The present invention further provides proteolytic fragments of the tankyrase proteins of the present invention. The present invention also provides a protein comprising about 12 or more, preferably about 24 or more, and more preferably about 36 or more consecutive amino acids from SEQ ID NO:2 which functions as a tankyrase as disclosed herein.

The present invention also provides a fragment of a tankyrase that can bind to the acidic domain of a TRF1. In a preferred embodiment the fragment comprises at least a portion of the ANK repeat consensus domain of the tankyrase. In a particular embodiment of this type the fragment of the tankyrase comprises the amino acids 436 to 796 of SEQ ID NO:2. In a related embodiment of this type the fragment of the tankyrase comprises the amino acids 436 to 796 of SEQ ID NO:2 with a conservative amino acid substitution. In another such embodiment the fragment of the tankyrase comprises the amino acids 181 to 1005 of SEQ ID NO:2. In a related embodiment of this type the fragment of the tankyrase comprises the amino acids 181 to 1005 of SEQ ID NO:2 with a conservative amino acid substitution. In still another embodiment of this type, the fragment of the tankyrase comprises the amino acids 336 to 1163 of SEQ ID NO:2. In a related embodiment of this type the fragment of the tankyrase comprises the amino acids 336 to 1163 of SEQ ID NO:2 with a conservative amino acid substitution.

In still another embodiment a fragment of the tankyrase comprises an HPS domain. In one such embodiment the fragment of a tankyrase comprises the amino acids 1 to 180 of SEQ ID NO:2. In another such embodiment the fragment of a tankyrase comprises the amino acids 1 to 180 of SEQ ID NO:2 with a conservative amino acid substitution.

In yet another embodiment a fragment of a tankyrase comprises a PARP-related domain. In one such embodiment the fragment of a tankyrase comprises the amino acids 1159 to 1314 of SEQ ID NO:2. In another such embodiment the fragment of a tankyrase comprises the amino acids 1159 to 1314 of SEQ ID NO:2 with a conservative amino acid substitution.

In still another embodiment a fragment of a tankyrase comprises a SAM motif. In one such embodiment the fragment of a tankyrase comprises the amino acids 1023 to 1088 of SEQ ID NO:2. In another such embodiment the fragment of a tankyrase comprises the amino acids 1023 to 1088 of SEQ ID NO:2 with a conservative amino acid substitution. All of the recombinant and/or isolated tankyrase proteins and fragments of the present invention can further be part of a chimeric and/or fusion peptide or protein.

The present invention also provides truncated tankyrases. In one such embodiment the truncated tankyrase comprises amino acid residues 1–640 of SEQ ID NO:2. In another embodiment, the truncated tankyrase comprises amino acid residues 1–881 of SEQ ID NO:2. In one embodiment the truncated tankyrase comprises the amino acid sequence of SEQ ID NO:8 or SEQ ID NO:8 with a conservative amino acid substitution. In yet another embodiment the truncated tankyrase comprises the amino acid sequence of SEQ ID NO:10 or SEQ ID NO:10 with a conservative amino acid substitution.

The present invention further provides antibodies to the proteins and fragments thereof including truncated proteins, and proteolytic fragments of the proteins of the present invention. In one such embodiment the antibody is a polyclonal antibody. In another embodiment the antibody is a monoclonal antibody. In still another embodiment the antibody is a chimeric antibody. The present invention further provides an immortal cell line that produces a monoclonal antibody of the present invention.

In another aspect of the present invention is a method of selecting a candidate drug that interferes with the binding of a tankyrase and a TRF1. One such embodiment comprises contacting a candidate drug with a first protein or peptide comprising the acidic domain of a TRF1 and a second protein or peptide comprising a tankyrase fragment that can bind to the acidic domain of a TRF1 under conditions where the first protein or peptide and second protein or peptide bind in the absence of the candidate drug and determining the binding between the first protein or peptide and second protein or peptide; wherein a candidate drug is selected when the amount of binding determined in the presence of the drug is measurably less than in its absence. Preferably the fragment comprises at least a portion of the ANK repeat consensus domain of the tankyrase.

The present invention further provides methods of selecting a candidate drug that can modulate the PARP (and/or ARP) activity of a tankyrase. Such modulators can be either agonists or antagonists. Candidate drugs that are selected as agonists cause an increase in PARP (or ARP) activity whereas candidate drugs that are selected as antagonists (e.g., inhibitors) cause a decrease in PARP (and/or ARP) activity. One such embodiment comprises contacting a candidate drug with a tankyrase or a fragment of tankyrase that has PARP activity, NAD$^+$ and a poly ADP-ribosylating substrate under conditions in which the tankyrase (or the fragment) polyADP-ribosylates the substrate in the absence of the candidate drug. The polyADP-ribosylation state of the substrate (e.g., a histone) is then determined. A candidate drug is selected as an antagonist when the polyADP-ribosylation state of the substrate determined in the presence of the drug is measurably less than its absence. A candidate drug is selected as an agonist when the polyADP-ribosylation state of the substrate determined in the presence of the drug is measurably greater than its absence.

The present invention further provides methods of extending the lifespan of a non-tumor cell and/or inhibiting the growth of a tumor cell. One such embodiment comprises administering an inhibitor to tankyrase. In one particular embodiment of this type the inhibitor is 3-aminobenzamide. In a preferred embodiment of this type the cell is a human cell.

Yet another aspect of the present invention comprises a method of identifying the sequence of a homologue to the human tankyrase gene. One such embodiment comprises determining the homology of SEQ ID NO:2 to the amino acid sequences encoded by nucleic acids from a library of nucleic acids containing partial nucleotide sequences of coding regions of genes. Preferably this determination is aided by computer analysis. A nucleic acid containing a partial nucleotide sequence encoding a protein that is substantially homologous to SEQ ID NO:2 is then selected. The sequence of the coding region of the gene is then determined. The sequence is identified as being that of the homologue to the human tankyrase gene of the invention when it encodes a protein having an amino acid sequence that is substantially homologous to SEQ ID NO:2.

In one embodiment of the method, determining the sequence of the coding region is performed by sequencing an insert of a plasmid which contains the nucleic acid. In this case, the insert comprises the nucleic acid. In another embodiment, the method further comprises constructing a recombinant DNA that contains the coding region. In one such embodiment a recombinant protein is made by expressing the recombinant DNA. In a preferred embodiment of this type an activity of the tankyrase is assayed. In one such embodiment, the activity assayed is the ability of the recombinant protein to bind to TRF1. In another embodiment the sequence is identified as being that of the homologue to the human tankyrase gene when the recombinant protein has the activity of the human tankyrase. Recombinant DNA molecules and the recombinant tankyrases obtained by these methods are also part of the present invention.

The present invention further provides a method of transporting a protein to the nucleus. This method arises from the identification of the mechanism by which tankyrase is carried into the nucleus by TRF1. More particularly, the present invention provides a nucleotide sequence that encodes a protein or peptide of interest and a tankyrase fragment that can bind to the acidic domain of a TRF1. Minimally the fragment of tankyrase comprises at least a portion of the ANK repeat consensus domain. A particularly useful aspect of this portion of the present invention is that the protein of interest can be localized to the telomere. Such a protein can be used as a marker such as green fluorescent protein, or for its particular activity such as a particular RNase, Dnase, or even a protein kinase. In a preferred embodiment of this type the nucleic acid encodes a fragment of the tankyrase comprising the amino acids 436 to 796 of SEQ ID NO:2. In another embodiment of this type the nucleic acid encodes a fragment of the tankyrase comprising the amino acids 436 to 796 of SEQ ID NO:2 with a conservative amino acid substitution.

These and other aspects of the present invention will be better appreciated by reference to the following drawings and Detailed Description.

BRIEF DESCRIPTION OF THE DRAWINGS

FIGS. 1A–1D show that the human tankyrase cDNA encodes a 142-kD protein containing 24 ANK repeats, a SAM motif and a PARP-related domain. FIG. 1A shows the domain structure of tankyrase and TRF1. Lines below the schematic indicate inserts contained in the named plasmids used to generate recombinant protein for antibody production. Numbers indicate amino acid residues in tankyrase. FIG. 1B shows the predicted amino acid sequence of tankyrase. An alignment of the 24 ANK repeats is presented. Dashes within the repeats indicate gaps and sequences to the right of the repeats indicate insertions that occur after the underlined amino acid in the same line. Light shading indicates a match to the ANK repeat consensus derived by Michaely and Bennett [*Trends Cell Biol.*, 2:127–129 (1992)] or by Bork [*Proteins*, 17:363–374 (1993)] and darker shading is a match to the ankyrin-specific ANK repeat consensus derived from Peters and Lux [*Semin Hematol.*, 30:85–118 (1993)]. The SAM motif is doubly underlined and the PARP-related domain singly underlined. FIG. 1C shows the amino acid sequence alignment of the tankyrase SAM motif with Dm Bicaudal-C (*Drosophila melanogaster* Genbank #U15928), Hs Diacyl (*Homo sapiens* Diacyl glycerol kinase delta, Genbank #D73409) and Gg CEK9 (*Gallus gallus* chicken embryo kinase 9, Genbank # U23783). Identical residues found in HS tankyrase and at least one other sequence are shaded. Numbers on the left indicate the amino acid residues in the corresponding sequences. FIG. 1D shows the amino acid sequence alignment of the PARP-related domain of tankyrase with Dm tankyrase (*Drosophila melanogaster* EST, Genbank #AA391467), the catalytic domain of Hs PARP (*Homo sapiens*, Genbank # M32721) and DmPARP (*Drosophila melanogaster* Genbank # D13806) and a PARP-related domain in Hs KIAA0177 (*Homo sapiens*, Genbank #D79999). Identical residues found in Hs tankyrase and at least two sequences are shaded. Secondary structures are indicated by lines labeled c, d, e, f, g, m, n (β-strands) and L (α-helix). Identical amino acids conserved in the prokaryotic toxins, DT (diphtheria toxin) and ETA (exotoxin A), are indicated by an asterisk above the amino acid. Numbers on the left indicate the amino acid residues in the corresponding sequences.

FIG. 2A is a Northern blot of polyadenylated RNAs derived form the indicated human tissues probed with a tankyrase cDNA. Asterisks indicate the tankyrase transcripts. The blot was rehybridized with a β-actin probe. PBL is peripheral blood leukocytes. FIG. 2B is an immunoblot of proteins fractionated on 10% SDS-PAGE, transferred to nitrocellulose and probed with anti-tankyrase antibodies (lanes 1–3) or preimmune serum (lanes 4–6). Protein samples are: salt extracted nuclear pellet from rat testis (Testis) (lanes 1 and 4), whole cell lysates from HeLa cells (HeLa) (lanes 2 and 5) and products of a coupled in vitro transcription/translation reaction programmed with the tankyrase cDNA (IVTL) (lanes 3 and 6).

FIGS. 3A–3L show that the localization of exogenous tankyrase to telomeres is dependent upon TRF1. Hela 1 cells transfected with FLAG-tankyrase (FIGS. 3A–3D) or FLAG-tankyrase and TRF1 (FIGS. 3E–3L) were methanol-fixed and processed for indirect immunofluorescence. Cells were double-stained with anti-FLAG antibody M2 (FIGS. 3A, 3E and 3I) (green) and anti-TRF1 antibody 371 (FIGS. 3B, 3F and 3J) (red). (FIGS. 3C, 3G and 3K) indicates superimposition of the red and green images; yellow indicates colocalization of the red and green signal. DNA is stained with DAPI (D,H and L) (blue).

FIG. 4A shows Cell extracts prepared from HeLa 1 cells transiently transfected with TRF1 and FLAG-tankyrase-1 were subjected to immunoprecipitation followed by immunoblot analysis. Proteins were immunoprecipitated with an unrelated rabbit serum as a control (C) (lanes 1 and 4), anti-tankyrase antibodies (tankyrase) (lanes 2 and 6) or anti-TRF1 antibody 371 (TRF1) (lanes 3 and 5). Samples were processed, suspended in Laemmli buffer and divided in half. One set was not heated (left panel) and the other was heated at 100° C. for 5 min (right panel). Proteins were fractionated on 10% SDS-PAGE, transferred to nitrocellulose and probed with anti-TRF1 antibody 371 (left panel) or anti-tankyrase antibodies (right panel). Note that in the unheated sample the IgGs are not fully reduced and migrate as an 80 kdalton protein. FIG. 4B shows the identification of the interacting domains of TRF1 and tankyrase using the two-hybrid system. β-galactosidase levels were measured for strains containing plasmids expressing LexA or various LexA-TRF1 hybrids along with plasmids expressing the GAL4 activation domain (GAD) or the GAD-tankyrase hybrid containing 10 internal ANK repeats (9–19). The values represent an average of three independent transformations. Values <0.01 are indicated by 0.

FIG. 5A shows the co-localization of endogenous tankyrase with nuclear pore complex proteins by indirect immunofluorescence. Formaldehyde-fixed Hela 1 cells were double-stained with anti-tankyrase antibodies (1) and MAb414 (2), a monoclonal antibody that recognizes a family of nuclear pore complex proteins. FIG. 5B shows the immunblot analysis of co-fractionation of tankyrase with nuclear envelopes. Subcelluar fractions of rat liver are: cytosol (C) (lane 1), crude nuclei (CN) (lane 2), nuclei (N) (lane 3), supernatant containing nuclear contents (S) (lane 4) and pellet containing nuclear envelopes (P) (lane 5) after DNAase digestion of nuclei, supernatant (S) (lane 6) after extraction of nuclear envelopes with 0.5 M NaCl, and supernatant (S) (lane 7) and pellet (P) (lane 8) after extraction of salt-washed nuclear envelopes with 8 M urea. The amount of sample loaded for each fraction was based upon cell equivalents with an arbitrary value (x) for the starting number of cells: 1x (lanes 1 and 2), 100x (lanes 3 and 4) and 1000x (lanes 5–8). Samples were either fractionated by 10% SDS-PAGE and proteins visualized by staining with coomassie blue (top panel) or fractionated by 6.5% SDS-PAGE, transferred to nitrocellulose and probed with anti-tankyrase antibodies (bottom panel). Asterisks in the top panel indicate lamins A, B and C. Immunoreactive tankryin is indicated by an asterisk in the bottom panel. FIG. 5C shows the localization of tankyrase to nuclear pore complexes by immuno-electron microscopy. Formaldehyde-fixed Hela 1 cells were probed with anti-tankyrase antibodies followed by 5 nm-gold-conjugated anti-rabbit antibodies. Samples were processed by thin sectioning followed by analysis in the electron microscope. Shown are three panels depicting typical patterns of gold labeling of nuclear pore complexes. Magnification is 82,500 (top panel), 107,000 (bottom panels).

FIGS. 6A–6I are of HeLa 1.2.11 cells that were methanol-fixed and double-stained with anti-tankyrase antibodies (FIGS. 6A, 6D, and 6G, green) and anti-centrin antibodies (FIG. 6B, red) or anti-γ-tubulin antibodies (FIG. 6E, red) or anti-NuMA antibodies (FIG. 6I, red). FIGS. 6J–6L show the indirect immunofluorescence analysis of exogenous tankyrase. Hela 1 cells were transfected with FLAG-tankyrase, methanol-fixed and double-stained with anti-FLAG antibody M2 (FIG. 6J, green) and anti-γ-tubulin antibodies (FIG. 6K, red). (Merge) FIGS. 6C, 6F, 6I and 6L indicate superimposition of the red and green images; yellow indicates co-localization of the red and green signal. DAPI staining of DNA is shown in blue.

FIGS. 7A–7F show that endogenous tankyrase colocalizes with TRF1 to telomeres. Indirect immunofluorescence analysis of methanol-fixed HeLa 1.2.11 cells (FIGS. 7A–7C) or swollen, formaldehyde-fixed metaphase spreads from Hela 1.2.11 cells (FIGS. 7D–7F) by double-staining with anti-tankyrase antibodies (FIGS. 7A and 7D, green) and anti-TRF1 antibody #2 (FIGS. 7B and 7E, red). (Merge) FIGS. 7C and 7F indicates superimposition of the red and green images and yellow indicates colocalization of the red and green signal. DAPI staining of DNA is shown in blue.

FIG. 8A shows that tankyrase plays a role in the assembly of the bouquet structure during prophase of meiosis I. Tankyrase mediates attachment of telomeres to the nuclear envelope and the subsequent clustering of telomeres at the centrosome. FIG. 8B shows that TRF1 recruits tankyrase to long telomeres to inhibit telomerase. Long telomeres or an increase in TRF1 expression induces a higher order structure that promotes tankyrase binding. Tankyrase ADP-ribosylates telomerase rendering it inactive.

In FIG. 9A Tankyrase is shown to ADP-ribosylates itself and TRF1. Tankyrase was allowed to modify itself and TRF1 in the presence of [$^{32}$P]NAD$^+$ and the products were analyzed by Coomassie-Blue staining (left) and autoradiography (right) of SDS-PAGE gels (see Example 1, below). Reactions contained the proteins indicated above the lanes at the following amounts: TRF1 at 4 μg (+), tankyrase at 4 μg (+) or at a range of 0, 0.8, and 4 μg (triangle). All reactions contained 1.3 μM [$^{32}$P]NAD$^+$ (+) and three reactions were also supplemented with increasing amounts of cold NAD$^+$ (0.04, 0.2, and 1 mM, triangle). FIG. 9B demonstrates that ADP-ribosylation activity is intrinsic for tankyrase. Tankyrase was immunoprecipitated with preimmune or α-tankyrase antibodies as indicated and incubated in a PARP assay with [$^{32}$P]NAD$^+$ and the products were detected by autoradiography (see Example 1, below). FIG. 9C shows that Tankyrase is inhibited by the PARP inhibitor 3-aminobenzamide (3AB). Reactions containing 4 μg tankyrase (+), without (−) or with (+) 4 μg TRF1, and 1.3 μM [$^{32}$P]NAD$^+$ were incubated without (−) or with (+) 1 mM 3AB and processed as in FIG. 9A. FIG. 9D demonstrates that Tankyrase products contain poly(ADP-ribose). Tankyrase and TRF1 were added as in panel FIG. 9C. Reactions for the left panel contained no NAD$^+$ (−) or 1.3 μM [$^{32}$P]NAD$^+$ supplemented with 1 μM or 1 mM cold NAD$^+$ (triangle). Reactions for the right panel were identical to the reactions on the left but lacked labeled NAD$^+$. Products were transferred to nitrocellulose and autoradiographed (left) or immunoblotted with monoclonal antibody 10H to poly(ADP-ribose) (right panel) (see Example 1, below). FIG. 9E shows the inhibition of TRF-1 by Tankyrase. The Gel-shift assay for the TTAGGG repeat binding activity of TRF1 used a duplex [TTAGGG]$_{12}$ DNA as a probe. Binding reactions contained the components indicated above the lanes. Tankyrase was varied from 2.5 to 200 ng per 20 μl incubation in three-fold dilution steps (triangles). TRF1 was either present at 13 ng (+) or varied from 120 to 13 ng in three-fold dilution steps (triangle). NAD$^+$ was at 0 (−) or 0.2 mM (+). The asterisks indicate the position of TRF1-containing complexes as determined by antibody super-shift experiments.

DETAILED DESCRIPTION OF THE INVENTION

Figure 1A:
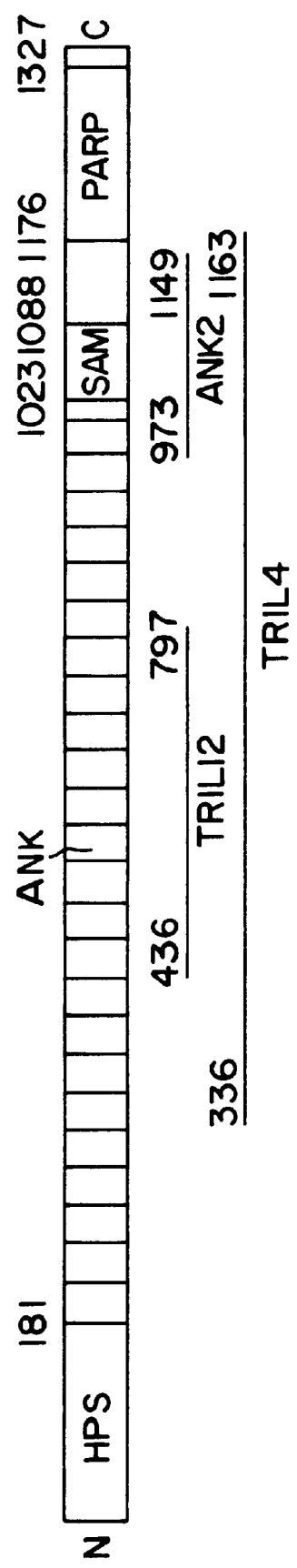

A novel telomeric protein tankyrase (TRF1 interacting ankyrin) has been identified by a two-hybrid screen with TRF1. Tankyrase is the third mammalian telomeric protein to be described and it differs in several respects from the previously identified factors TRF1 and TRF2. For example, the predicted amino acid sequence of tankyrase indicates a novel domain organization, completely unrelated to TRF1 and TRF2. In addition, tankyrase localizes to telomeres not via the binding of telomeric DNA like TRF1 and TRF2, but rather, through protein-protein interaction with TRF1. A human tankyrase, as exemplified below, carries a region of 24 ankyrin repeats (a hallmark of the ankyrin family) that includes the TRF1 binding site, a sterile alpha motif (SAM) protein interaction motif, and a C-terminal domain with significant homology to the catalytic domain of poly(ADP-ribose) polymerase (PARP), an enzyme involved in DNA repair and genome stability. Tankyrase binds to the telomeric protein TRF1, which is a negative regulator of telomere length maintenance.

Expression of the tankyrase cDNA in HeLa cells revealed a telomeric staining pattern, but only when tankyrase was co-transfected with TRF1, indicating a possible link between tankyrase localization to telomeres and TRF1 synthesis. Analysis of the subcellular distribution of the endogenous protein indicated that tankyrase co-localized with TFR1 to telomeres in interphase and mitosis. In addition to its telomeric location, tankyrase is located at nuclear pore complexes during interphase and at centrosomes in mitosis.

Given its strong homology to PARP, tankyrase not surprisingly functions as an enzyme and as such represents the first indication for an enzymatic activity other than telomerase associated with eukaryotic telomeres. Indeed, the PARP-related domain of tankyrase appears to be involved in the telomere length regulation by TRF1, and could directly modify the effect of TRF1 on telomeres.

It has only recently become apparent that telomere dynamics plays a major role in the life-cycle of a cell. The regulation of telomere length has been implicated in the process of aging, as well as in cancer, and other human diseases. For example, the mutation in ataxia telangiectasia has recently be shown to confer a predisposition to accelerated telomere shortening in peripheral blood lymphocytes [Metcalfe et al., Nature Genetics, 13:350–353 (1996)].

Telomeres undergo progressive shortening during the development of human somatic tissue. Such telomere shortening eventually limits cell proliferation and leads to aging. Consistently, the number of cell divisions that primary human fibroblasts go through in culture is dependent on their initial telomere length. This correlation corresponds to a molecular clock that limits the potential of primary cells to replicate, and indicates that immortalization of human somatic cells involves a mechanism that must halt normal telomere shortening. This implies that successfully inducing the elongation of telomeres, either in vitro or in vivo, could counteract this aspect of the aging process, and furthermore, could extend the life-span of human cells and tissues. In this capacity tankyrase, by inhibiting the action of TRF1 could act as such a counteracting agent.

On the other hand cancer cells appear to have the ability to maintain their telomeres at specific lengths. Not surprisingly, many cancer cells contain the enzyme telomerase, which acts to lengthen telomeres and thereby counteract the shortening of the telomere that would otherwise occur during normal cellular division. Major efforts in the pharmaceutical industry are currently focused on telomerase as a target in cancer chemotherapy. The rationale of this approach is that inhibition of telomerase should lead to telomere shortening in the tumors and this process is eventually expected to halt proliferation of the cancer cells. In addition, telomeres of cancer cells are generally significantly shorter than those of the corresponding normal cells. This decrease in telomere length may be a factor in the instability of the genome of cancer cells. Since there is evidence that tankyrase can act as a regulatory enzyme the inhibition of tankyrase could potentially lead to consequences that are detrimental to the cell including tumor cells [McEachern and Blackburn, Nature, 376:403–409 (1995)].

In humans, telomere maintenance is controlled by a negative feedback mechanism that stabilizes telomeres in telomerase-expressing cells. TRF1 plays a role in the regulation of telomere length. TRF1 performs its role in the regulation, at least in part, by binding to telomeres and inhibiting telomerase-catalyzed telomere elongation. As disclosed herein, TRF1 may also regulate telomere length by being a binding partner to tankyrase. Long term overexpression of TRF1s in telomerase-positive tumor cell lines results in a gradual and progressive telomere shortening, whereas the expression of a dominant-negative allele encoding an A-TRF, a specific inhibitor of TRF1, inhibits binding of endogenous TRF1 to telomeres, and thereby permits telomere elongation. Importantly, the affinity of tankyrase for TRF1 appears to increase when TRF1 is bound to the telomere.

Inhibition of TRF1 binding to telomeres has been shown to lead to telomere elongation of cells expressing telomerase in vitro. Based on this data it follows that in vivo inhibition of TRF1 will result in telomere elongation in cells that express telomerase. Telomerase is expressed in self-renewing tissues such as bone marrow cells, peripheral blood T and B cells, and in basal keratinocytes. In these cells, and in other normal human cells that express telomerase, inhibition of TRF1 due to tankyrase activity should lead to telomere elongation and concomitant extension of life-span.

Aside from the myriad of therapeutic applications for cells containing recombinant tankyrase of the present invention, cells having an extended life-span due, at least in part to the presence of modulators of tankyrase activity, obtained by the methods described herein, can also have important ex vivo applications such as in the production of bioengineered products. Indeed, cells in which telomere length can be manipulated are an important tool for basic analysis of telomere structure, function, and dynamics and for the analysis of telomerase function and regulation. In addition, the manipulation of telomere length provides insight in the relationship between telomere dynamics and cellular life-span. The disclosure of a new protein involved in telomere homeostasis provides new avenues for drug design and genetic manipulations.

More specifically, the direct correlation shown between telomere maintenance and cellular senescence, by [Bodner et al., Science, 279:349–352 (1993)] for example indicates that the compositions and processes provided by the present invention can also play a direct role in preventing and/or treating (1) atrophy of the skin through loss of extracellular matrix homeostasis in dermal fibroblasts [Takeda et al., Arch. Dermatol. 130:87 (1994)]; (2) age-related macular degeneration [Bouton et al., J. Neurosci. 15:4992 (1995)]; (3) and atherosclerosis [Kumazaki et al., J. Med. Sci., 42:97 (1993)]. In addition, Bodner et al., [supra] has pointed out that cells having an extended life-span can also have important ex vivo applications in the production of bioengineered products such as recombinant proteins. Furthermore, the extension of cellular in vitro life-span of normal human cells through the teachings of the present invention also has applications in creating large populations of normal human cells in the laboratory. Large numbers of human cells can be important for generation of tissues (e.g. skin for burn victims) and even stem cells, including for creation of cell populations used in ex vivo gene-therapy.

Therefore, if appearing herein, the following terms shall have the definitions set out below:

As used herein the term "tankyrase" is used interchangeably with the term "tankyrin" and refers to a protein that has binding affinity for TRF1, and more specifically the N-terminal acidic domain of a TRF1. Tankyrase contains an ankyrin-specific (ANK) repeat consensus domain, a sterile alpha motif (SAM) motif; and a poly(ADP-ribose) polymerase (PARP)-related domain as described below. Preferably it also contains a domain that is rich in proline, histidine and serine (HPS), and more preferably the HPS domain is at the amino terminal end of the protein. Tankyrase also has PARP activity in vitro with either TRF1 and/or tankyrase functioning as acceptors/substrates for ADP-ribosylation. As exemplified below a human tankyrase has the amino acid sequence of SEQ ID NO:2 which is encoded by the nucleotide sequence of SEQ ID NO:1. A tankyrase is a specific type of tankyrase-related protein defined below.

As used herein, a "tankyrase-related protein" is a protein that is identified as a member of a family of proteins by its structural similarity with human tankyrase as exemplified herein by the first member, human tankyrase having SEQ ID NO:2. Minimally a "tankyrase-related protein" contains at least two structural and/or functional domains in common with human tankyrase, (e.g., an HPS, ANK, SAM or PARP-like domain), or alternatively has about at least 25% amino acid identity with human tankyrase having an amino acid sequence of SEQ ID NO:2 over a contiguous block of about 1300 amino acid residues, preferably taking into account any particular deletions or insertions that could otherwise alter the correspondence between the two amino acid sequences, or alternatively has about at least 25% amino acid homology with human tankyrase having an amino acid sequence of SEQ ID NO:2 as determined as a percent likeness of the amino acid sequence of the tankyrase-related protein with SEQ ID NO:2 with a standard computer analysis that is comparable, and preferably identical to that determined with an Advanced Blast search at www.ncbi.nlm.nih.gov under the default filter conditions. In a preferred embodiment the "tankyrase-related protein" has two or more of these properties. In addition, it is preferable that the protein has at least three domains in common with a human tankyrase and more preferably it has all four of these domains. In the most preferred embodiment of this type, the order of the domains is identical to that of human tankyrase as disclosed herein. Similarly, it is preferable that the tankyrase-related protein has about at least 50% amino acid identity, and more preferably at least about 75%, and even more preferably at least about 90% amino acid identity with human tankyrase having the amino acid sequence SEQ ID NO:2 over a contiguous block of about 1300 amino acid residues. Alternatively, it is also preferable that the tankyrase-related protein have about at least 50% amino acid homology and more preferably at least about 75% and even more preferably at least about 90% amino acid homology with human tankyrase having the amino acid sequence SEQ ID NO:2, with the homology determined by a standard computer analysis as cited above. A tankyrase-related protein preferably functions in at least one respect like human tankyrase, e.g., binding a TRF such as TRF1, having an ADP-ribosylating activity, and/or having a role in telomere function. More preferably the tankyrase-related protein binds a TRF such as TRF1, has an ADP-ribosylating activity, and has a role in telomere function.

As used herein, an "ANK" domain is a protein domain that contains 24 ankyrin-specific repeats [Bork, Proteins, 17:363–374 (1993); Michaely and Bennett, Trends Cell Biol., 2:127–129 (1992) and Bennett, J. Biol. Chem., 267:8703–8706 (1992)].

As used herein, a "SAM" domain is a sterile alpha motif, i.e., a 65–70 amino acid domain found in 1–3 copies in a diverse group of proteins implicated in developmental processes [Ponting, Protein Science, 4:1928–1930 (1995); Schultz et al., Protein Science, 6:249–253 (1997)].

As used herein, a "PARP-like" domain is a protein domain that corresponds to the PARP domain as described by Domenighini et al. [Mol. Microbiol., 14:41–50 (1994) and Ruf et al., Proc. Natl. Acad. Sci. USA, 93:7481–7485 (1996)].

As used herein, an "HPS" domain is a protein domain contained within a region of about 150 consecutive amino acids or less, in which homopolymeric runs (or tracts) of histidine, proline, and serine are found. The polymeric runs minimally contain 5 consecutive prolines, or 5 consecutive histidines, or 5 consecutive serines. An HPS domain is exemplified in the N-terminal region of the amino acid sequence of SEQ ID NO:2.

The telomeric repeat binding factor 1, TRF1, plays a role in the regulation of telomere maintenance by acting as a negative regulator of telomere elongation is a dimeric protein that binds to a specific telomeric repeat sequence found at the ends of telomeres [U.S. Pat. No. 5,733,730, Issued Mar. 31, 1998, and U.S. patent application Ser. Nos. 08/938, 052, filed Sep. 26, 1997, and 09/018,635 filed Feb. 4, 1998, all of which are hereby incorporated by reference in their entireties]. In vertebrates, the telomeric repeat sequence is TTAGGG. TRF1 has three distinct structural domains, a DNA binding domain encompassing the region of the protein that binds to the specific telomeric repeat sequence, a dimerization domain encompassing the region of the monomer that binds to its geminate partner to form a dimer, and an N-terminal acidic region that binds to tankyrase as described below.

The term "telomeric repeat binding factor 2", or "TRF2", is a telomeric protein that is required to maintain the correct structure at telomere termini, and thereby protect against end-to-end fusions [U.S. patent application Ser. Nos. 08/938,052, filed Sep. 26, 1997; and 09/018,635 filed Feb. 4, 1998]. TRF2, therefore, plays a role in the successful progression through the cell division cycle. As such, TRF2 is involved in the main functions ascribed to telomeres in somatic human cells and is therefore a player in the loss of telomere function and growth arrest that accompanies telomere shortening in normal and transformed human cells. TRF2 has three distinct structural domains, a DNA binding domain encompassing the region of the protein that binds to the specific telomeric repeat sequence, a dimerization domain encompassing the region of the monomer that binds to its geminate partner to form a dimer, and an N-terminal basic region.

As used herein an "altered TRF" ("A-TRF") is a modified vertebrate TRF that binds to TRF to form a heterodimer [U.S. patent applications Ser. Nos. 08/800,264, filed Feb. 14, 1997, and 09/018,628 filed Feb. 4, 1998 hereby incorporated by reference in their entireties.]. The resulting heterodimer has a measurably lower binding affinity for the TRF telomeric repeat sequence than does the corresponding TRF homodimer. Thus the A-TRF hinders and/or prevents the binding of the corresponding TRF to its telomere repeat sequence binding site. An "A-TRF1" is an altered TRF1, whereas an "A-TRF2" is an altered TRF2.

As used herein the terms "approximately" and "about" are used to signify that a value is within ten percent of the indicated value i.e., a protein fragment containing "approximately" 140 amino acid residues can contain between 126 and 154 amino acid residues.

As used herein the term "binds to" is meant to include all such specific interactions that result in two or more molecules showing a preference for one another relative to some third molecule. This includes processes such as covalent, ionic, hydrophobic and hydrogen bonding but does not include non-specific associations such solvent preferences.

As used herein, the term "homologue" refers to the relationship between proteins that have a common evolutionary origin and differ because they originate from different species. For example, chicken TRF2 is a homologue of human TRF2.

Genes Encoding Tankyrase

The present invention contemplates isolation of a gene encoding a tankyrase or a tankyrase-related protein, preferably from a vertebrate, including a full length, or naturally occurring form of tankyrase from any species, preferably an animal, more particularly mammalian, and even more particularly a human source.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual,* Second Edition (1989) Cold Spring Harbor Laboratory Press, Cold Spring Harbor, New York (herein "Sambrook et al., 1989"); *DNA Cloning: A Practical Approach,* Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology,* John Wiley & Sons, Inc. (1994).

Therefore, if appearing herein, the following terms shall have the definitions set out below.

As used herein, the term "gene" refers to an assembly of nucleotides that encode a polypeptide, and includes cDNA and genomic DNA nucleic acids.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "heterologous nucleotide sequence" as used herein is a nucleotide sequence that is added to a nucleotide sequence of the present invention by recombinant methods to form a nucleic acid which is not naturally formed in nature. Such nucleic acids can encode chimeric and/or fusion proteins. Thus the heterologous nucleotide sequence can encode peptides and/or proteins which contain regulatory and/or structural properties. In another such embodiment the heterologous nucleotide can encode a protein or peptide that functions as a means of detecting the protein or peptide encoded by the nucleotide sequence of the present invention after the recombinant nucleic acid is expressed. In still another such embodiment the heterologous nucleotide can function as a means of detecting a nucleotide sequence of the present invention. A heterologous nucleotide sequence can comprise non-coding sequences including restriction sites, regulatory sites, promoters and the like.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). However, unless specifically stated otherwise, a designation of a nucleic acid includes both the non-transcribed strand referred to above, and its corresponding complementary strand. Such designations include SEQ ID NOs:. A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5× SSC, 0.1% SDS, 0.25% milk, and no formamide; or 30% formamide, 5× SSC, 0.5% SDS). Moderate stringency hybridization conditions correspond to a higher $T_m$, e.g., 40% formamide, with 5× or 6× SSC. High stringency hybridization conditions correspond to the highest $T_m$, e.g., 50% formamide, 5× or 6× SSC. Hybridization requires that the two nucleic acids contain complementary sequences, although depending on the stringency of the hybridization, mismatches between bases are possible. The appropriate stringency for hybridizing nucleic acids depends on the length of the nucleic acid and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 12 nucleotides; preferably at least about 16 nucleotides; and more preferably the length is at least about 24 nucleotides; and most preferably 36 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) [Reeck et al., Cell, 50:667 (1987)].

Accordingly, the term "sequence similarity" in all its grammatical forms refers to the degree of identity or correspondence between nucleic acid or amino acid sequences of proteins that do not share a common evolutionary origin [see Reeck et al., 1987, supra]. However, in common usage and in the instant application, the term "homologous," when modified with an adverb such as "highly," may refer to sequence similarity and not a common evolutionary origin.

In a specific embodiment, two DNA sequences are "substantially homologous" or "substantially similar" when at least about 50% (preferably at least about 75%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, in a particular embodiment, two amino acid sequences are "substantially homologous" or "substantially similar" when greater than 30% of the amino acids are identical, or greater than about 60% are similar (functionally identical). Preferably, the similar or homologous sequences are identified by alignment using, for example, the GCG (Genetics Computer Group, Program Manual for the GCG Package, Version 7, Madison, Wis.) pileup program, using the default parameters.

The term "corresponding to" is used herein to refer similar or homologous sequences, whether the exact position is identical or different from the molecule to which the similarity or homology is measured. Thus, the term "corresponding to" refers to the sequence similarity over a given sequence range (e.g. 50 nucleotides) and not the numbering of the amino acid residues or nucleotide bases.

A gene encoding a tankyrase or a tankyrase-related protein, whether genomic DNA or cDNA, can be isolated from any source, particularly from a human cDNA or genomic library. Methods for obtaining a tankyrase gene with the nucleotide information disclosed herein is well known in the art [see, e.g., Sambrook et al., 1989, supra].

Accordingly, any animal cell potentially can serve as the nucleic acid source for the molecular cloning of a tankyrase gene. The DNA may be obtained by standard procedures known in the art from cloned DNA (e.g., a DNA "library"), by chemical synthesis, by cDNA cloning, or by the cloning of genomic DNA, or fragments thereof, purified from the desired cell [see, for example, Sambrook et al., 1989, supra; Glover, D. M. (ed.), 1985, DNA Cloning: A Practical Approach, MRL Press, Ltd., Oxford, U.K. Vol. I, II]. Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired tankyrase gene may be accomplished in a number of ways. For example, if an amount of a portion of a tankyrase gene or its specific RNA, or a fragment thereof, is available and can be purified and labeled, the generated DNA fragments may be screened by nucleic acid hybridization to the labeled probe [Benton and Davis, *Science,* 196:180 (1977); Grunstein and Hogness, *Proc. Natl. Acad. Sci. U.S.A.,* 72:3961 (1975)]. For example, a set of oligonucleotides corresponding to the partial amino acid sequence information obtained for the tankyrase protein can be prepared and used as probes for DNA encoding a tankyrase. Preferably, a fragment is selected that is highly unique to a tankyrase. Those DNA fragments with substantial homology to the probe will hybridize. As noted above, the greater the degree of homology, the more stringent hybridization conditions can be used. In a specific embodiment, stringent hybridization conditions are used to identify a homologous tankyrase gene.

Further selection can be carried out on the basis of the properties of the gene, e.g., if the gene encodes a protein product having the isoelectric, electrophoretic, amino acid composition, or partial amino acid sequence of a tankyrase as disclosed herein. Thus, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing or non-equilibrium pH gel electrophoresis behavior, proteolytic digestion maps, or antigenic properties as known for a tankyrase.

A tankyrase or tankyrase-related protein gene can also be identified by mRNA selection, i.e., by nucleic acid hybridization followed by in vitro translation. In this procedure, nucleotide fragments are used to isolate complementary mRNAs by hybridization. Such DNA fragments may represent available, purified tankyrase DNA, or may be synthetic oligonucleotides designed from the partial amino acid sequence information. Immunoprecipitation analysis or functional assays (e.g., tankyrase activity) of the in vitro translation products of the products of the isolated mRNAs identifies the mRNA and, therefore, the complementary DNA fragments, that contain the desired sequences. In addition, specific mRNAs may be selected by adsorption of polysomes isolated from cells to immobilized antibodies specifically directed against tankyrase.

The nucleotide sequence of the human tankyrase, SEQ ID NO:1 can also be used to search for highly homologous genes from other species, or for proteins having at least one homologous domain, using computer data bases containing either partial or full length nucleic acid sequences. Human ESTs, for example, can be searched. The human tankyrase sequence can be compared with human sequences, e.g., in GenBank, using GCG software and the blast search program for example. Matches with highly homologous sequences or portions thereof can then be obtained.

If the sequence identified is an EST, the insert containing the EST can be obtained and then fully sequenced. The resulting sequence can then be used in place of, and/or in conjunction with SEQ ID NO:1 to identify other ESTs which contain coding regions of the tankyrase homologue (or tankyrase domain homologue). Plasmids containing the matched EST for example can be digested with restriction enzymes in order to release the cDNA inserts. If the plasmid does not contain the full length homologue the digests can be purified, e.g., run on an agarose gel and the bands corresponding to the inserts can be cut from the gel and purified. Such purified inserts are likely to contain overlapping regions which can be combined as templates of a PCR reaction using primers which are preferably located outside of the tankyrase open reading frame. Amplification should yield the expected product which can be ligated into a vector and used to transform an *E. coli* derivative e.g., via TA cloning (Invitrogen) for example. A resulting full-length tankyrase homologue can be placed into an expression vector and the expressed recombinant tankyrase can then be assayed for TRF1 binding activity.

Alternatively, plasmids containing matched EST homologue fragments can be used to transform competent bacteria (e.g., from Gibco BRL, Gaithersburg, Md.). Bacteria can be streaked, then grown up overnight. Plasmid preps can be performed (e.g., Quiagen Corp, Santa Clarita, Calif.) and the plasmids can be digested by simultaneous restriction digest. Products of the digest can be separated by size on an agarose gel, for example, and purified. The corresponding bands cut from these gels can be ligated to form a full length tankyrase cDNA and used to transform competent bacteria and the resulting plasmid can be purified.

A radiolabeled tankyrase cDNA can be synthesized using the selected mRNA (from the adsorbed polysomes) as a template. The radiolabeled mRNA or cDNA may then be used as a probe to identify homologous tankyrase DNA fragments from among other genomic DNA fragments.

The present invention also relates to cloning vectors containing genes encoding the domains of the tankyrases of the invention. The production and use of such derivatives and analogs are within the scope of the present invention.

A modified tankyrase can be made by altering nucleic acid sequences encoding the tankyrase by making substitutions, additions or deletions that provide for functionally equivalent molecules. Preferably, such derivatives are made that have enhanced or increased effect on telomere elongation relative to the tankyrase. For example, a preferred tankyrase may bind TRF1 more tightly than the native form.

Due to the degeneracy of nucleotide coding sequences, other DNA sequences which encode substantially the same amino acid sequence as a tankyrase gene may be used in the practice of the present invention including those comprising conservative substitutions thereof. These include but are not limited to modified allelic genes, modified homologous genes from other species, and nucleotide sequences comprising all or portions of tankyrase genes which are altered by the substitution of different codons that encode the same amino acid residue within the sequence, thus producing a silent change. Likewise, the tankyrase derivative of the invention can include, but is not limited to, those containing, as a primary amino acid sequence, all or part of the amino acid sequence of a tankyrase protein including altered sequences in which functionally equivalent amino acid residues are substituted for residues within the sequence resulting in a conservative amino acid substitution. And thus, such substitutions are defined as a conservative substitution.

For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to significantly affect apparent molecular weight as determined by polyacrylamide gel electrophoresis, or isoelectric point.

Particularly preferred conservative substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced at a potential site for disulfide bridges with another Cys. Pro may be introduced because of its particularly planar structure, which induces β-turns in the protein's structure.

The genes encoding tankyrase derivatives and analogs of the invention can be produced by various methods known in the art. The manipulations which result in their production can occur at the gene or protein level. For example, a tankyrase gene sequence can be produced from a native tankyrase clone by any of numerous strategies known in the art [Sambrook et al., 1989, supra]. The sequence can be cleaved at appropriate sites with restriction endonuclease(s), followed by further enzymatic modification if desired, isolated, and ligated in vitro. In the production of the gene encoding a derivative or analog of a tankyrase, care should be taken to ensure that the modified gene remains within the same translational reading frame as the tankyrase gene, uninterrupted by translational stop signals, in the gene region where the desired activity is encoded.

Additionally, the tankyrase-encoding nucleic acid sequence can be produced by in vitro or in vivo mutations, to create and/or destroy translation, initiation, and/or termination sequences, or to create variations in coding regions and/or form new restriction endonuclease sites or destroy preexisting ones, to facilitate further in vitro modification. Preferably such mutations will further enhance the specific properties of the tankyrase gene product. Any technique for mutagenesis known in the art can be used, including but not limited to, in vitro site-directed mutagenesis [Hutchinson, C., et al., *J. Biol. Chem.*, 253:6551 (1978); Zoller and Smith, *DNA*, 3:479–488 (1984); Oliphant et al., *Gene*, 44:177 (1986); Hutchinson et al., *Proc. Natl. Acad. Sci. U.S.A.*, 83:710 (1986)], use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70). A general method for site-specific incorporation of unnatural amino acids into proteins is described in Christopher J. Noren, Spencer J. Anthony-Cahill, Michael C. Griffith, Peter G. Schultz, *Science*, 244:182–188 (April 1989). This method may be used to create analogs with unnatural amino acids.

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., E. coli, and facile purification for subsequent insertion into an appropriate expression cell line, if such is desired. For example, a shuttle vector, which is a vector that can replicate in more than one type of organism, can be prepared for replication in both E. coli and Saccharomyces cerevisiae by linking sequences from an E. coli plasmid with sequences from the yeast 2μ plasmid.

In an alternative method, the desired gene may be identified and isolated after insertion into suitable cloning vector in a "shot gun" approach. Enrichment for the desired gene, for example, by size fractionation, can be done before insertion into the cloning vector.

Expression of Tankyrase Polypeptides

The nucleotide sequence coding for a tankyrase, or a tankyrase related protein, or a functionally equivalent derivative including a chimeric protein thereof, can be inserted into an appropriate expression vector, i.e., a vector which contains the necessary elements for the transcription and translation of the inserted protein-coding sequence. Such elements are termed herein a "promoter." Thus, the nucleic acid encoding a tankyrase of the invention is operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding the corresponding tankyrase and/or its flanking regions. Any person with skill in the art of molecular biology or protein chemistry, in view of the present disclosure, would readily know how to assay the protein expressed as described herein, to determine whether such a modified protein is indeed a tankyrase. Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant tankyrase of the invention or a tankyrase-related protein, or functionally equivalent derivative, or chimeric construct may be expressed chromosomally, after integration of the coding sequence by recombination. In this regard, any of a number of amplification systems may be used to achieve high levels of stable gene expression [See Sambrook et al., 1989, supra]. Chromosomal integration, e.g., by homologous recombination is desirable where permanent expression is required, such as to immortalize an antibody-producing plasma cell. In other embodiments, such as for in vitro propagation of cells for transplantation, transient transfection such as with a plasmid, is preferable. This way, the cell can be propagated indefinitely in vitro, but will terminally differentiate when reintroduced in vivo.

The cell containing the recombinant vector comprising the nucleic acid encoding a tankyrase is cultured in an appropriate cell culture medium under conditions that provide for expression of the tankyrase by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of a tankyrase or tankyrase-related protein may be controlled by any promoter/enhancer element known in the art, but these regulatory elements must be functional in the host selected for expression. Promoters which may be used to control tankyrase gene expression include, but are not limited to, the SV40 early promoter region [Benoist and Chambon, Nature, 290:304–310 (1981)], the promoter contained in the 3' long terminal repeat of Rous sarcoma virus [Yamamoto, et al., Cell, 22:787–797 (1980)], the herpes thymidine kinase promoter [Wagner et al., Proc. Natl. Acad. Sci. U.S.A., 78:1441–1445 (1981)], the regulatory sequences of the metallothionein gene [Brinster et al., Nature, 296:39–42 (1982)]; prokaryotic expression vectors such as the β-lactamase promoter [Villa-Kamaroff, et al., Proc. Natl. Acad. Sci. U.S.A., 75:3727–3731 (1978)], or the tac promoter [DeBoer, et al., Proc. Natl. Acad. Sci. U.S.A., 80:21–25 (1983)]; see also "Useful proteins from recombinant bacteria" in Scientific American, 242:74–94 (1980); promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells [Swift et al., Cell, 38:639–646 (1984); Ornitz et al., Cold Spring Harbor Symp. Quant. Biol., 50:399–409 (1986); MacDonald, Hepatology, 7:425–515 (1987)]; insulin gene control region which is active in pancreatic beta cells [Hanahan, Nature, 315:115–122 (1985)], immunoglobulin gene control region which is active in lymphoid cells [Grosschedl et al., Cell, 38:647–658 (1984), Adames et al., Nature, 318:533–538 (1985); Alexander et al., Mol. Cell. Biol., 7:1436–1444 (1987)], mouse mammary tumor virus control region which is active in testicular, breast, lymphoid and mast cells [Leder et al., Cell, 45:485–495 (1986)], albumin gene control region which is active in liver [Pinkert et al., Genes and Devel., 1:268–276 (1987)], alpha-fetoprotein gene control region which is active in liver [Krumlauf et al., Mol. Cell. Biol., 5:1639–1648 (1985); Hammer et al., Science, 235:53–58 (1987)], alpha 1-antitrypsin gene control region which is active in the liver [Kelsey et al., Genes and Devel., 1:161–171 (1987)], beta-globin gene control region which is active in myeloid cells [Mogram et al., Nature, 315:338–340 (1985); Kollias et al., Cell, 46:89–94 (1986)], myelin basic protein gene control region which is active in oligodendrocyte cells in the brain [Readhead et al., Cell, 48:703–712 (1987)], myosin light chain-2 gene control region which is active in skeletal muscle [Sani, Nature, 314:283–286 (1985)], and gonadotropic releasing hormone gene control region which is active in the hypothalamus [Mason et al., Science, 234:1372–1378 (1986)].

Expression vectors containing a nucleic acid encoding a tankyrase of the invention can be identified by many means including by four general approaches: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding a tankyrase is inserted within the "selection marker" gene sequence of the vector, recombinants containing the tankyrase insert can be identified by the absence of the tankyrase gene function. In the fourth approach, recombinant expression vectors can be identified by assaying for the activity, biochemical, or immunological characteristics of the gene product expressed by the recombinant, provided that the expressed protein assumes a functionally active conformation, i.e., the ability of tankyrase to bind TRF1.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col E1, pCR1, pBR322, pMal-C2, pET, pGEX [Smith et al., Gene, 67:31–40 (1988)], pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the $2\mu$ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, XbaI, EcoR1, NotI, XmaIII, BglII, and PstI cloning site; Invitrogen), pVL1392 (BglII, PstI, NotI, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedrin initiation codon; Invitrogen(195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, Current Protocols in Molecular Biology, 16.12 (1991). Alternatively, a glutamine synthetase/methionine sulfoximine co-amplification vector, such as pEE14 (HindIII, XbaI, SmaI, SbaI, EcoRI, and BclI cloning site, in which the vector expresses glutamine synthase and the cloned gene; Celltech). In another embodiment, a vector that directs episomal expression under control of Epstein Barr Virus (EBV) can be used, such as pREP4 (BamH1, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamH1, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEB-VHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (SmaI cloning site, TK- and β-gal selection), pMJ601 (SalI, SmaI, AflI, NarI, BspMII, BamHI, ApaI, NheI, SacII, KpnI, and HindIII cloning site; TK- and β-gal selection), and pTKgptF1S (EcoRI, PstI, SalI, AccI, HindII, SbaI, BamHI, and Hpa cloning site, TK or XPRT selection).

Yeast expression systems can also be used according to the invention to express the tankyrase protein. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with Pro-Bond resin and cleaved with enterokinase; Invitrogen), to mention just two, can be employed according to the invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce an non-glycosylated core protein product. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, the tankyrase activity. Furthermore, different vector/host expression systems may affect processing reactions, such as proteolytic cleavages, to a different extent.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter [see, e.g., Wu et al., *J. Biol. Chem.* 267:963–967 (1992); Wu and Wu, *J. Biol. Chem.*, 263:14621–14624 (1988); Hartmut et al., Canadian Patent Application No. 2,012,311, filed Mar. 15, 1990).

Gene Therapy and Transgenic Vectors

A gene encoding a tankyrase or derivative thereof, including an inactive derivative can be introduced either in vivo, ex vivo, or in vitro in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred.

Defective virus is not infective after introduction into a cell. Use of defective viral vectors allows for administration to cells in a specific, localized area, without concern that the vector can infect other cells. For example, in the treatment of ataxia telangiectasia, T lymphocytes can be specifically targeted. Examples of particular vectors include, but are not limited to, a defective herpes virus I (HSV1) vector [Kaplitt et al., *Molec. Cell. Neurosci.*, 2:320–330 (1991)], an attenuated adenovirus vector, such as the vector described by Stratford-Perricaudet et al. [*J. Clin. Invest.*, 90:626–630 (1992)], and a defective adeno-associated virus vector [Samulski et al.,*J. Virol.*, 61:3096–3101 (1987); Samulski et al., *J. Virol.*, 63:3822–3828 (1989)].

Preferably, for in vitro administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors [see, e.g., Wilson, *Nature Medicine,* (1995)]. In addition, it is advantageous to employ a viral vector that is engineered to express a minimal number of antigens.

In another embodiment the gene can be introduced in a retroviral vector, e.g., as described in Anderson et al., U.S. Pat. No. 5,399,346; Mann et al., *Cell,* 33:153 (1983); Temin et al., U.S. Pat. No. 4,650,764; Temin et al., U.S. Pat. No. 4,980,289; Markowitz et al., J. Virol., 62:1120 (1988); Temin et al., U.S. Pat. No. 5,124,263; International Patent Publication No. WO 95/07358, published Mar. 16, 1995, by Dougherty et al.; and Kuo et al., *Blood,* 82:845 (1993).

Targeted gene delivery is described in International Patent Publication WO 95/28494, published October 1995.

Alternatively, the vector can be introduced by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Feigner, et. al., *Proc. Natl. Acad. Sci. U.S.A.,* 84:7413–7417 (1987); see Mackey, et al., *Proc. Natl. Acad. Sci. U.S.A.,* 85:8027–8031 (1988)]. The use of cationic lipids may promote encapsulation of negatively charged nucleic acids, and also promote fusion with negatively charged cell membranes [Felgner and Ringold, *Science,* 337:387–388 (1989)]. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting [see Mackey, et. al., 1988, supra]. Targeted peptides, e.g., hormones or neurotransmitters, and proteins such as antibodies, or non-peptide molecules could be coupled to liposomes chemically.

It is also possible to introduce the vector as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al.,*J. Biol. Chem.,* 267:963–967 (1992); Wu and Wu, *J. Biol. Chem.,* 263:14621–14624 (1988); Hartmut et al., Canadian Patent Application No.2, 012,311, filed Mar. 15, 1990].

In a further embodiment, the present invention provides for co-expression of tankyrase and a TRF1 and/or a TRF1 enhancing gene under control of a specific DNA recognition sequence by providing a gene therapy expression vector comprising a tankyrase coding gene, and a TRF1 coding gene and/or a TRF1 enhancing gene under control of, inter alia, a TRF1 regulatory sequence. In one embodiment, these elements are provided on separate vectors.

General Protein Purification Procedures

Initial steps for purifying the tankyrase of the present invention can include salting in or salting out, such as in ammonium sulfate fractionations; solvent exclusion fractionations, e.g., an ethanol precipitation; detergent extractions to free membrane bound proteins using such detergents as TRITON X-100, TWEEN-20 etc.; or high salt extractions. Solubilization of proteins may also be achieved using aprotic solvents such as dimethyl sulfoxide and hexamethylphosphoramide. In addition, high speed ultracentrifugation may be used either alone or in conjunction with other extraction techniques.

Generally good secondary isolation or purification steps include solid phase absorption using calcium phosphate gel or hydroxyapatite; or solid phase binding. Solid phase binding may be performed through ionic bonding, with either an anion exchanger, such as diethylaminoethyl (DEAE), or diethyl [2-hydroxypropyl] aminoethyl (QAE) SEPHADEX or cellulose; or with a cation exchanger such as carboxymethyl (CM) or sulfopropyl (SP) SEPHADEX or cellulose. Alternative means of solid phase binding includes the exploitation of hydrophobic interactions e.g., the using of a solid support such as phenylSepharose and a high salt buffer; affinity-binding, using, e.g., placing the N-terminal acidic domain of TRF1 on an activated support; immuno-binding, using e.g., an antibody to a tankyrase bound to an activated support; as well as other solid phase supports including those that contain specific dyes or lectins etc. A further solid phase support technique that is often used at the end of the purification procedure relies on size exclusion, such as SEPHADEX and SEPHAROSE gels, or pressurized or centrifugal membrane techniques, using size exclusion membrane filters.

Solid phase support separations are generally performed batch-wise with low-speed centrifugations or by column chromatography. High performance liquid chromatography (HPLC), including such related techniques as FPLC, is presently the most common means of performing liquid chromatography. Size exclusion techniques may also be accomplished with the aid of low speed centrifugation.

In addition size permeation techniques such as gel electrophoretic techniques may be employed. These techniques are generally performed in tubes, slabs or by capillary electrophoresis.

Almost all steps involving protein purification employ a buffered solution. Unless otherwise specified, generally 25–100 mM concentrations of buffer salts are used. Low concentration buffers generally imply 5–25 mM concentrations. High concentration buffers generally imply concentrations of the buffering agent of between 0.1–2M concentrations. Typical buffers can be purchased from most biochemical catalogues and include the classical buffers such as Tris, pyrophosphate, monophosphate and diphosphate and the Good buffers [Good, N. E., et al., *Biochemistry*, 5:467 (1966); Good, N. E. and Izawa, S., *Meth. Enzymol.*, 24B:53 (1972); and Fergunson, W. J. and Good, N. E., *Anal. Biochem.*, 104:300 (1980) such as Mes, Hepes, Mops, tricine and Ches.

Materials to perform all of these techniques are available from a variety of sources such as Sigma Chemical Company in St. Louis, Mo.

Antibodies to the Tankyrases

According to the present invention, the tankyrase or tankyrase-related proteins as produced by a recombinant source, or through chemical synthesis, or a tankyrase or tankyrase-related protein isolated from natural sources; and derivatives or analogs thereof, including fusion proteins, may be used as an immunogen to generate antibodies that recognize the tankyrase or tankyrase-related protein, as exemplified below. Such antibodies include but are not limited to polyclonal, monoclonal, chimeric, single chain, Fab fragments, and a Fab expression library. The anti-tankyrase antibodies of the invention may be cross reactive, that is, they may recognize a tankyrase derived from a different source. Polyclonal antibodies have greater likelihood of cross reactivity. Alternatively, an antibody of the invention may be specific for a single form of a tankyrase, such as the tankyrase having an amino acid sequence of SEQ ID NO:2.

Various procedures known in the art may be used for the production of polyclonal antibodies to tankyrase or derivative or analog thereof. For the production of antibody, various host animals can be immunized by injection with the tankyrase, or a derivative (e.g., or fusion protein) thereof, including but not limited to rabbits, mice, rats, sheep, goats, etc. In one embodiment, the tankyrase can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the tankyrase, or analog, or derivative thereof, any technique that provides for the production of antibody molecules by continuous cell lines in culture may be used. These include but are not limited to the hybridoma technique originally developed by Kohler and Milstein [*Nature*, 256:495–497 (1975)], as well as the trioma technique, the human B-cell hybridoma technique [Kozbor et al., *Immunology Today*, 4:72 (1983); Cote et al., *Proc. Natl. Acad. Sci. U.S.A.*, 80:2026–2030 (1983)], and the EBV-hybridoma technique to produce human monoclonal antibodies [Cole et al., in *Monoclonal Antibodies and Cancer Therapy*, Alan R. Liss, Inc., pp. 77–96 (1985)]. In an additional embodiment of the invention, monoclonal antibodies can be produced in germ-free animals utilizing recent technology [PCT/US90/02545]. In fact, according to the invention, techniques developed for the production of "chimeric antibodies" [Morrison et al., *J. Bacteriol.*, 159:870 (1984); Neuberger et al., *Nature*, 312:604–608 (1984); Takeda et al., *Nature*, 314:452–454 (1985)] by splicing the genes from a mouse antibody molecule specific for a tankyrase together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies [U.S. Pat. Nos. 5,476,786 and 5,132,405 to Huston; U.S. Pat. No. 4,946,778] can be adapted to produce e.g., tankyrase-specific single chain antibodies. An additional embodiment of the invention utilizes the techniques described for the construction of Fab expression libraries [Huse et al., *Science*, 246:1275–1281 (1989)] to allow rapid and easy identification of monoclonal Fab fragments with the desired specificity for an A-tankyrase, or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of tankyrase, one may assay generated hybridomas for a product which binds to the tankyrase fragment containing such epitope and choose those which do not cross-react with tankyrase. For selection of an antibody specific to a tankyrase from a particular source, one can select on the basis of positive binding with tankyrase expressed by or isolated from that specific source.

The foregoing antibodies can be used in methods known in the art relating to the localization and activity of the tankyrase, e.g., for Western blotting, imaging tankyrase in situ, measuring levels thereof in appropriate physiological samples, etc. using any of the detection techniques mentioned herein or known in the art.

In a specific embodiment, antibodies that agonize or antagonize the activity of tankyrase can be generated. Such antibodies can be tested using the assays described infra for identifying ligands.

Labels

The tankyrases of the present invention, antibodies to tankyrases, nucleic acids that hybridize to SEQ ID NO:1 (e.g. probes), as well as nucleic acids that comprise the specific nucleotide sequences that tankyrases bind, can all be labeled. Suitable labels include enzymes, fluorophores (e.g., fluorescein isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker.

In the instance where a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. Such labels may also be appropriate for the nucleic acid probes used in binding studies with tankyrase. In the instance where the label is an enzyme, detection may be accomplished by any of the presently utilized calorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell er al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Imnunoassay ELISA and EMIT in *Methods in Enzymology*, 70:419439 (1980) and in U.S. Pat. No. 4,857,453.

Suitable enzymes include, but are not limited to, alkaline phosphatase and horseradish peroxidase.

In addition, a tankyrase or fragment thereof can be modified to contain a marker protein such as green fluorescent protein as described in U.S. Pat. No. 5,625,048 filed Apr. 29, 1997 and WO 97/26333, published Jul. 24, 1997 each of which are hereby incorporated by reference herein in their entireties.

Other labels for use in the invention include magnetic beads or magnetic resonance imaging labels.

In another embodiment, a phosphorylation site can be created on an antibody of the invention for labeling with $^{32}P$, e.g., as described in European Patent No. 0372707 (application No. 89311108.8) by Sidney Pestka, or U.S. Pat. No. 5,459,240, issued Oct. 17, 1995 to Foxwell et al.

As exemplified herein, proteins, including antibodies, can be labeled by metabolic labeling. Metabolic labeling occurs during in vitro incubation of the cells that express the protein in the presence of culture medium supplemented with a metabolic label, such as [35S]-methionine or [$^{32}$P]-orthophosphate. In addition to metabolic (or biosynthetic) labeling with [$^{35}$S]-methionine, the invention further contemplates labeling with [$^{14}$C]-amino acids and [$^{3}$H]-amino acids (with the tritium substituted at non-labile positions).

Gene Therapy and Transgenic Vectors

In one embodiment, a gene encoding a tankyrase or structural/functional domain thereof is introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, any tissue can be specifically targeted. Examples of particular vectors include, but are not limited to, a defective herpes virus 1 (HSV1) vector [Kaplitt et al., *Molec. Cell. Neurosci.* 2:320–330 (1991)], an attenuated adenovirus vector, such as the vector described by Stratford-Perricaudet et al. [J. Clin. Invest. 90:626–630 (1992)], and a defective adeno-associated virus vector [Samulski et al., *J. Virol.* 61:3096–3101 (1987); Samulski et al., *J. Virol.* 63:3822–3828 (1989)].

Preferably, for in vitro administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-γ (IFN-γ), or anti-CD4 antibody, can be administered to block humoral or cellular immune responses to the viral vectors [see, e.g., Wilson, *Nature Medicine* (1995)]. In addition, it is advantageous to employ a viral vector that is engineered to express a minimal number of antigens.

In another embodiment the gene can be introduced in a retroviral vector, e.g., as described in Anderson et al., U.S. Pat. No. 5,399,346; Mann et al., 1983, *Cell* 33:153; Temin et al., U.S. Pat. No. 4,650,764; Temin et al., U.S. Pat. No. 4,980,289; Markowitz et al., 1988, *J. Virol.* 62:1120; Temin et al., U.S. Pat. No. 5,124,263; International Patent Publication No. WO 95/07358, published Mar. 16, 1995, by Dougherty et al.; and Kuo et al., 1993, *Blood* 82:845.

Targeted gene delivery is described in International Patent Publication WO 95/28494, published October 1995.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner, et. al., *Proc. Natl. Acad. Sci. U.S.A.* 84:7413–7417 (1987); see Mackey, et al., *Proc. Natl. Acad. Sci. U.S.A.* 85:8027–8031

(1988)]. The use of cationic lipids may promote encapsulation of negatively charged nucleic acids, and also promote fusion with negatively charged cell membranes [Felgner and Ringold, *Science* 337:387–388 (1989)]. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting [see Mackey, et. al., supra]. Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., *J. Biol. Chem.* 267:963–967 (1992); Wu and Wu, *J. Biol. Chem.* 263:14621–14624 (1988); Hartmut et al., Canadian Patent Application No. 2,012,311, filed Mar. 15, 1990].

In a preferred embodiment of the present invention, a gene therapy vector as described above employs a transcription control sequence operably associated with the sequence for the tankyrase inserted in the vector. That is, a specific expression vector of the present invention can be used in gene therapy.

Such an expression vector is particularly useful to regulate expression of a therapeutic tankyrase gene. In one embodiment, the present invention contemplates constitutive expression of the tankyrase gene, even if at low levels. In general, see U.S. Pat. No. 5,399,346 to Anderson et al.

Antisense, Gene Targeting and Ribozymes

The functional activity of tankyrase can be evaluated transgenically. In this respect, a transgenic mouse model can be used. The tankyrase gene can be used in complementation studies employing transgenic mice. Transgenic vectors, including viral vectors, or cosmid clones (or phage clones) corresponding to the wild type locus of candidate gene, can be constructed using the isolated tankyrase gene. Cosmids may be introduced into transgenic mice using published procedures [Jaenisch, *Science*, 240:1468–1474 (1988)]. In a genetic sense, the transgene acts as a suppressor mutation.

Alternatively, a transgenic animal model can be prepared in which expression of the tankyrase gene is disrupted. Gene expression is disrupted, according to the invention, when no functional protein is expressed. One standard method to evaluate the phenotypic effect of a gene product is to employ knock-out technology to delete a gene as described in U.S. Pat. No. 5,464,764, Issued Nov. 7, 1995; and U.S. Pat. No. 5,777,195, Issued Jul. 7, 1998 (both of which are hereby incorporated by reference herein in their entireties.)

The present invention also extends to the preparation of antisense nucleotides and ribozymes that may be used to interfere with the expression of tankyrase at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule [See Weintraub, *Sci. Amer.* 262:40–46 (1990); Marcus-Sekura, *Nucl. Acid Res,* 15: 5749–5763 (1987); Marcus-Sekura *Anal.Biochem.,* 172:289–295 (1988); Brysch et al., *Cell Mol. Neurobiol.,* 14:557–568 (1994)]. Preferably, the antisense molecule employed is complementary to a substantial portion of the mRNA. In the cell, the antisense molecule hybridizes to that mRNA, forming a double stranded molecule. The cell does not translate an mRNA in this double-stranded form. Therefore, antisense nucleic acids interfere with the expression of mRNA into protein. Preferably a DNA antisense nucleic acid is employed since such an RNA/DNA duplex is a preferred substrate for RNase H. Oligomers of greater than about fifteen nucleotides and molecules that hybridize to the AUG initiation codon will be particularly efficient, though larger molecules that are essentially complementary to the entire mRNA are more likely to be effective. Antisense methods have been used to inhibit the expression of many genes in vitro [Marcus-Sekura, *Anal.Biochem.,* 172:289–295 (1988); Hambor et al., *Proc. Natl. Acad. Sci. U.S.A.* 85:4010–4014 (1988)] and in situ [Arima et al., *Antisense Nucl. Acid Drug Dev.* 8:319–327 (1998); Hou et al., *Antisense Nucl. Acid Drug Dev.* 8:295–308 (1998); U.S. Pat. No. 5,726,020, Issued Mar. 10, 1998; and U.S. Pat. No. 5,731,294, Issued Mar. 24, 1998, all of which are incorporated by reference in their entireties].

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these ribozymes, researchers have been able to engineer molecules that recognize specific nucleotide sequences in an RNA molecule and cleave it [Cech, *JAMA,* 260:3030–3034 (1988); Cech, *Biochem. Intl,* 18:7–14 (1989)]. Because they are sequence-specific, only mRNAs with particular sequences are inactivated.

Investigators have identified two types of ribozymes, Tetrahymena-type and "hammerhead"-type [Haselhoff and Gerlach, *Nature* 334:585–591 (1988)]. Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences described herein may thus be used to prepare antisense molecules against, and ribozymes that cleave mRNAs for tankyrase and their ligands.

Kits

In a further embodiment of this invention, commercial test kits suitable for use by a medical specialist may be prepared to determine the presence or absence of predetermined telomere-binding activity or predetermined telomere lengthening activity capability in suspected target cells. In accordance with the testing techniques discussed above, one class of such kits will contain at least the labeled tankyrase or its binding partner, for instance an antibody specific thereto, and directions, of course, depending upon the method selected, e.g., "competitive", "sandwich", "DASP", and the like. The kits may also contain peripheral reagents such as buffers, stabilizers, etc. and /or directions.

Drug Screens

In addition to rational design of agonists and antagonists based on the structure of tankyrase the present invention further contemplates an alternative method for identifying specific antagonists or agonists using various screening assays known in the art.

Accordingly any screening technique known in the art can be used to screen for agonists or antagonists to tankyrase. The present invention contemplates screens for small molecule ligands or ligand analogs and mimics, as well as screens for natural ligands that bind to and agonize or antagonize tankyrase in vivo. For example, natural products libraries can be screened using assays of the invention for molecules that agonize or antagonize tankyrase activity.

For example, the present invention provides methods of identifying agents that modulate the poly (ADP-ribose) polymerase activity of the tankyrases of the present invention. In a particular embodiment, the poly (ADP-ribose) polymerase activity is determined using α-$^{32}$PNAD$^+$, a protein substrate for the tankyrase (such as a histone, or TRF1, or fragment thereof), a tankyrase (or a fragment thereof containing an active PARP domain) in the presence and absence of potential agonists and/or antagonists. The PARP activity can be determined as a function of the amount of $^{32}$P labeled protein substrate generated. Alternatively, cold NAD$^+$ can be used and the labeled protein substrate can be determined using an antibody that is specific for PARP labeled proteins. In one embodiment, the protein substrate is placed on a nitrocellular filter and the assay is an activity blot [Simonin et al., *J. Biol. Chem.*, 265:19249–19256 (1990)]. In another embodiment the labeled protein substrate is precipitated (e.g. by trichloroacetic) and/or placed on an SDS gel following a solution assay [Simonin et al., *J. Biol. Chem.*, 268:13454–13461 (1993)].

Knowledge of the primary sequence of tankyrase and the similarity of several domains with those contained in other proteins, can also provide clue as the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" [Scott and Smith, 1990, *Science* 249:386–390 (1990); Cwirla, et al., *Proc. Natl. Acad. Sci.*, 87:6378–6382 (1990); Devlin et al., *Science*, 249:404–406 (1990)], very large libraries can be constructed (10$^6$–10$^8$ chemical entities). A second approach uses primarily chemical methods, of which the Geysen method [Geysen et al., *Molecular Immunology* 23:709–715 (1986); Geysen et al. *J. Immunologic Method* 102:259–274 (1987)] and the method of Fodor et al. [*Science* 251:767–773 (1991)] are examples. Furka et al. [14th *International Congress of Biochemistry, Volume 5*, Abstract FR:013 (1988); Furka, *Int. J. Peptide Protein Res.* 37:487–493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested as agonists or antagonists.

In another aspect, synthetic libraries [Needels et al., *Proc. Natl. Acad. Sci. USA* 90:10700–4 (1993); Ohlmeyer et al., *Proc. Natl. Acad. Sci. USA* 90:10922–10926 (1993); Lam et al., International Patent Publication No. WO 92/00252; Kocis et al., International Patent Publication No. WO 9428028, each of which is incorporated herein by reference in its entirety], and the like can be used to screen for ligands to the tankyrase according to the present invention.

Alternatively, assays for binding of soluble ligand to cells that express recombinant forms of the tankyrase can be performed. The soluble ligands can be provided readily as recombinant or synthetic polypeptides.

The screening can be performed with recombinant cells that express a tankyrase, or fragment thereof, e.g. the portion of tankyrase required for binding TRF1 or alternatively, using purified protein, e.g., produced recombinantly, as described above. For example, the ability of labeled, soluble or solubilized tankyrase to bind TRF1 can be used to screen libraries, as described in the foregoing references.

In one such example, a phage library can be employed. Phage libraries have been constructed which when infected into host *E. coli* produce random peptide sequences of approximately 10 to 15 amino acids [Parmley and Smith, *Gene*, 73:305–318 (1988), Scott and Smith, *Science*, 249:386–249 (1990)]. Specifically, the phage library can be mixed in low dilutions with permissive *E. coli* in low melting point LB agar which is then poured on top of LB agar plates. After incubating the plates at 37° C. for a period of time, small clear plaques in a lawn of *E. coli* will form which represents active phage growth and lysis of the *E. coli*. A representative of these phages can be absorbed to nylon filters by placing dry filters onto the agar plates. The filters can be marked for orientation, removed, and placed in washing solutions to block any remaining absorbent sites. The filters can then be placed in a solution containing, for example, a radioactive fragment of tankyrase containing the TRF1 binding domain. After a specified incubation period, the filters can be thoroughly washed and developed for autoradiography. Plaques containing the phage that bind to the radioactive TRF1 binding domain of tankyrase can then be identified. These phages can be further cloned and then retested for their ability to hinder the binding of tankyrase to TRF1, for example. Once the phages have been purified, the binding sequence contained within the phage can be determined by standard DNA sequencing techniques. Once the DNA sequence is known, synthetic peptides can be generated which represents these sequences.

It an alternative embodiment, the radioactive tankyrase fragment can contain the PARP-related domain. Plaques containing the phage that bind to the radioactive PARP-related domain can be identified, further cloned and retested for their ability to hinder the PARP activity of tankyrase. Again, once the phages have been purified, the binding sequence contained within the phage can be determined by standard DNA sequencing techniques. Once the DNA sequence is known, synthetic peptides can be generated which represents these sequences.

These peptides can be tested, for example, for their ability to interfere with tankyrase binding to TRF1, for example.

The effective peptide(s) can be synthesized in large quantities for use in in vivo models and eventually in humans to stimulate telomere elongation. It should be emphasized that synthetic peptide production is relatively non-labor intensive, easily manufactured, quality controlled and thus, large quantities of the desired product can be produced quite cheaply. Similar combinations of mass produced synthetic peptides have recently been used with great success [Patarroyo, *Vaccine*, 10:175–178 (1990)].

Alternatively, known inhibitors of PARP activity can be used to inhibit tankyrase activity, in situ and/or in vivo, thereby aiding in the modulation of telomere length. Telomere lengthening could be beneficial both in the extension of the life-span of non-tumor cells, as well as in the inhibition of tumor cell growth. Inhibitors of PARP activity are known in the art and include 3-aminobenzamide (3ab) and related inhibitors [Durkaczm et al., *Nature*, 283:593–596 (1980); Oikawa et al., Biochem. Biophys. Res. Commun., 97:1311–1316 (1980)].

Administration

According to the invention, the component or components of a therapeutic composition, e.g., a tankyrase or a tankyrase inhibitor such as 3-aminobenzamide and a pharmaceutically acceptable carrier, of the invention may be introduced parenterally, transmucosally, e.g., orally, nasally, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration.

In a preferred aspect, a tankyrase of the present invention can cross cellular or nuclear membranes, which would allow for intravenous or oral administration. Strategies are available for such crossing, including but not limited to, increasing the hydrophobic nature of a molecule; introducing the molecule as a conjugate to a carrier, such as a ligand to a specific receptor, targeted to a receptor; and the like.

The present invention also provides for conjugating targeting molecules to a tankyrase. "Targeting molecule" as used herein shall mean a molecule which, when administered in vivo, localizes to desired location(s). In various embodiments, the targeting molecule can be a peptide or protein, antibody, lectin, carbohydrate, or steroid. In one embodiment, the targeting molecule is a peptide ligand of a receptor on the target cell. In a specific embodiment, the targeting molecule is an antibody. Preferably, the targeting molecule is a monoclonal antibody. In one embodiment, to facilitate crosslinking the antibody can be reduced to two heavy and light chain heterodimers, or the F(ab')$_2$ fragment can be reduced, and crosslinked to the tankyrase via the reduced sulfhydryl.

Antibodies for use as targeting molecule are specific for cell surface antigen. In one embodiment, the antigen is a receptor. For example, an antibody specific for a receptor on T lymphocyte receptor, can be used in the treatment of ataxia telangiectasia. This invention further provides for the use of other targeting molecules, such as lectins, carbohydrates, proteins and steroids.

In another embodiment, the therapeutic compound can be delivered in a vesicle, in particular a liposome [see Langer, *Science*, 249:1527–1533 (1990); Treat et al., in *Liposomes in the Therapy of Infectious Disease and Cancer*, Lopez-Berestein and Fidler (eds.), Liss: New York, pp. 353–365 (1989); Lopez-Berestein, ibid., pp. 317–327; see generally ibid.]. To reduce its systemic side effects, this may be a preferred method for introducing a tankyrase.

In yet another embodiment, the therapeutic compound can be delivered in a controlled release system. For example, the polypeptide may be administered using intravenous infusion, an implantable osmotic pump, a transdermal patch, liposomes, or other modes of administration. In one embodiment, a pump may be used [see Langer, supra; Sefton, *CRC Crit. Ref. Biomed. Eng.*, 14:201 (1987); Buchwald et al., *Surgery*, 88:507 (1980); Saudek et al., *N. Engl. J. Med.*, 321:574 (1989)]. In another embodiment, polymeric materials can be used [see *Medical Applications of Controlled Release*, Langer and Wise (eds.), CRC Press: Boca Raton, Fla. (1974); *Controlled Drug Bioavailability, Drug Product Design and Performance*, Smolen and Ball (eds.), Wiley: New York (1984); Ranger and Peppas, *J. Macromol. Sci. Rev. Macromol. Chem.*, 23:61 (1983); see also Levy et al., *Science*, 228:190 (1985); During et al., *Ann. Neurol.*, 25:351 (1989); Howard et al.,*J. Neurosurg.*, 71:105 (1989)]. In yet another embodiment, a controlled release system can be placed in proximity of the therapeutic target, i.e., the brain, thus requiring only a fraction of the systemic dose [see, e.g., Goodson, in *Medical Applications of Controlled Release*, supra, vol. 2, pp. 115–138 (1984)]. Preferably, a controlled release device is introduced into a subject in proximity of the site of inappropriate immune activation or a tumor. Other controlled release systems are discussed in the review by Langer [*Science*, 249:1527–1533 (1990)].

Pharmaceutical Compositions. In yet another aspect of the present invention, provided are pharmaceutical compositions of the above. Such pharmaceutical compositions may be for administration for injection, or for oral, pulmonary, nasal or other forms of administration. In general, comprehended by the invention are pharmaceutical compositions comprising effective amounts of a low molecular weight component or components, or derivative products, of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. See, e.g., Remington's Pharmaceutical Sciences, 18th Ed. [1990, Mack Publishing Co., Easton, Pa. 18042] pages 1435–1712 which are herein incorporated by reference. The compositions may be prepared in liquid form, or may be in dried powder, such as lyophilized form.

Oral Delivery. Contemplated for use herein are oral solid dosage forms, which are described generally in Remington's Pharmaceutical Sciences, 18th Ed. 1990 (Mack Publishing Co. Easton, Pa. 18042) at Chapter 89, which is herein incorporated by reference. Solid dosage forms include tablets, capsules, pills, troches or lozenges, cachets or pellets. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: *Modern Pharmaceutics* Edited by G. S. Banker and C. T. Rhodes Chapter 10, 1979, herein incorporated by reference. In general, the formulation will include a tankyrase (or chemically modified forms thereof) and inert ingredients which allow for protection against the stomach environment, and release of the biologically active material in the intestine.

Also specifically contemplated are oral dosage forms of the above derivatized component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. An example of such a moiety is polyethylene glycol.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the protein (or derivative) or by release of the biologically active material beyond the stomach environment, such as in the intestine.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Binders also may be used to hold the therapeutic agent together to form a hard tablet and include materials from natural products such as acacia, tragacanth, starch and gelatin.

An anti-frictional agent may be included in the formulation of the therapeutic to prevent sticking during the formulation process. Lubricants may be used as a layer between the therapeutic and the die wall. Glidants that might improve the flow properties of the drug during formulation and to aid rearrangement during compression also might be added. The glidants may include starch, talc, pyrogenic silica and hydrated silicoaluminate.

In addition, to aid dissolution of the therapeutic into the aqueous environment a surfactant might be added as a wetting agent. Additives which potentially enhance uptake of the protein (or derivative) are for instance the fatty acids oleic acid, linoleic acid and linolenic acid.

Nasal Delivery. Nasal delivery of a tankyrase or derivative thereof is also contemplated. Nasal delivery allows the passage of the protein to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

Transdermal administration. Various and numerous methods are known in the art for transdermal administration of a drug, e.g., via a transdermal patch. Transdermal patches are described in for example, U.S. Pat. No. 5,407,713, issued Apr. 18, 1995 to Rolando et al.; U.S. Pat. No. 5,352,456, issued Oct. 4, 1004 to Fallon et al.; U.S. Pat. No. 5,332,213 issued Aug. 9, 1994 to D'Angelo et al.; U.S. Pat. No. 5,336,168, issued Aug. 9, 1994 to Sibalis; U.S. Pat. No. 5,290,561, issued Mar. 1, 1994 to Farhadieh et al.; U.S. Pat. No. 5,254,346, issued Oct. 19, 1993 to Tucker et al.; U.S. Pat. No. 5,164,189, issued Nov. 17, 1992 to Berger et al.; U.S. Pat. No. 5,163,899, issued Nov. 17, 1992 to Sibalis; U.S. Pat. Nos. 5,088,977 and 5,087,240, both issued Feb. 18, 1992 to Sibalis; U.S. Pat. No. 5,008,110, issued Apr. 16, 1991 to Benecke et al.; and U.S. Pat. No. 4,921,475, issued May 1, 1990 to Sibalis, the disclosure of each of which is incorporated herein by reference in its entirety.

It can be readily appreciated that a transdermal route of administration may be enhanced by use of a dermal penetration enhancer, e.g., such as enhancers described in U.S. Pat. No. 5,164,189 (supra), U.S. Pat. No. 5,008,110 (supra), and U.S. Pat. No. 4,879,119, issued Nov. 7, 1989 to Aruga et al., the disclosure of each of which is incorporated herein by reference in its entirety.

Pulmonary Delivery. Also contemplated herein is pulmonary delivery of the pharmaceutical compositions of the present invention. A pharmaceutical composition of the present invention is delivered to the lungs of a mammal while inhaling and traverses across the lung epithelial lining to the blood stream. Other reports of this include Adjei et al. [*Pharmaceutical Research,* 7:565–569 (1990); Adjei et al., *International Journal of Pharmaceutics,* 63:135–144 (1990) (leuprolide acetate); Braquet et al., *Journal of Cardiovascular Pharmacology,* 13(suppl. 5):143–146 (1989) (endothelin-1); Hubbard et al., *Annals of Internal Medicine,* Vol. III, pp. 206–212 (1989) ($\alpha$1-antitrypsin); Smith et al., *J. Clin. Invest.,* 84:1145–1146 (1989) ($\alpha$-1-proteinase); Oswein et al., "Aerosolization of Proteins", *Proceedings of Symposium on Respiratory Drug Delivery II,* Keystone, Colo., March, (1990) (recombinant human growth hormone); Debs et al., *J. Immunol.,* 140:3482–3488 (1988) (interferon-$\gamma$ and tumor necrosis factor alpha); Platz et al., U.S. Pat. No. 5,284,656 (granulocyte colony stimulating factor)]. A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. With regard to construction of the delivery device, any form of aerosolization known in the art, including but not limited to spray bottles, nebulization, atomization or pump aerosolization of a liquid formulation, and aerosolization of a dry powder formulation, can be used in the practice of the invention.

All such devices require the use of formulations suitable for the dispensing of pharmaceutical composition of the present invention (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified pharmaceutical composition of the present invention may also be prepared in different formulations depending on the type of chemical modification or the type of device employed.

Formulations suitable for use with a nebulizer, either jet or ultrasonic, will typically comprise pharmaceutical composition of the present invention (or derivative) dissolved in water at a concentration of about 0.1 to 25 mg of biologically active ingredients of a pharmaceutical composition of the present invention per mL of solution. The formulation may also include a buffer and a simple sugar (e.g., for stabilization and regulation of osmotic pressure of a pharmaceutical composition of the present invention). The nebulizer formulation may also contain a surfactant, to reduce or prevent surface induced aggregation of the pharmaceutical composition of the present invention caused by atomization of the solution in forming the aerosol.

The liquid aerosol formulations contain a pharmaceutical composition of the present invention and a dispersing agent in a physiologically acceptable diluent. The dry powder aerosol formulations of the present invention consist of a finely divided solid form of a pharmaceutical composition of the present invention and a dispersing agent. With either the liquid or dry powder aerosol formulation, the formulation must be aerosolized. That is, it must be broken down into liquid or solid particles in order to ensure that the aerosolized dose actually reaches the mucous membranes of the nasal passages or the lung. The term "aerosol particle" is used herein to describe the liquid or solid particle suitable for nasal or pulmonary administration, i.e., that will reach the mucous membranes. Other considerations, such as construction of the delivery device, additional components in the formulation, and particle characteristics are important. These aspects of nasal or pulmonary administration of a drug are well known in the art, and manipulation of formulations, aerosolization means and construction of a delivery device require at most routine experimentation by one of ordinary skill in the art.

Often, the aerosolization of a liquid or a dry powder formulation for inhalation into the lung will require a propellent. The propellent may be any propellant generally used in the art. Specific non-limiting examples of such useful propellants are a chlorofluorocarbon, a hydrofluorocarbon, a hydrochlorofluorocarbon, or a hydrocarbon, including trifluoromethane, dichlorodifluoromethane, dichlorotetrafluoroethanol, and 1,1,1,2-tetrafluoroethane, or combinations thereof.

Systems of aerosol delivery, such as the pressurized metered dose inhaler and the dry powder inhaler are disclosed in Newman, S. P., *Aerosols and the Lung,* Clarke, S. W. and Davia, D. editors, pp 197–22 and can be used in connection with the present invention.

In general, as described in detail infra, pharmaceutical composition of the present invention is introduced into the subject in the aerosol form in an amount between about 0.01 mg per kg body weight of the mammal up to about 1 mg per kg body weight of said mammal. In a specific embodiment, the dosage is administered as needed. One of ordinary skill in the art can readily determine a volume or weight of aerosol corresponding to this dosage based on the concentration of pharmaceutical composition of the present invention in an aerosol formulation of the invention.

Liquid Aerosol Formulations. The present invention provides aerosol formulations and dosage forms. In general such dosage forms contain a pharmaceutical composition of the present invention in a pharmaceutically acceptable diluent. Pharmaceutically acceptable diluents include but are not limited to sterile water, saline, buffered saline, dextrose solution, and the like.

The formulation may include a carrier The carrier is a macromolecule which is soluble in the circulatory system and which is physiologically acceptable where physiological acceptance means that those of skill in the art would accept injection of said carrier into a patient as part of a therapeutic regime. The carrier preferably is relatively stable in the circulatory system with an acceptable plasma half life for clearance. Such macromolecules include but are not limited to Soya lecithin, oleic acid and sorbitan trioleate, with sorbitan trioleate preferred.

The formulations of the present embodiment may also include other agents useful for pH maintenance, solution stabilization, or for the regulation of osmotic pressure.

Aerosol Dry Powder Formulations. It is also contemplated that the present aerosol formulation can be prepared as a dry powder formulation comprising a finely divided powder form of pharmaceutical composition of the present invention and a dispersant.

Formulations for dispensing from a powder inhaler device will comprise a finely divided dry powder containing pharmaceutical composition of the present invention (or derivative) and may also include a bulking agent, such as lactose, sorbitol, sucrose, or mannitol in amounts which facilitate dispersal of the powder from the device, e.g., 50 to 90% by weight of the formulation. The pharmaceutical composition of the present invention (or derivative) should most advantageously be prepared in particulate form with an average particle size of less than 10 mm (or microns), most preferably 0.5 to 5 mm, for most effective delivery to the distal lung.

In a further aspect, recombinant cells that have been transformed with the tankyrase gene and that express high levels of the polypeptide can be transplanted in a subject in need of tankyrase. Preferably autologous cells transformed with tankyrase are transplanted to avoid rejection; alternatively, technology is available to shield non-autologous cells that produce soluble factors within a polymer matrix that prevents immune recognition and rejection.

Methods of Treatment, Methods of Preparing a Medicament. In yet another aspect of the present invention, methods of treatment and manufacture of a medicament are provided. Conditions alleviated or modulated by the administration of the present derivatives are those indicated above.

Dosages. For all of the above molecules, as further studies are conducted, information will emerge regarding appropriate dosage levels for treatment of various conditions in various patients, and the ordinary skilled worker, considering the therapeutic context, age and general health of the recipient, will be able to ascertain proper dosing.

A subject in whom administration of tankyrase is an effective therapeutic regiment is preferably a human, but can be any animal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The present invention may be better understood by reference to the following non-limiting Example, which is provided as exemplary of the invention. The following example is presented in order to more fully illustrate the preferred embodiments of the invention. It should in no way be construed, however, as limiting the broad scope of the invention.

EXAMPLE 1

Tankyrase. A PARP-Related Enzyme at Human Telomeres

Introduction

Human chromosome ends consist of tandom arrays of telomeric TTAGGG repeats bound to specific proteins [Bilaud et al., *Nature Gen.*, 17:236–239 (1997); Chong et al., *Science*, 270:1663–1667 (1995); Broccoli et al., *Nature Gen.*, 17:231–235 (1997)]. Due to the inability of conventional DNA polymerases to replicate chromosome ends, telomeric sequences are lost at each cell division [Cooke and Smith, *Cold Spring Harbor Sym. Quant. Biol.*, LI:213–219 (1986); Harley et al., *Nature*, 345:458–460 (1990); Hastie et al., *Nature*, 346:866–868; reviewed in Harley, Telomeres and Ageing, In Telomeres (ed. Blackburn and Grieder) Cold Spring Harbor Press, 247–265]. In the germline and in immortalized cells and tumors, telomeric DNA can be maintained by telomerase, a reverse transcriptase that adds TTAGGG repeats onto 3' ends of chromosomes [reviewed in Greider, *Ann. Rev. Biochem.*, 65:337–365 (1996); Morin, *Seminars in Cell Dev. Biol.*, 7:5–15 (1996)]. In somatic cells, due to the low level or absence of telomerase, telomeres shorten by 50–200 basepairs per cell division. This programmed telomere shortening may be best viewed as a tumor suppressor mechanism that limits the growth potential of transformed cells [de Lange, *Science*, 279:333–335 (1998)]. In agreement, telomere length is strongly correlated with the proliferative capacity of normal human cells [Allsopp et al., *Proc. Natl. Acad of Sci. USA*, 89:10114–10118 (1992)], the catalytic subunit of telomerase (hTERT) is up-regulated in human tumors, and immortalized cells [Meyerson et al., *Cell*, 90:785–795 (1997); Nakamura et al., *Science*, 277:955–959 (1997)] and activation of telomerase in primary human cells results in the extension of cellular life-span beyond the scheduled senescence point [Bodnar et al., *Science*, 279:349–352 (1998); Vaziri and Benchimol, *Curr. Biol.*, 8:279–282 (1998)].

The only known protein components of mammalian telomeres are the TRF proteins, duplex TTAGGG repeat binding factors that are localized at telomeres in interphase and metaphase chromosomes [Zhong et al., *Mol. Cell. Biol.*, 13:4834–4943 (1992); Chong et al., *Science*, 270:1663–1667 (1995); Ludérus et al., *J. Cell Biol.*, 135:867–881 (1996); Broccoli et al., *Hum. Mol. Genetics*, 6:69–76 (1997); see Smith and de Lange, *Trends in Genetics*, 13:21–26 (1997) for review]. Human TRF1 (hTRF1) is a low-abundance activity found in nuclear extracts from all human cells and tissues and a similar activity is present in other vertebrates [Zhong et al., *Mol. Cell. Biol.*, 13:4834–4943 (1992); Chong et al., *Science*, 270:1663–1667 (1995)]. TRF2 (also referred to as orf2) was recently identified as a TRF1 homolog. [Bilaud et al., *Nucl. Acids Res.*, 24:1294–1303 (1996)]. While the function of the TRFs has not been fully established, similar duplex telomeric DNA binding activities in yeasts have been implicated in telomere length control, telomere stability, and telomeric silencing [reviewed in Shore, *Trends Gen.*, 10:408–412 (1994); Zakian, *Saccharomyces telomere: function, structure and replication*, Cold Spring Harbor Laboratory Press, Cold Spring Harbor, pp. 107–138 (1995a); see also McEachern and Blackburn, *Nature*, 376:403–409 (1995); Krauskopf and Blackburn, *Nature*, 383:354–357 (1996)].

TRF1 has DNA binding properties in vitro that are consistent with its presence along the double-stranded telomeric repeat array at chromosome ends. TRF1 binds efficiently to arrays of duplex TTAGGG repeats, irrespective of the presence of a DNA terminus [Zhong et al., *Mol. Cell. Biol.*, 13:4834–4943 (1992)]. Single-stranded telomeric DNA is not an effective TRF1 substrate and neither are heterologous telomeric sequences, such as double-stranded arrays of TTGGGG, TTAGGC, TTTAGGG, TTAGGGGG, and TAGGG repeats [Zhong et al., *Mol. Cell. Biol.*, 13:4834–4943 (1992); Hanish et al. *Proc. Natl. Acad. Sci. USA*, 91:8861–8865 (1994); Chong et al., *Science*, 270:1663–1667 (1995)]. This sequence specificity of TRF1 matches the sequence requirements for de novo telomere formation in human cells, suggesting that the TRF proteins are involved in this process [Hanish et al. *Proc. Natl. Acad. Sci. USA*, 91:8861–8865 (1994)].

A novel human telomeric protein, tankyrase, has been isolated, as described herein, that binds TRF1 and is located at human telomeres throughout the cell cycle. Tankyrase was isolated using a two-hybrid screen with TRF1 on the premise that telomere length homeostasis involves additional TRF1- and telomerase-associated proteins. The domain structure of tankyrase indicates a mechanism by which TRF1 might regulate telomerase.

Methods

Tankyrase cDNA cloning: The full-length tankyrase cDNA TT20 contains a 4134 nucleotide (nt) insert in the vector pBKCMV. It has an ORF of 1327 amino acids starting with CGAAG<u>ATG</u> initiating codon (6 nt in from the 5' end), which is favorable for initiating translation. Two other overlapping isolates TT6 and TT18, which contained 23 nt 5' of the end of TT20, had an in-frame stop codon upstream of the initiating ATG, confirming the translational start site. The 3' end of TT20 contained a stop codon followed by 146 nt of 3' untranslated sequence.

The TT20 cDNA was isolated in several steps. First, a PCR product (encoding amino acids 973–1163 of SEQ ID NO:2) made from TR1L4 was used as a probe to screen a HeLa cell cDNA library. Two overlapping cDNAs, 32 and 21, encompassing 8,901 nt were isolated. These clones encoded amino acids 235–1327 of SEQ ID NO:2. The 3' end had 5,539 nt of 3' untranslated sequence and a AATAAA polyadenylation site 19 nt upstream of a poly A stretch. The 5' end sequence was extended using the RACE procedure to yield a 514 nt clone RACE 4C (encoding amino acids 83–253 of SEQ ID NO:2). A continuous open reading frame (ORF) was constructed (RACE4C+32) and a PCR probe derived from this construct, encoding amino acids 183–303 of SEQ ID NO:2, was used to screen a human testis library (Stratagene) to isolate TT20 as described above.

Two other testis library isolates and TT9 were characterized. DNA sequence analysis indicated that they had the same 5' end as TT20. Restriction digest and nested PCR analysis indicated they were similar to TT20 along their length except each had an approximately 100 nt insertion; TT7, had an insertion after amino acid 640 of SEQ ID NO:2 (in ANK repeat 14) and TT9, insertion after amino acid 881 of SEQ ID NO:2 (in ANK repeat 21). Both insertions contained stop codons resulting in truncated proteins which were confirmed by in vitro translation.

Tankyrase expression constructs: FLAG-tankyrase-1 (encoding amino acids 337–1149 of SEQ ID NO:2) was constructed by cloning a PCR amplified fragment into the NotI-ApaI cloning sites of a modified pRc/CMV expression vector (Invitrogen) carrying a FLAG epitope 5' of the cloning sites. PCR was performed on plasmid TR1L-4 as template with 5' TTGCGGCCGCAGACGAACTCCTA-GAAGCT 3' as forward primer and 5' GCGGGCCCTATC-GAATGACATTGTATCTGT 3' as backward primer. FLAG-tankyrase (encoding amino acids 2–1327 of SEQ ID NO:2) was constructed in two steps. First, an intermediate construct CMV-IMC (encoding amino acids 2–182 SEQ ID NO:2) was made by cloning a PCR-amplified fragment into the NotI-ApaI cloning sites of the modified pRc/CMV vector described above. PCR was performed on plasmid TT20 as template with 5' TTGCGGCCGCGGCG-GCGTCGCGTCGCT 3' as forward primer and 5' TGCG-GCGTCCACCACGGT 3' as backward primer. The subsequent digestion cut the natural ApaI site at amino acid 182 of SEQ ID NO:2. Next an ApaI fragment (encoding amino acids 183–1327of SEQ ID NO:2, a stop codon, 146 nt of 3' untranslated sequence, and vector polylinker sequence) from TT20 was cloned into the ApaI site of CMV-IMC and screened for the correct orientation to yield FLAG-tankyrase.

Yeast two-hybrid analysis: TR1L-4 and TR1L-12 were isolated from a human liver two-hybrid cDNA library (Clontech) created in pGad10. The library was screened with human full length TRF1 cDNA fused to LexA (LexA-TRF1) [Bianchi et al., *EMBO J.*, 16:1785–1794 (1997)] in the yeast strain L40 as described [Hollenberg et al., *Mol. Cell Biol.*, 15:3813–3822 (1995)]. Two-hybrid analysis was performed as described by Bianchi et al. [*EMBO J.*, 16:1785–1794 (1997)]. β-galactosidase assays for the two-hybrid analysis was performed as described by Bianchi et al. [*EMBO J.*, 16:1785–1794 (1997)].

Anti-tankyrase antibodies: The Ank2 plasmid containing a sub-domain of tankyrase (encoding amino acids 973–1149 of SEQ ID NO:2) in the vector pET-22b(+) (Novagen) was expressed as a fusion protein in *E. coli*. The protein was isolated in inclusion bodies and used to immunize a rabbit (#465). The resulting immune serum, rabbit anti-tankyrase, 465, was affinity purified against Ank2 protein coupled to CnBr-activated SEPHAROSE (Sigma Biochemicals) using standard procedures [Harlow and Lane. Antibodies, A Laboratory Manual, Cold Spring Harbor Press, (1988)].

PARP assays were performed with baculovirus-derived tankyrase essentially as described in [Simonin et al 268:8529 (1993)] but without addition of DNA. To make baculovirus-derived protein, an N-terminally [His]$_6$-tagged fusion protein of human tankyrase was generated in the expression vector pFastBac HTb (Gibco BRL, Grand Island) and used to generate a recombinant plasmid in DH10Bac *E. coli*. The recombinant DNA was used to transfect SF21 insect cells and recombinant virus was isolated and amplified. Protein was purified as described for baculovirus-derived TRF1 [Bianchi et al., *EMBO J.* 16:1785 (1997)]. Samples containing tankyrase (0–4 μg) and TRF 1 (0–4 μg) [Bianchi et al., *EMBO J.* 16:1785 (1997)] were incubated for 30 minutes at 25° C. in 0.1 ml of assay buffer containing 50 mM Tris-HCl (pH 8.0), 4 mM Mg Cl$_2$, 0.2 mM dithiothreitol (DTT), 1.3 μM [$^{32}$P]NAD+ (4 μCi) and varying concentrations of unlabeled NAD+ (0–1 mM). Reactions were stopped by the addition of 20% trichloroacetic acid (TCA). Acid-insoluble proteins were collected by centrifugation, rinsed in 5% TCA, suspended in Laemmli loading buffer, and fractionated on SDS-PAGE. Proteins were visualized by Coomassie-Blue stain and autoradiography. For the immunoblot analysis reactions were performed the same way except that the [$^{32}$P]NAD+ was omitted. Samples were immunoblotted as described below, and probed with 10H, a mouse monoclonal antibody raised against poly(ADP-ribose) (1:250) [Kawamitsu et al., *Biochemistry* 23:3771 (1984)] followed by horseradish peroxidase-conjugated sheep antibody to mouse IgG (Amersham).

Northern blot: Northern blots (Clontech) were probed with the tankyrase cDNA isolated from TR1L-4 as described [Chong et al., *Science*, 270:1663–1667 (1995)].

Cell extracts and protein fractions: HeLaI cells were suspended directly in Laemmli loading buffer. For rat testis extracts, crude nuclei were isolated (after hypotonic lysis), extracted with 0.4 M KCl, pelleted and suspended in Laemmli buffer [Chong et al., *Science*, 270:1663–1667 (1995)]. Rat nuclei were prepared as described [Blobel and Potter, *Science*, 154:1662–1665 (1966)]. Nuclear envelopes were prepared according to [Mutanis et al., *J. Cell. Biol.*, 135:1451–1470 (1996)]. Salt-washed nuclear envelopes, prepared as in [Snow et al., *J. Cell Biol.*, 104:1143–1156 (1987)] were extracted with urea as described [Worman, *Proc. Natl. Acad. Sci. USA*, 85:8531–8534 (1988)].

Western and Northern blotting: Proteins samples were fractionated on SDS polyacrylamide gels, transferred to nitrocellulose electrophoretically, and blocked in 5% milk in PBS containing 0.1% Tween-20. Antibody incubations were in 1% milk in PBS containing 0.1% Tween-20. Blots were incubated with affinity purified rabbit anti-tankyrase (4 μg/ml), pre-immune serum from the anti-tankyrase rabbit (1:500) or affinity purified rabbit anti-TRF1 620.1 (1:50), followed by horseradish peroxidase-conjugated donkey anti-rabbit IgG (1:2,500). Bound antibody was detected using the enhanced chemiluminescence kit (Amersham). Northern blots (Clontech) were probed with the tankyrase cDNA isolated from TR1L-4 as described in Broccoli et al. [*Mol. Cell Biol.*, 16:3765–3772 (1996)].

For immunoblots, HeLa cells were suspended directly in Laemmli loading buffer and loaded at ~50,000 cells per lane. Crude nuclei were isolated from rat testis (after hypotonic lysis), extracted with 0.4 M KCl, pelleted and suspended in Laemmli buffer. In vitro translated tankyrase was generated using a coupled transcription/translation reticulocyte lysate system (from Promega). One μg of TT20 was incubated with T3 RNA polymerase under standard conditions and 10% of the reaction was loaded per lane. Protein samples were fractionated on SDS polyacrylamide gels, transferred to nitrocellulose, and blocked in 5% milk in phosphate-buffered saline (PBS) containing 0.1% Tween-20. Antibody incubations were in 1% Tween-20. Blots were first incubated with rabbit anti-tankyrase antibodies (4 μg/ml) or rabbit pre-immune serum (1:500) and then with horseradish peroxidase-conjugated donkey antibody to rabbit immunoglobulin G (IgG), (1:2,500), (from Amersham). Bound antibody was detected by enhanced chemiluminescence (Amersham).

For Immunoprecipitation analysis, 80 μg of tankyrase in 1 ml of buffer D [20 mM Hepes (pH 7.9) containing 100 mM KCl, 20% glycerol, 0.2 mM ethylenediaminetetraacetic acid (EDTA), 0.2 mM ethylene glycol-bis (β-aminoethyl ether)-N,N,N',N'-tetraacetic acid (EGTA), 1 mM DTT, 0.5 mM phenylmethylsulfonyl fluoride (PMSF), 0.1% NP40, 0.1% Triton X-100, and 1 mg BSA per ml] was precleared by incubation with an irrelevant rabbit serum at room temperature for 1 hour, followed by addition of protein G SEPHAROSE (Pharmacia). Non-specific antibody complexes and protein aggregates were removed by centrifugation and the supernatant was used for immunoprecipitation analysis. 0.5 ml of supernatant was incubated with 2 μg anti-tankyrase antibody or 2 μg preimmune IgG from the same rabbit [purified by affinity chromatography on protein G SEPHAROSE (Pharmacia)] for 1 hour at room temperature. Antigen-antibody complexes were collected on protein G beads, washed 3 times with buffer D and 2 times with 50 mM Tris-HCl pH 8.0. The beads were then assayed for PARP activity by addition of 20 μl containing 50 mM Tris-HCl (pH 8.0), 4 mM MgCl$_2$, 0.2 mM DTT, and 1.3 μM [$^{32}$P]NAD$^+$ (0.8 μCi). The reactions were incubated and processed as described above.

Gel-shift assays were performed using an end-labeled 142 bp HindIII-Asp718 fragment from plasmid pTH12 [Z. Zhong, et al, *Mol. Cell. Biol.* 12:4834 (1992)] containing 12 tandem TTAGGG repeats. Baculovirus-derived TRF1 (13 to 120 ng) [Bianchi et al. *EMBO J.* 16:1785 (1997)] was incubated for 30 minutes at room temperature in a 20 μl reaction containing 20 mM Hepes-KOH (pH 7.9), 100 mM KCL, 0.5 mM DTT, 5% glycerol, 0.1% NP40, 100 ng sheared *E. coli* DNA, 100 ng β-casein, and 1 ng of labeled probe. In some cases, reactions were supplemented with NAD$^+$ (0.2 mM) and baculovirus-derived human tankyrase (2.5 to 200 ng). Samples were fractionated on a 0.7% agarose gel run in 0.1×TBE (8.9 mM Tris-base, 8.9 mM Boric acid, and 0.2 mM EDTA) at 130 volts for 1 hour at room temperature. Gels were dried onto Whatman DE81 paper and autoradiographed.

Tankyrase protein was also detected by Western analysis in the following human cell lines: 293, transformed embryonic kidney cells, IMR90 and WI38, primary lung fibroblasts; WI38 VA13/2RA, immortalized lung fibroblasts; GM847, SV40 immortalized fibroblasts; Daudi and Raji, lymphoma; HT1080, fibrosarcoma; and MCF, breast adenocarcinoma. Several of these cell lines were found to express only the larger set of tankyrase mRNAs (6–10 kilobases) indicating that the 142 kD polypeptide can be expressed from one of these transcripts.

Transfection: HelaI cells were transfected by electroporation of FLAG-tankyrase or FLAG-tankyrase-1 and pcDNA3-hTRF1 cloned into the expression vector pcDNA3 (Invitrogen). Cells were grown for 16 hr and then processed for immunofluorescence or immunoprecipitation as described below.

Indirect immunofluorescence: HelaI or Hela1.2.11 cells, a subclone of HeLaI containing telomeres of more than 20 kb, were fixed with ice cold methanol at −20° C. for 10 min or 3.7% formaldehyde in PBS for 10 min followed by permeabilization with 0.5% NP40 in PBS for 10 min. For chromosome spreads, Hela1.2.11 cells were treated with colcemide (0.1 μg/ml, 60 min), harvested by trypsinization, hypotonically swollen in 10 mM Tris (pH7.4), 10 mM NaCl and 5 mM MgCl$_2$ and sedimented onto coverslips for 15 seconds at 3000 rpm in a Sorvall RT6000B tabletop centrifuge. Chromosomes were swollen for 15 min in 25% PBS, then fixed in 3.7% formaldehyde in 25% PBS for 10 min, followed by permeabilization with 0.5% NP40 in 25% PBS for 10 min. Samples were blocked with 1%BSA in PBS, followed by incubation with primary antibodies diluted in 1% BSA/PBS. Endogenous tankyrase was detected with affinity-purified rabbit anti-tankyrase 465 (1–4 μg/ml). FLAG-tankyrase was detected with the mouse monoclonal antibody M2 anti-FLAG (Eastman-Kodak) (2–10 μg/ml). Nuclear pore complex proteins were detected with a mouse monoclonal antibody 414 [Davis and Blobel, *Cell*, 45:699–709 (1986)] (supernatant, 1:100). Centrosomal proteins in untransfected cells were detected with mouse monoclonal antibodies to: NuMA1F1 [Compton et al., *J. Cell Biol.*, 112:1083–1097 (1991)], (ascites 1:100), centrin 20H5 [Sanders and Salisbury, *J. Cell Biol.*, 124:795–805 (1994)] (ascites 1:2000), and γ-tubulin (ascites 1:2000) (Sigma). In transfected cells γ-tubulin was detected with a rabbit anti-peptide antibody XGC-1–4 (1:2000). Endogenous TRF1 in Hela1.2.11 cells was detected with mouse polyclonal serum directed against full length TRF1 (1:10,000). TRF1 in HeLa cells was detected with rabbit anti-TRF1 antibody 371 [van Steensel and de Lange, *Nature*, 385:740–473 (1997)] (0.4 μg/ml) for untransfected cells and (0.04 μg/ml) for transfected cells. Primary antibodies were detected with FITC- or TRITC-conjugated donkey anti-mouse or rabbit antibodies (1:100) (Jackson Laboratories). DNA was stained with DAPI (0.2 μg/ml). Micrographs were recorded on a Zeiss Axioplan microscope with a Photometric CCD camera. Images were processed and merged using Adobe Photoshop. Immunolocalization analysis of cycling HeLa cells indicates additional subcellular locations for tankyrase.

Immunoprecipitation: Whole cell extracts were prepared from transfected HeLaI cells as described [van Steensel et al., *Cell*, 92:401–413 (1998)]. Proteins were immunoprecipitated overnight on ice by addition of anti-tankyrase antibodies 465 (1 μg/ml), anti-TRF1 antibody 371 (0.1 μg/ml) or an unrelated rabbit serum as a control. Antibody antigen complexes were collected on protein G beads and processed as described [Broccoli et al., *Nature Gen.*, 17:231–235 (1997)].

Immunoelectron microscopy: HelaI cells in tissue culture dishes were permeabilized for 15 seconds in 0.5% Triton X-100/PBS, washed 2× in PBS, fixed for 10 min in 3% formaldehyde/PBS and blocked in 1% BSA/PBS. Cells were incubated with affinity purified rabbit anti-tankyrase antibodies 465 (5 μg/ml), followed by 5 nm gold-conjugated anti rabbit antibodies. Samples were processed for thin sectioning and electron microscopic analysis as described [Pain et al., *Nature*, 347:444–449 (1990)].

Amino Acid Alignments: Alignment of the 24 ANK repeats is based upon a Megalign Clustal alignment (gap penalty 10, gap length penalty 10) of the tankyrase ANK repeat domain with the ANK repeat domains of human ankyrins 1 (Genbank #M28880), 2 (Genbank #X56958) and 3 (Genbank #U13616). Comparisons of the PARP-related and SAM domains of tankyrase with other proteins was done with Clustal W 1.6 (gap opening penalty 10, gap extension penalty 0.05).

Results

Isolation of tankyrase cDNA and analysis of its predicted primary structure: A yeast two-hybrid screen with human TRF1 as bait was performed. Upon screening 1×10$^7$ transformants of a human fetal liver two-hybrid library, 13 positives were obtained. 12 of these contained an identical 2.4 kb insert, designated TR1L-4 and one had a 1 kb insert, designated TR1L-12, which was contained within TR1L-4 (see FIG. 1A). DNA sequence analysis indicated that TR1L-4 was a partial cDNA. Conceptual translation of the cDNA revealed that it was a novel protein, although it contained 20 copies of the previously recognized ANK repeat motif (see below). A full length cDNA (SEQ ID NO:1), designated tankyrase (TRF1-interacting ankyrin), isolated from a human testis library, contained an open reading frame of 1327 amino acids (SEQ ID NO:2), predicted to encode a protein of 142 kD.

A schematic representation of the predicted primary structure of tankyrase is presented in FIG. 1A. The amino terminal HPS domain consists of homohistidine, proline and serine tracts. Proline rich sequences have been shown to serve as binding sites for SH3 domains. A striking feature is the central domain containing 24 ANK repeats, a 33 amino acid motif shown to mediate protein-protein interactions

[Bork, *Proteins*, 17:363–374 (1993); Michaely and Bennett, *Trends Cell Biol.*, 2:127–129 (1992)]. ANK repeats are found in multiple copies, typically 4 to 8, in a functionally diverse group of proteins that includes the ankyrins, a family of structural proteins that link integral membrane proteins to the underlying cytoskeleton [reviewed in Bennett, *J. Biol. Chem.*, 267:8703–8706 (1992)]. Ankryins are notable for containing an unusually high number (24) of ANK repeats.

Several observations suggest that tankyrase is not just an ANK-repeat containing protein, but rather, a new member of the ankyrin family. First, the ANK repeats in tankyrase and the ankryins shares characteristic features that distinguishes them from the ANK repeats found in other proteins, such as the presence of a hydrophobic amino acid at position 3 and an N or D at position 29 (FIG. 1B) [Peters and Lux, *Semin. Hematol.*, 30:85–118 (1993)]. Second, ankyrins consist of 24 (mostly perfect) 33 amino acid repeats with the exception of repeat 5, which is 29 amino acids. While tankyrase consists of more irregular repeats, its shortest repeat is also repeat 5, which is 25 amino acids. Overall, the repeat domains of the ankyrins are 32–39% identical with the 830-amino acid repeat domain of tankyrase. Together, these observations indicate that tankyrase is related to the ankyrin family and as such may play a structural role in the cell. Apart from the ANK repeat domain, however, there was no detectable homology between tankyrase and ankyrins.

The carboxy terminal domain of tankyrase contained another motif postulated to function in protein-protein interaction. SAM (sterile alpha motif) is a 65–70 amino acid domain found in 1–3 copies in a diverse group of proteins implicated in developmental processes [Ponting, *Protein Science*, 4:1928–1930 (1995); Schultz et al., *Protein Science*, 6:249–253 (1997)]. An alignment of this motif with three unrelated SAM-containing proteins is presented in FIG. 1C. Two types of interactions have been shown for SAM domains; homo- or heterotypic interaction with other SAM domains [Barr et al., *Mol. Cell Biol.*, 16:5597–5603 (1996)] or binding to SH2 domains via phosphorylation of a conserved tyrosine [Stein et al., *J. Biol. Chem.*, 271:23588–23593 (1996)]. Since the SAM domain of tankyrase does not contain the conserved tyrosine required for binding SH2 domains, its binding partner is likely to be another SAM domain.

Finally, a 150 amino acid domain in the carboxyl terminus of tankyrase showed homology to poly(ADP-ribose) polymerase (PARP), a highly conserved nuclear protein, found in most eukaryotes except *S. cerevisiae* [for review see: de Murcia and de Murcia, *Trends Biochemical Sciences*, 19:172–176 (1994); Jeggo, *Curr. Biol.*, 8:R49–51 (1998); Lindahl et al., *Trends in Biochemical Sciences*, 20:405–411 (1995)]. In response to DNA damage, PARP catalyses the formation of poly(ADP-ribose) onto a protein acceptor using $NAD^+$ as a substrate. The homology falls in the catalytic domain of PARP, which binds $NAD^+$. Structural analysis indicated that this domain consisted of secondary structure units (multiple β strands and one alpha helix; indicated in FIG. 1D) [Ruf et al., *Proc. Natl. Acad. Sci. USA*, 93:7481–7485 (1996)], that form a cavity known as the NAD+-binding fold, a tertiary structure that is also present in all ADP-ribosylating toxins [Domenighini et al., *Mol. Microbiol.*, 14:41–50 (1994)]. PARP and the toxins constitute a superfamily of ADP-ribosyl-transferases [Ruf et al., *Proc. Natl. Acad. Sci. USA*, 93:7481–7485 (1996)]. The identities between tankyrase and PARP fall within these secondary structure units. FIG. 1D shows an alignment of human and Drosophila (derived from a 508 nt sequence in the EST database) tankyrase, human and Drosophila PARP, and an uncharacterized human cDNA in the database (KIA0077), which, like tankyrase, is homologous to PARP only in this domain. Several features are worth noting, First, all the amino acids in PARP that have been implicated in $NAD^+$-binding or catalysis are conserved in tankyrase, including critical amino acids that are conserved between the eukaryotic PARPs and the prokarytic ADP-ribosylating toxins, DT (dimeric diphtheria toxin) and ETA (exotoxin A from *Pseudomonas aeruginosa* [see Ruf et al., *Proc. Natl. Acad. Sci. USA*, 93:7481–7485 (1996)]). Second, human and Drosophila tankyrase are even more conserved (80% identical) in this region than human and Drosophila PARP (65% identical), highlighting the importance of this domain in tankyrase. Third, the three human proteins (tankyrase, PARP and KIA0077) share 28–30% identity in this domain. Here again, all the critical residues are conserved and most of the identical residues fall within the secondary structure units that form the $NAD^+$-binding fold. Thus, based upon these observations it is concluded that tankyrase is a new member of the ADP-ribosyl-transferase superfamily of enzymes with PARP as its closest relative. The conservation of the amino acids critical for $NAD^+$-binding and catalysis suggests that tankyrase encodes a similar enzymatic activity.

Figure 2A:
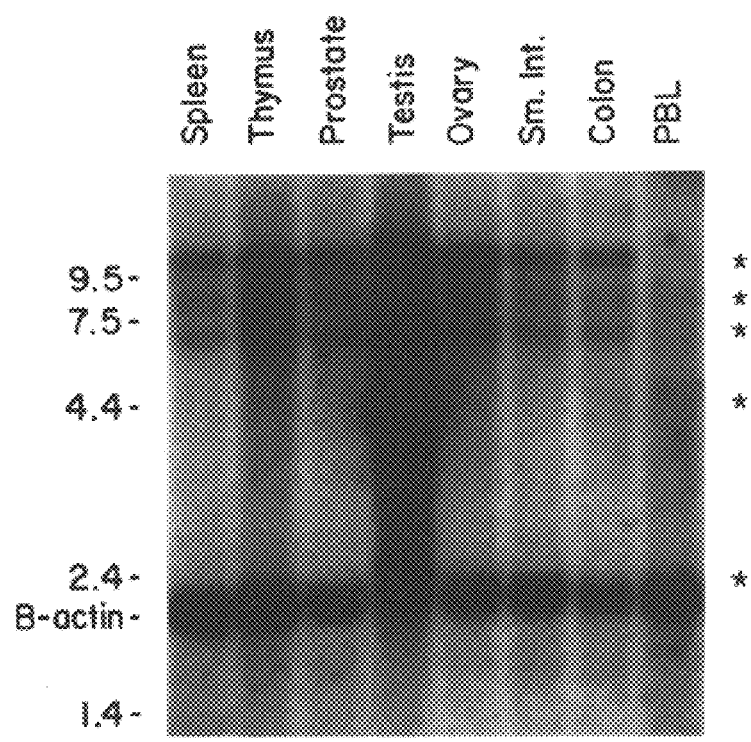
FIGS. 2A–2B show the expression of tankyrase mRNA and protein.

Tankyrase is ubiquitously expressed: The expression pattern of tankyrase was evaluated by Northern blot analysis of RNA from a variety of human tissues (FIG. 2A). The tankyrase cDNA hybridized to three mRNAs of ~6, 8, and 10 kb with the same ubiquitous expression pattern as TRF1 and TRF2 [Broccoli et al., *Nature Gen.*, 17:231–235 (1997); Chong et al., *Science*, 270:1663–1667 (1995)]. The tankyrase message was particularly abundant in testis where there were two additional messages of ~2.5 and 4.5 kb. The 4.2 kb tankyrase cDNA isolated from the testis library is large enough to represent the abundant 4.5 kb transcript suggesting that this cDNA is nearly full-length. The larger transcripts present in most tissues may be due to longer 3' untranslated regions. Indeed, DNA sequence analysis of a tankyrase cDNA isolated from a HeLa cell library revealed the same sequence as the full-length 4.5 kb cDNA but, had an additional 5 kb of 3' untranslated sequence. When the most 3' 1 kb of this cDNA was used as a probe in a Northern blot, it hybridized exclusively to the largest (10 kb) transcript supporting the idea that the larger transcripts reflect additional 3' untranslated regions (UTRs).

Figure 2B:
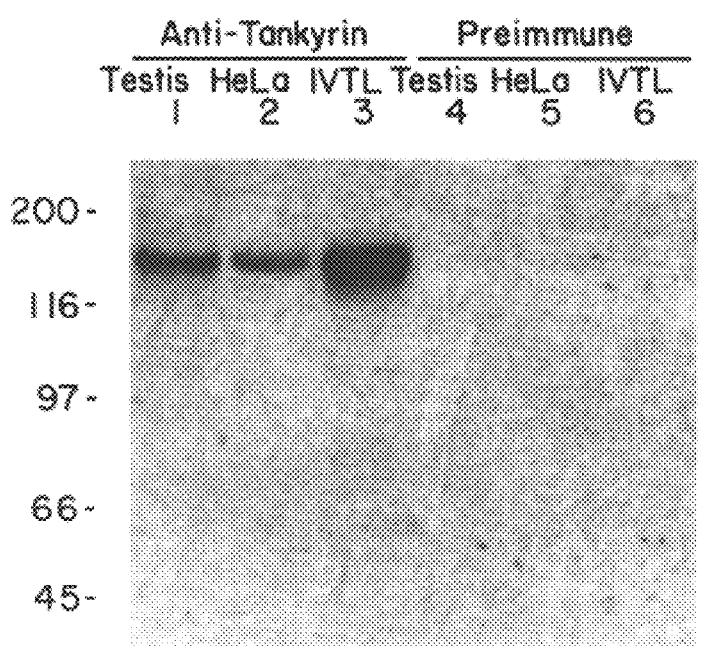

To analyze the expression of the tankyrase protein, polyclonal antibodies were raised against a subdomain of tankyrase (indicated as Ank2, see FIG. 1A), expressed as a fusion protein in *E. coli*. Immunoblot analysis with affinity purified anti-ankyrin antibodies (FIG. 2B) revealed a single polypeptide of ~142 kD (the predicted molecular weight) in rat testis cell extracts (FIG. 2B, lane 1) and human HeLaI whole cell lysates (FIG. 2B, lane 2). The protein co-migrated with immunoreactive, in vitro translated tankyrase (FIG. 2B, lane 3), indicating that the cDNA encoded the full-length protein. Consistent with the idea that the multiple tankyrase transcripts differed only in their 3' untranslated regions, only a single immunoreactive polypeptide was expressed despite the complex pattern of transcripts (particularly in testis). The specificity of the antibody was confirmed by the lack of reactivity with preimmune serum (FIG. 2B, lanes 4–6).

Localization of exogenous tankyrase to telomeres is TRF1-dependent: Initially the tankyrase cDNA was used to determine the subcellular localization of the protein. A construct was prepared containing the full-length tankyrase cDNA which also encoded a FLAG epitope at the N-terminus of tankyrase. The construct was expressed by transient transfection in HeLaI cells. Indirect immunofluorescence with anti-FLAG antibodies indicated a cytoplasmic staining pattern for the transfected protein (FIG. 3A). Co-staining with TRF1 antibody (FIG. 3B) showed that tankyrase did not co-localize with TRF1 and, in fact, was excluded from the nucleus (FIG. 3C). When tankyrase was co-transfected with TRF1 it displayed a different pattern of localization; FLAG-tankyrase was translocated from the cytoplasm to the nucleus (FIG. 3E) where it co-localized with TRF1 in a punctate pattern (FIG. 3G) consistent with a telomeric localization. Similarly, in co-transfected mitotic cells FLAG-tankyrase co-localized with TRF1 in a pattern consistent with localization to telomeres (FIG. 3K). A telomeric staining pattern for tankyrase was only observed in cells overexpressing TRF1. Note that in these experiments the anti-TRF1 antibodies did not distinguish between exogenous and endogenous TRF1. However, TRF1-transfected cells were easily recognized by the increased level of TRF1 expression. These findings confirmed the two hybrid result by showing that TRF1 and tankyrase interacted in mammalian cells and also suggested that transport of tankyrase into the nucleus to telomeres was linked to TRF1 synthesis (see below).

Figure 4A:
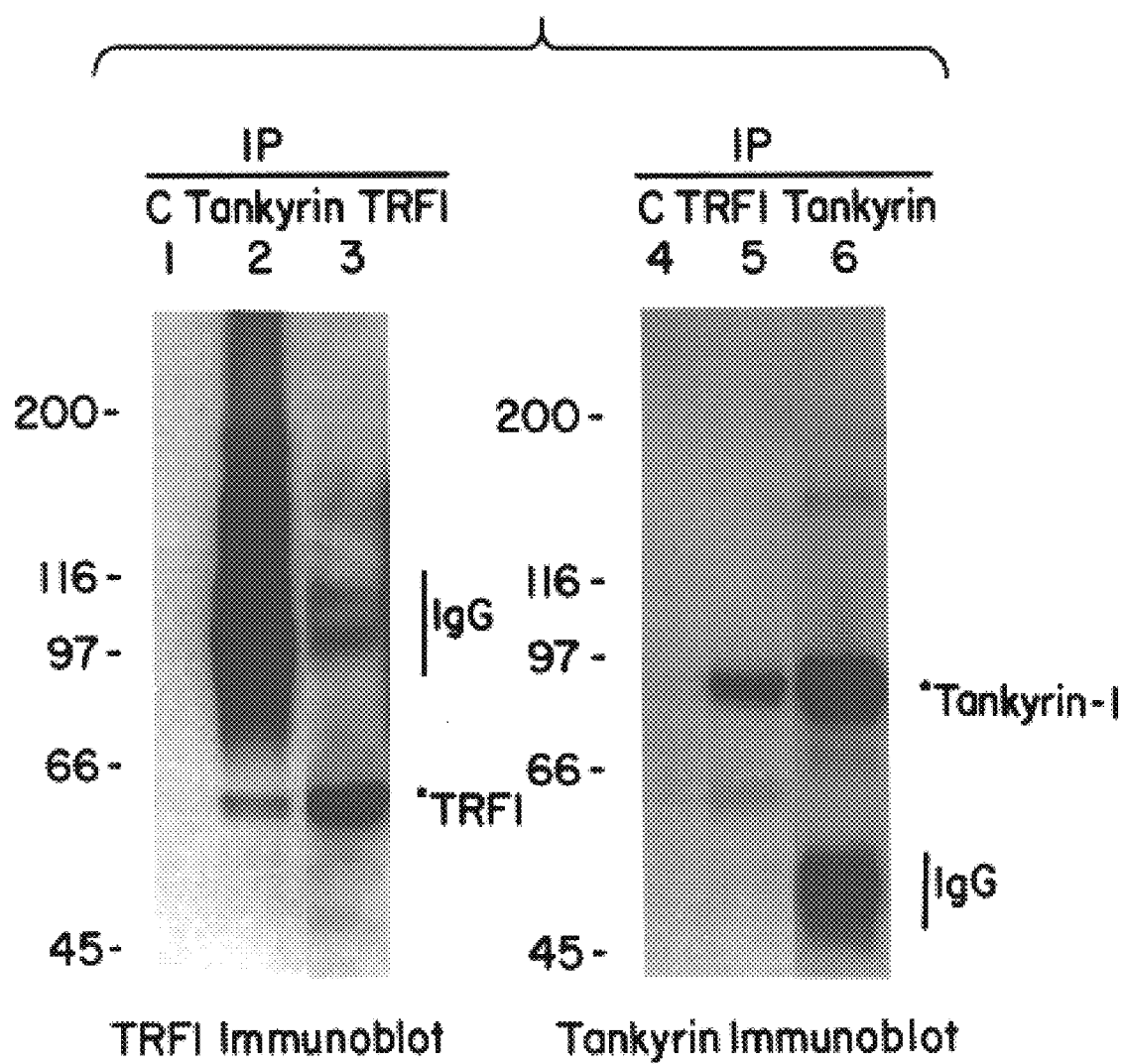
FIGS. 4A–4B show the analysis of tankyrase and TRF1 interaction by immunoprecipitation and the two-hybrid assay.

To determine if tankyrase and TRF1 were actually physically complexed in cells, co-immunoprecipitation experiments were performed on transfected cell extracts. Due to a low efficiency of transient expression with transfection of full-length tankyrase, these studies were done with a more effective expression plasmid, tankyrase-1, containing a partial tankyrase ORF, (TR1L4, see FIG. 1A) with a FLAG epitope at its amino terminus. Indirect immunofluorescence with anti-FLAG antibody indicated that transfected tankyrase-1, like full-length tankyrase, localized to telomeres when co-transfected with TRF1. Extracts prepared from tankyrase-1/TRF1 transfected cells were subjected to immunoprecipitation analysis followed by immunoblotting. As shown in FIG. 4A, TRF1 was immunoprecipitated with anti-tankyrase antibodies (FIG. 4A, lane 2), and conversely, transfected tankyrase-1 was immunoprecipitated with anti-TRF1 antibodies (FIG. 4A, lane 5), demonstrating that the proteins were complexed in vivo. Only a small fraction of the total protein in each case was co-immunoprecipitated, consistent with the staining pattern in co-transfected cells (see for example FIG. 3E).

Figure 4B:
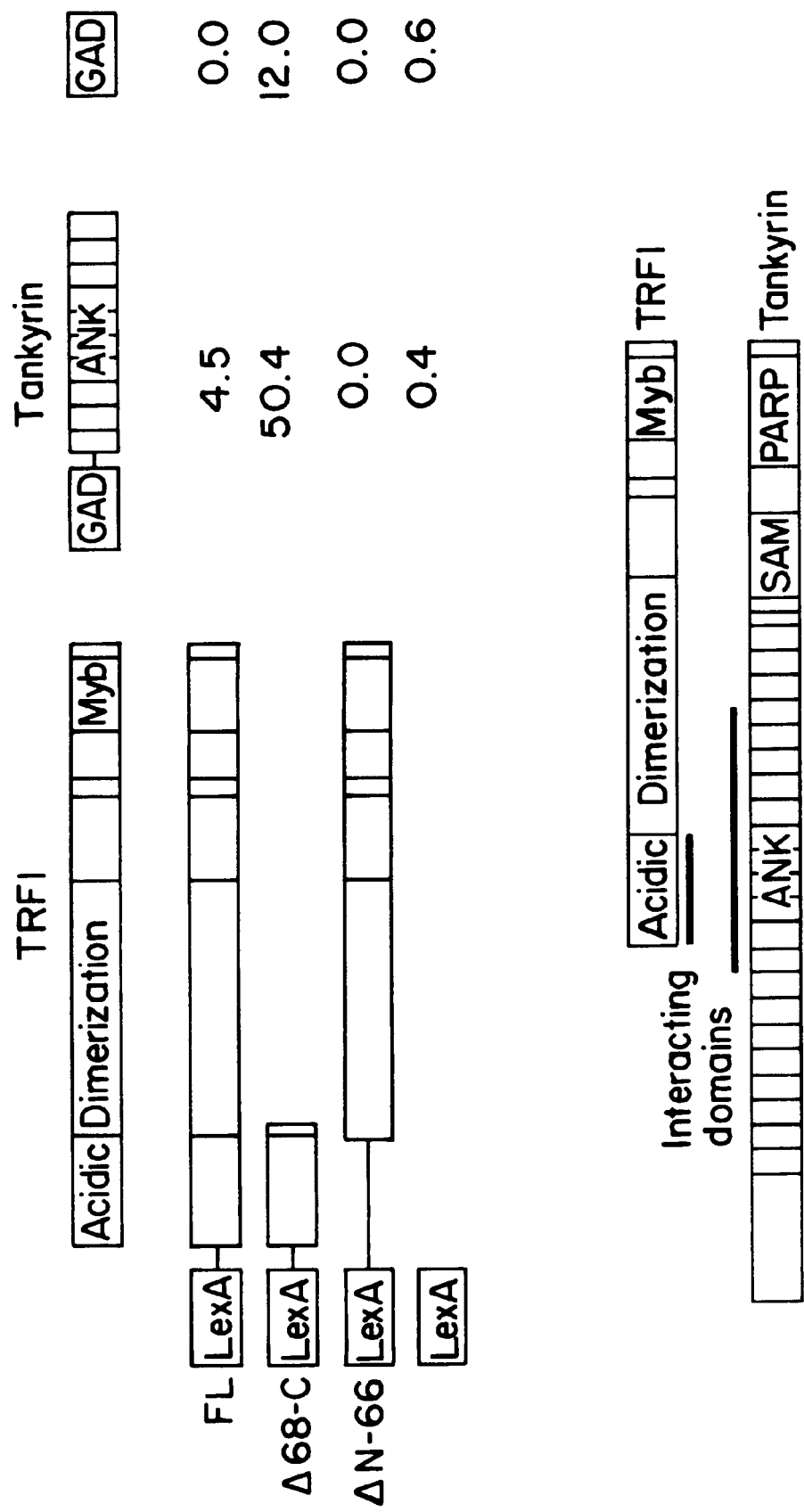

Two-hybrid analysis was used to determine the interacting domains between tankyrase and TRF1. The smallest isolate from the original two-hybrid screen, TR1L-12 (see FIG. 1A), consisted of only 10 internal ANK repeats (ANK repeats 9–19), thereby demonstrating that tankyrase interacted with TRF1 through its ANK repeats. To determine the tankyrase-interacting domain in TRF1, two-hybrid analysis was performed with the 10-ANK repeat domain of TR1L-12 fused to the GAL4 activation domain (GAD-tankyrase) and full-length and deletion constructs of TRF1 fused to LexA. As shown in FIG. 4B co-expression of full-length TRF1 fused to LexA (LexA-FL) and GAD-tankyrase resulted in transcriptional activation of the lacZ reporter gene that was dependent upon both TRF1 and tankyrase sequences. As observed previously, the amino-terminal acidic domain of TFR1 (LexAd68-C) activated transcription even in the absence of tankyrase sequences in the GAD fusion partner. However, this activity increased significantly from 12.0 to 50.4 units when the GAD fusion partner contained tankyrase sequences. Deletion of the acidic domain of TRF1 (ΔN66-LexA) abolished the interaction with GAD-tankyrase. Together, these results demonstrated that the amino-terminal acidic domain of TRF1 is necessary and sufficient for interaction with the 10-ANK repeat domain of tankyrase.

Figure 5A:
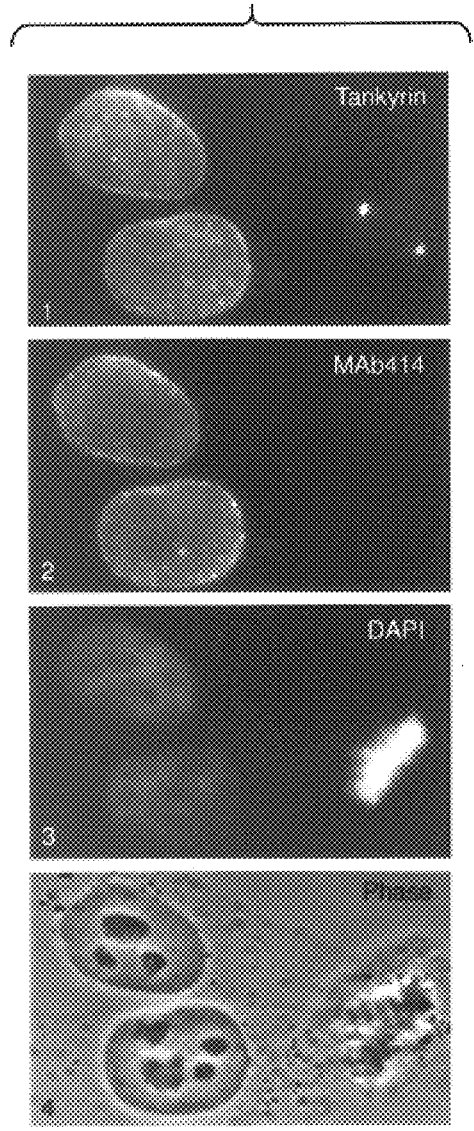
FIGS. 5A–5C show endogenous tankyrase localizes to nuclear pore complexes.

Tankyrase is located at nuclear pore complexes in interphase and at centrosomes in mitosis: Next the subcellular localization of endogenous tankyrase was determined. Indirect immunofluorescence of HeLaI cells with affinity purified anti-tankyrase antibody indicated that tankyrase localized to the nuclear envelope in interphase and to the centrosomes in mitosis (FIG. 5A, panel 1). This staining pattern was blocked if the antibodies were preincubated with the recombinant tankyrase fusion protein (Ank2, see FIG. 1A), against which the antibody was raised, prior to immunfluorescence. The punctate nuclear rim stain was reminiscent of nuclear pore complex stain. Indeed co-staining of cells with MAb414, a monoclonal antibody that recognizes a family of nuclear pore complex proteins [Davis and Blobel, Cell, 45:699–709 (1986)], revealed an identical staining pattern at the nuclear rim, but not at centrosomes (FIG. 5A, compare panels 1 and 2).

Figure 5B:
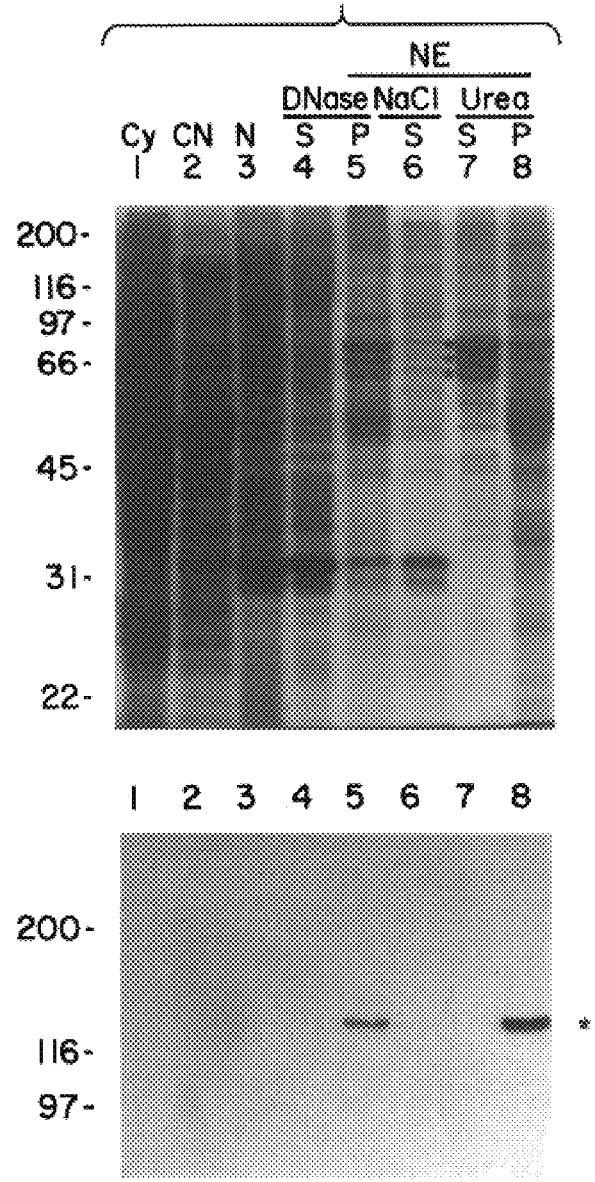

The nuclear envelope localization of tankyrase was confirmed by immunoblot analysis of subcellular fractions of rat liver (FIG. 5B). Tankyrase was highly enriched in the nuclear envelope fraction (FIG. 5B, lane 5) and remained bound even after extraction with 0.5 M NaCl and 8 M urea (FIG. 5B, lane 8), indicating a tight association with nuclear envelopes. Resistance to extraction by 8 M urea (which removes tightly associated, peripheral membrane proteins including the nuclear lamins; see FIG. 5B, top panel, lane 7) is usually a property of integral membrane proteins However, tankyrase is unlikely to be an integral membrane protein since its predicted amino acid sequence does not indicate a strong transmembrane domain since it does not associate with microsomal membranes when co-translated in vitro. The tight association between tankyrase and nuclear envelopes reflects an unusual property of the ANK repeat domain.

Figure 5C:
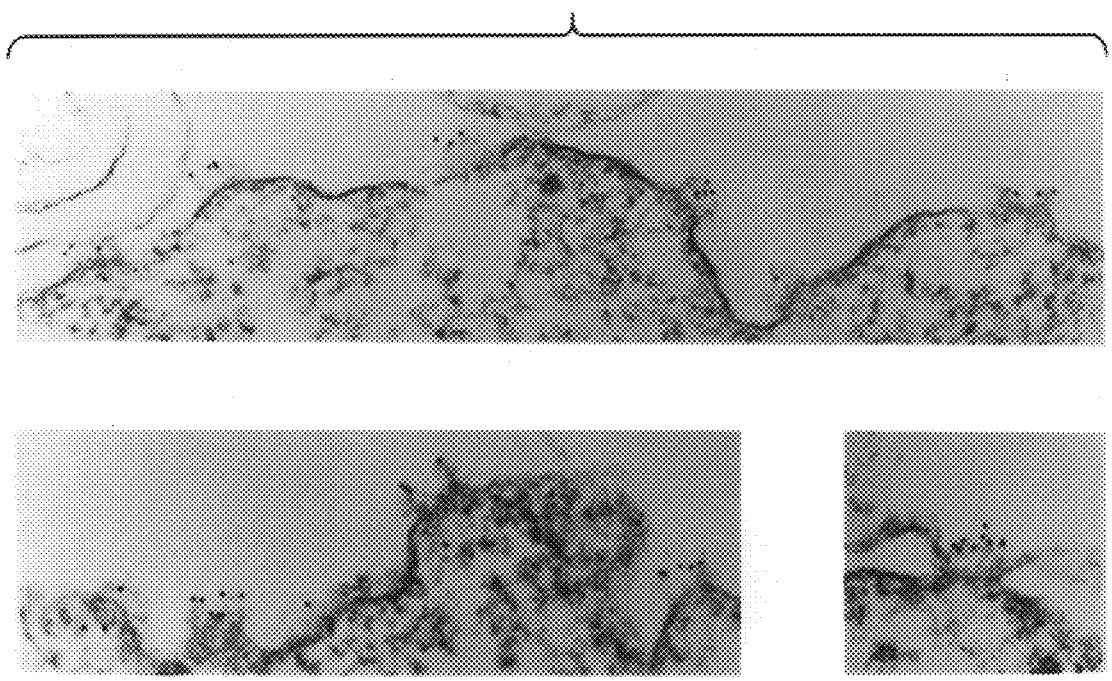

To further characterize the nuclear envelope localization, immunogold electron microscopy with affinity purified anti-tankyrase antibodies was performed. As expected, (from the cell staining and fractionation), tankyrase localized to the nuclear envelope, specifically to the cytoplasmic face of the nuclear pore complex (FIG. 5C). Tankyrase often appeared to be located on the tips of the fibers that emanate from the nuclear pore complex into the cytoplasm. In addition to the predominant cytoplasmic location, occasionally one or two gold particles appeared on the nuclear face of the nuclear pore complex. The low level of signal on the nuclear side of the nuclear pore complex could be due to an inaccessibility of tankyrase to the antibody. Immunogold labeling of tankyrase at the nuclear pore complex required pretreatment of cells with Triton X-100 prior to fixation, suggesting that tankyrase epitopes are inaccessible. Nonetheless, under the conditions used, tankyrase localizes predominantly to the cytopolasmic face of the nuclear pore complex and a minor fraction, possibly more, to the nuclear side.

As shown in FIG. 5A tankyrase localized to the centrosome in mitosis. Tankyrase first appeared at the centrosome in early prophase and remained there throughout mitosis to telophase, reaching maximal accumulation at metaphase (see FIG. 5A, panel 1). The centrosomal location of tankyrase was further investigated by a series of double-label immunofluorescence experiments with antibodies directed against previously characterized centrosomal proteins, including centrin, a component of the centrioles [reviewed in Salisbury, Curr. Opin. Cell Biol., 7:39–45 (1995)], γ-tubulin, a pericentriolar matrix protein [Stearns et al., Cell, 65:825–836 (1991); Zheng et al., Cell, 65:817–823 (1991)] and NuMA, which accumulates around the pericentriolar matrix protein upon nuclear envelope breakdown

Figure 6A:
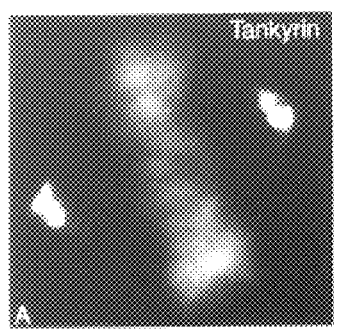
FIGS. 6A–6L show that the endogenous and exogenous tankyrase localize around the pericentriolar matrix in mitotic cells.
Figure 6B:
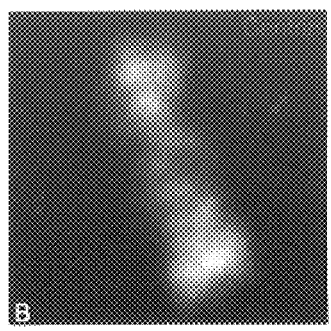
Figure 6C:
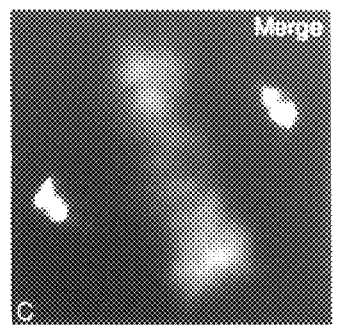
Figure 6D:
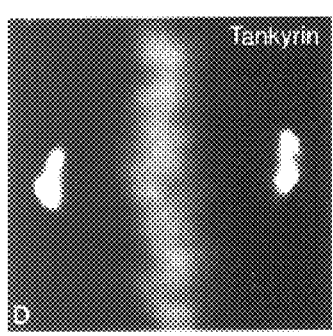
Figure 6E:
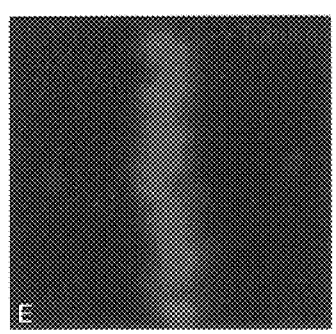
Figure 6F:
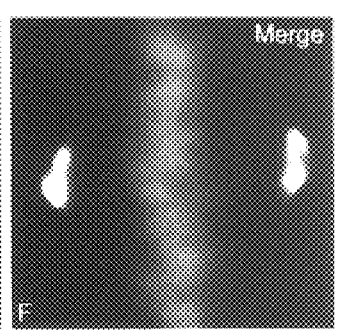
Figure 6H:
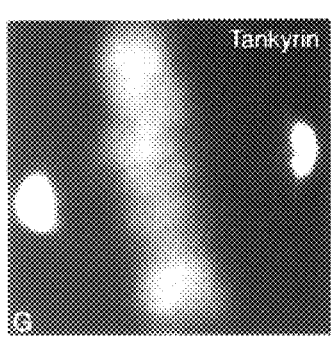
Figure 6G:
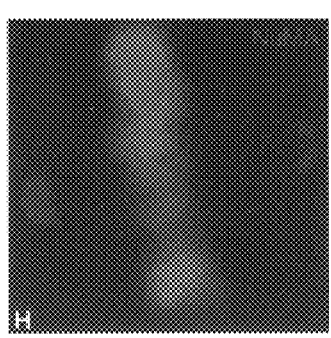
Figure 6I:
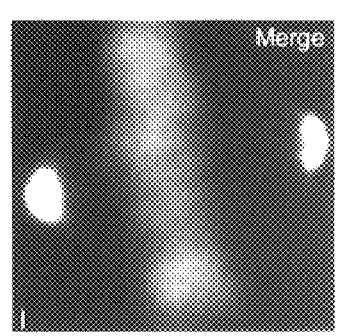
Figure 6J:
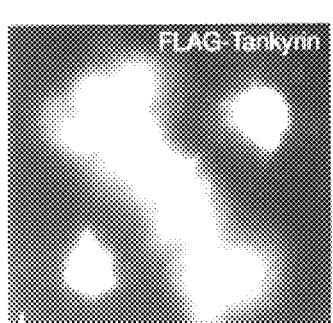
Figure 6K:
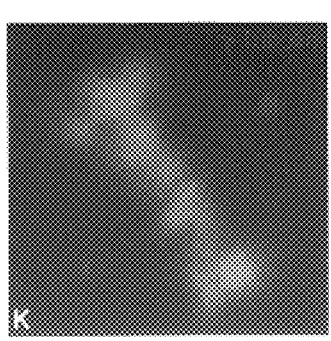
Figure 6L:
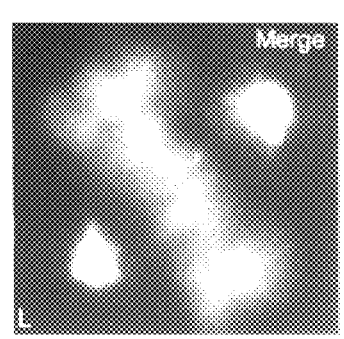

[reviewed in Cleveland, *Trends Cell Biol.*, 5:60–64 (1995)]. As shown in FIG. 6, tankyrase did not co-localize with centrin (FIG. 6C), or γ-tubulin (FIG. 6F), indicating that tankyrase is not an integral component of the centrosome per se. However, tankyrase did co-localize with NuMA (FIG. 6I) around the pericentriolar matrix region. To confirm the centrosomal location of tankyrase by a means other than the anti-tankyrase antibodies, the distribution of exogenous FLAG-tankyrase at mitosis was determined. As shown in FIGS. 6I and 6L, FLAG-tankyrase localized to the centrosome, around the pericentriolar matrix region, similar to endogenous tankyrase (as shown by γ-tubulin staining, FIG. 6K).

Tankyrase is located at telomeres throughout the cell cycle: The absence of endogenous tankyrase at telomeres was surprising since exogenous tankyrase interacted with TRF1 and co-localized with TRF1 in a telomeric staining pattern. The possibility therefore existed that the amount of tankyrase at telomeres was below the level of detection and therefore, cells with longer telomeres might allow detection of telomeric tankyrase. To address this, indirect immunofluorescence was performed on HeLaI.2.11 cells, a clonal isolate of HeLaI cells with long telomeres (greater than 20 kb). For these experiments cells were fixed with methanol which eliminates the nuclear envelope staining pattern observed with formaldehyde-fixed cells (see FIG. 5A, panel 1). As shown in FIG. 7A, staining of methanol-fixed HeLaI.2.11 cells with anti-tankyrase antibodies revealed a nuclear punctate pattern in interphase cells which coincided with TRF1 staining (FIG. 7C), indicating a telomeric location for tankyrase in interphase. Unlike the pattern seen in formaldehyde-fixed cells (FIG. 5A, panel 1), the methanol fixation also revealed a residual cytoplasmic localization for tankyrase (FIG. 7A). To determine if tankyrase localized to chromosomes during mitosis, indirect immunofluorescence was performed on metaphase spreads from HeLaI.2.11 cells. In order to detect tankyrase, metaphase spreads were first swollen in hypotonic buffer, followed by formaldehyde fixation in hypotonic buffer. As shown in FIG. 7D, tankyrase was detected predominantly at chromosome ends. Most metaphase chromosomes had tankyrase at their ends where it colocalized with TRF1 (FIG. 7F). Occasionally, telomeres were observed without tankyrase, but this appeared to be a random occurrence and most likely reflected difficulty in detection. These results demonstrate that tankyrase localizes to telomeres in vivo throughout the cell cycle.

Figure 9A:
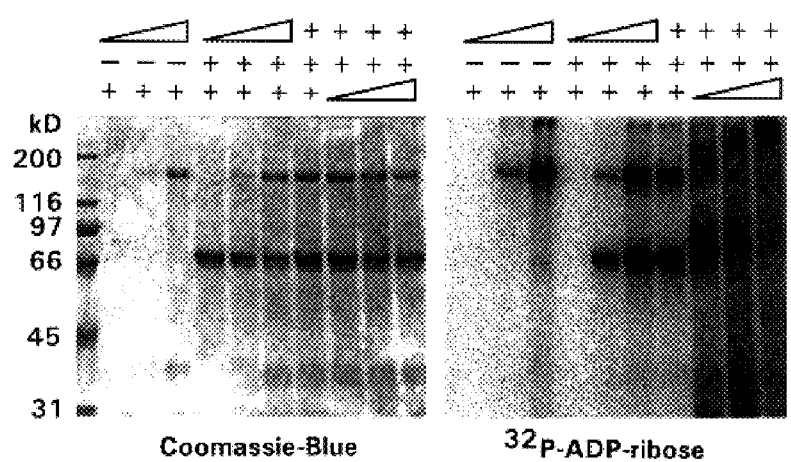
FIGS. 9A–9E demonstrates that tankyrase is a poly(ADP-ribose) polymerase that inhibits TRF1 in vitro.
Figure 9B:
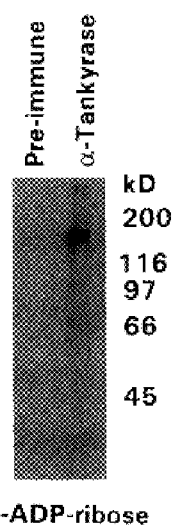

To investigate whether tankyrase has PARP activity, baculovirus-derived recombinant protein was tested in an assay that measures the addition of radiolabeled ADP-ribose to protein acceptors using [$^{32}$P]NAD$^+$ as a substrate (see Methods, above). Incubation of tankyrase in the presence of 1.3 μM radiolabeled NAD$^+$ produced $^{32}$P-labeled species that co-migrated with tankyrase, suggested that tankyrase has the ability ADP-ribosylates itself (FIG. 9A). Higher concentrations of NAD$^+$ (0.04 to 1 mM) yielded much larger products, likely reflecting the addition of poly(ADP-ribose) to tankyrase. The generation of ADP-ribosylates tankyrase depended on the concentration of tankyrase (FIG. 9A), and was eliminated by heat-inactivation of the enzyme. The ADP-ribosylating activity could also be removed by immunoprecipitation with anti-tankyrase antibody (FIG. 9B, and see Methods). These results indicate that the PARP activity is an intrinsic property of tankyrase.

Tankyrase also has the ability to modify TRF1. At low NAD$^+$ concentration (1.3 μM) the ADP-ribosylates products co-migrated with TRF1, whereas at higher NAD$^+$ concentrations (0.04 to 1 mM) the slower and variable mobility of the labeled products suggested poly(ADP-ribosyl)ation of TRF1 (FIG. 9A). Inspection of Coomassie-Blue stained SDS-PAGE gels did not reveal a larger molecular weight species upon tankyrase-mediated TRF1 modification, indicating that only a small fraction of the TRF1 in the reactions was modified even at high tankyrase concentrations. Thus, tankyrase functions as a processive poly(ADP-ribose) polymerase under these conditions. TRF2 is not a substrate for modification in vitro, as might be expected from the lack of protein-protein interactions between TRF2 and tankyrase.

Figure 9C:
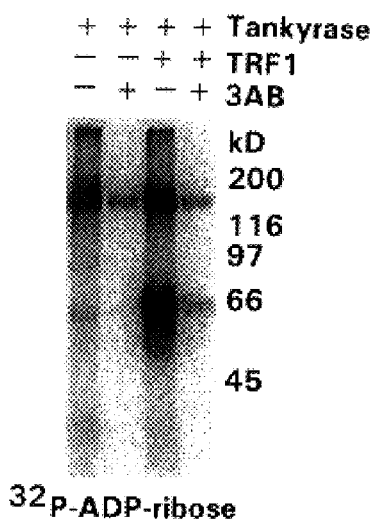
Figure 9D:
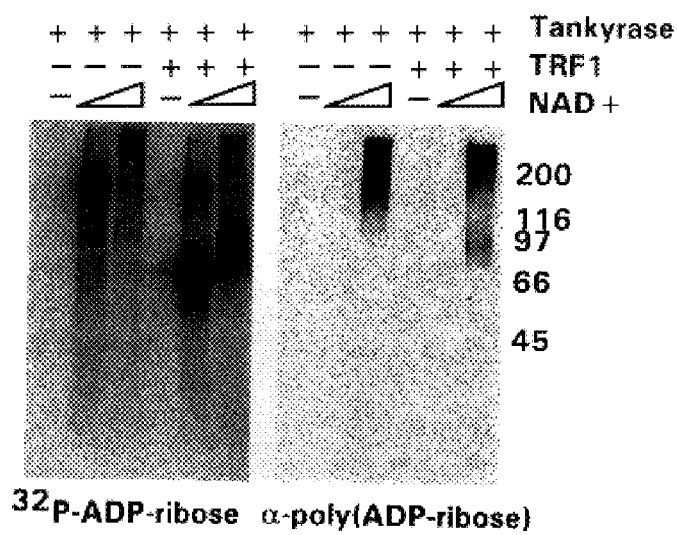

To confirm that the labeling reaction with tankyrase was analogous to PARP-catalyzed poly(ADP-ribosyl)ation, the specific PARP inhibitor 3-aminobenzamide (3AB) was added to the reactions [Purnell and Whish, Biochem J. 185:775 (1980)]. Modification of both TRF1 and tankyrase was strongly inhibited by 3AB (FIG. 9C). Furthermore, modified tankyrase and TRF1 reacted with a monoclonal antibody raised against poly(ADP-ribose) (FIG. 9D, see Methods above) consistent with their carrying ADP-ribose polymers. These data indicate that tankyrase is a genuine poly(ADP-ribose) polymerase with at least two specific substrates, TRF1 and tankyrase itself.

Figure 9E:
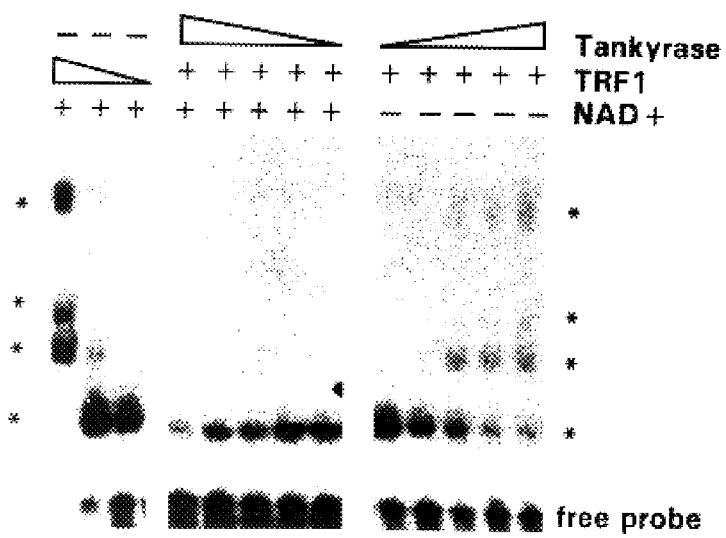

The effect of tankyrase on the telomeric DNA binding activity of TRF1 was determined by in vitro gel-shift assays using a double-stranded array of $[TTAGGG]_{12}$ as a probe (see Methods, above). TRF1 binds to DNA as a homodimer and several such dimers can occupy one $[TTAGGG]_{12}$ molecule at high TRF1 concentrations (FIG. 9E). When TRF1 was incubated with baculovirus-derived tankyrase in absence of NAD$^+$, a slight stimulation of the TRF1 DNA binding activity occurred, resulting in the formation of higher order complexes especially at high tankyrase concentrations. However, this stimulation of TRF1 also occurred with total insect cell protein, and was therefore unlikely to represent a specific effect of tankyrase. A similar non-specific enhancement of TRF1 was previously reported for β-casein and several other proteins [Chong et al. *Science* 270:1663 (1995)]. In contrast, when NAD$^+$ was included in the TRF1-tankyrase mixtures, a drastic reduction of the TRF1 activity resulted (FIG. 9E). This effect was dependent on the addition of active tankyrase (FIG. 9E), consistent with ADP-ribosylation being the cause of the TRF1 inhibition.

Discussion

TRF1 mediates localization of tankyrase to telomeres: Only a fraction of total cellular tankyrase resided in the nucleus at the telomere. The present data indicated that, in fact, transfected tankyrase was excluded from the nucleus. Inspection of the primary sequence of tankyrase does not reveal a convincing match to a consensus NLS (nuclear localization signal), raising the question of how tankyrase gets into the nucleus. The demonstration that co-transfection of TRF1 with tankyrase resulted in translocation of tankyrase to the nucleus, suggested the possibility of a "piggy back" mechanism. Thus, newly-synthesized TRF1 (which contains two overlapping bipartide NLSs [Chong et al., *Science,* 270:1663–1667 (1995)]) could bind to the ANK repeat domain in tankyrase and carry it to telomeres. Interestingly, a recent report identified ANK repeats within several different proteins as cis-acting NLSs [Sachdev et al., *Mol. Cell Biol.,* 18:2524–2534 (1998)]. Thus, perhaps a more general function of ANK repeat domains is to mediate interaction between a non NLS-containing ANK repeat protein with an NLS-containing protein, thereby allowing regulated import of the former by the latter. In this scenario, tankyrase localization to the telomere could be tightly regulated by TRF1 synthesis.

An alternative and not necessarily exclusive mechanism of tankyrase localization to telomeres might occur at mitosis, when upon break down of the nuclear envelope, tankyrase would gain access to both soluble and telomere-bound TRF1. Interesting, in co-transfected mitotic cells, tankyrase was almost exclusively found at telomeres (FIG. 31), whereas exogenous TRF1 was found at telomeres and throughout the cell (FIG. 3F). Similarly in cotransfected interphase cells, tankyrase co-localized with TRF1 to telomeres, but not with overexpressed TRF1 in the nucleoplasm (FIG. 3G). These observations suggest that tankyrase has a higher affinity for telomere-bound versus free TRF1. Thus, the telomeric complex could serve as a high-density source of tankyrase binding sites. A high concentration of TRF1 sites may be required for efficient tankyrase binding since two-hybrid analysis (see FIG. 4B) indicates a weak affinity for tankyrase for TRF1. Recent studies demonstrate that TRF1 can promote parallel pairing of telomeric tracts in vitro, provided that the telomeric tracts are long and the concentration of TRF1 is high [Griffith et al., *J. Mol. Biol.*, 278:79–88 (1998)]. Thus it was proposed that long telomeres with sufficient TRF1 could induce intramolecular pairing resulting in a coiled higher order structure at telomeres. Such a substrate could provide a means for long telomeres to recruit tankyrase for the negative regulation of telomere length (see model in FIG. 8B and below).

Tankyrase at nuclear pore complexes: Immunogold electronmicroscopy showed that tankyrase was located specifically at the tips of the fibers that emanate from the nuclear pore complex into the cytoplasm (FIG. 5C). This location is likely to be the entry site of a multiple docking site pathway by which substrates move through the nuclear pore complex. Indeed, only two other mammalian proteins have been localized to the tips of the cytoplasmic fibers, SUMO1-modified RanGAP1 which like tankyrase, also localizes to the mitotic centrosome [Mahajan et al., *Cell*, 88:97–107 (1997); Matunis et al., *J. Cell Biol.*, 135:1457–1470 (1996)] and the nucleoporin Nup358 [Wu et al., *J. Biol. Chem.*, 270:14209–14213 (1995); Yokoyama et al., *Nature*, 376:184–188 (1995)]. SUMO1-modified RanGAP1 and Nup358 bind to each other [Mahajan et al., *Cell*, 88:97–107 (1997); Matunis et al., *J. Cell Biol.*, 135:1457–1470 (1996)] and to Ran, the Ras-like GTPase that serves as the molecular switch for bi-directional transport through the nuclear pore [reviewed in Rush et al., *Bioessays*, 18:103–112 (1996)]. In addition, Nup358 contains short peptide repeats (a feature common to a subset of nucleoporins) which have been proposed to serve as docking sites for import substrate-receptor complexes as they move through the nuclear pore [Radu et al., *Cell*, 81:215–222 (1995)]. Tankyrase might use its SAM domain or ANK repeats to bind to the fibers or to Nup358, to localize to nuclear pore complex fibers.

Tankyrase's localization could be significant to the port of entry for nuclear traffic. Tankyrase could play a structural role at this site and (like ankyrins) serve as a linker between the cytoplasmic fibers of the nuclear pore complex and the cytoskeleton. At this location, its PARP-like activity could play a role in regulating nuclear transport. Alternatively, tankyrase's location at the nuclear pore complex may serve to provide a ready pool of tankyrase waiting to be picked up by TRF1 and translocated through the nuclear pore complex to telomeres, thus allowing its localization to telomeres to be tightly controlled by TRF1.

Tankyrase at the centrosome: possible relevance to meiosis: It has been demonstrated by indirect immunofluorescence herein that tankyrase is not an integral component of the centrosome per se but rather is located around the pericentriolar matrix where it co-localizes with NuMA (FIG. 6I). Like Nuda, tankyrase could be associating with the microtubules that emerge from the centrosome. NuMA exists in a complex with cytoplasmic dynein and dynactin and appears to be required for mitotic spindle pole assembly and stabilization [Merdes et al., *Cell*, 87:447–458 (1996)]. Therefore tankyrase, may play a role in spindle function or stability.

Figure 8A:
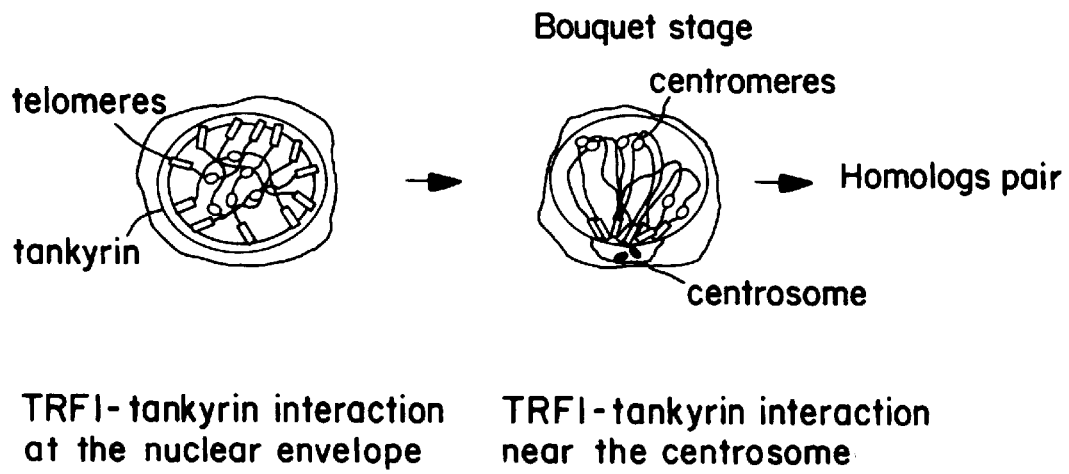
FIGS. 8A–8B show the role of human tankyrase in meiosis and telomere length regulation.

This is the first report of a protein that localizes to both telomeres and centrosomes. At first glance it is difficult to imagine a connection between these two structures. Normally it is not telomeres, but rather, centromeres that associate with the mitotic centrosome. Association between telomeres and the centrosome does occur but it is during meiosis (FIG. 8A), not mitosis. In mammalian cells during prophase of meiosis I (in a process that may be that may be essential for the pairing and subsequent recombination of homologous chromosomes), telomeres attach to the nuclear envelope and gather at one pole of the nucleus to form the bouquet stage [Bass et al., *J. Cell Biol.*, 137:5–18 (1998); Scherthan et al., *J. Cell Biol.*, 134:1109–1125 (1996)]. Interestingly, the base of the bouquet is always juxtapositioned to the centrosome and early cytological evidence indicates a connection between the centrosome and telomeres [Dernberg et al., In Telomeres, Blackburn and Greider, eds. (Cold Spring Harbor Press), pp. 295–338 (1995)]. Tankyrase could play multiple roles in this process (FIG. 8A). First, tankyrase could play a structural role (like ankyrins) and mediate attachment of telomeres to the inner nuclear membrane. Second, tankyrase could act as a sink at the centrosome to recruit telomeres to the base of the bouquet. Consistent with a proposed role in meiosis, abundant and alternative tankyrase transcripts in testis tissue was observed (FIG. 2A). In addition, immunoblot analysis on purified cell populations from rate testis indicated that tankyrase was highly expressed in meiotic prophase I. Although it is not yet known if TRF1 functions in meiosis, its ability to promote parallel pairing of telomeric tracts in vitro [Griffith et al., *J. Mol. Biol.*, 278:79–88 (1998)] would be consistent with such a role. Interestingly Taz1p, the *S. pombe* telomeric protein with structural and functional similarity to TRF1, was recently found to play a critical role in prophase of meiosis I, during the horse tail stage. Here telomeres cluster at the spindle pole body (SPB, the yeast equivalent of a centrosome) and move the nucleus to facilitate alignment of homologous chromosomes [Chikashige et al., *Science*, 264:270–273 (1994); Chikashige et al., *EMBO J.*, 16:193–202 (1997)]. Taz1p, is involved in connecting telomeres to the SPB, the horse-tail movement, and the subsequent segregation and recombination of homologous chromosomes [Cooper et al., *Nature*, 392:828–831 (1998); Nimmo et al., *Nature*, 392:825–828 (1998); for review see de Lange, *Nature*, 392:753–754 (1998)]

A role for ADP ribosylation in telomere length regulation: The carboxy terminal domain of tankyrase displays significant homology to the catalytic domain of PARP, a nuclear protein that in response to DNA damage catalyzes the formation of poly(ADP-ribose) onto glutamate residues in a protein acceptor using $NAD^+$ as a substrate. This homology reflects enzymatic activity in tankyrase since all of the key amino acids that are required for NAD+binding and catalysis are conserved between tankyrase and PARP Functional studies that eliminate PARP activity, either with inhibitor, dominant negative mutants, or gene disruption, all point to a role for PARP in the maintenance of genome integrity. While the most likely physiological substrate of PARP is PARP itself, other in vitro recognized substrates include histones, nuclear lamins, RNA polymerase II and DNA replication enzymes including: topoisomerase I, DNA polymerase α and β, and DNA ligase II [Oei et al., *Biochemistry*, 37:1465–1469 (1998); Yoshihara et al., *Biochem. Biophys. Res. Commun.*, 128:61–67 (1985); reviewed in Althaus and Richter, *Mol. Biol. Biochem. Biophys.*, 37:1–237 (1987)]. Although the molecular mechanism is unknown, one model suggests that PARP acts to inhibit or block recombination at sites of DNA damage, thus allowing normal DNA repair to occur. Inhibition of recombination could be achieved through several different mechanisms: PARP could modify itself, generating a structure at DNA breaks that blocks access to recombination enzymes, PARP could modify and inactivate another protein required for recombination, or PARP could induce changes in higher order chromatin structure by modifying histones or other chromatin-associated proteins.

Previous studies indicate that TRF1 functions as a negative regulator of telomere length. Since TRF1 does not affect the expression of telomerase, it may inhibit telomerase in cis, at individual chromosome ends. According to this model (see FIG. 8B), long telomeres would recruit a large mass of TRF1, resulting in inhibition of telomerase. As a result, the telomeres would shorten until the amount of TRF1 is no longer sufficient to inhibit the elongation reaction. Thus, telomeres are proposed to be in a dynamic equilibrium between an open state in which telomerase is active at the termini and a close state in which the enzyme is switched off at each individual end. Recent in vitro studies have shown that TRF1 does not affect telomerase activity even when TRF1 is positioned immediately adjacent to 3' end used for addition of TTAGGG repeats, suggesting that the role of TRF1 in telomerase modulation is most likely indirect.

Figure 8B:
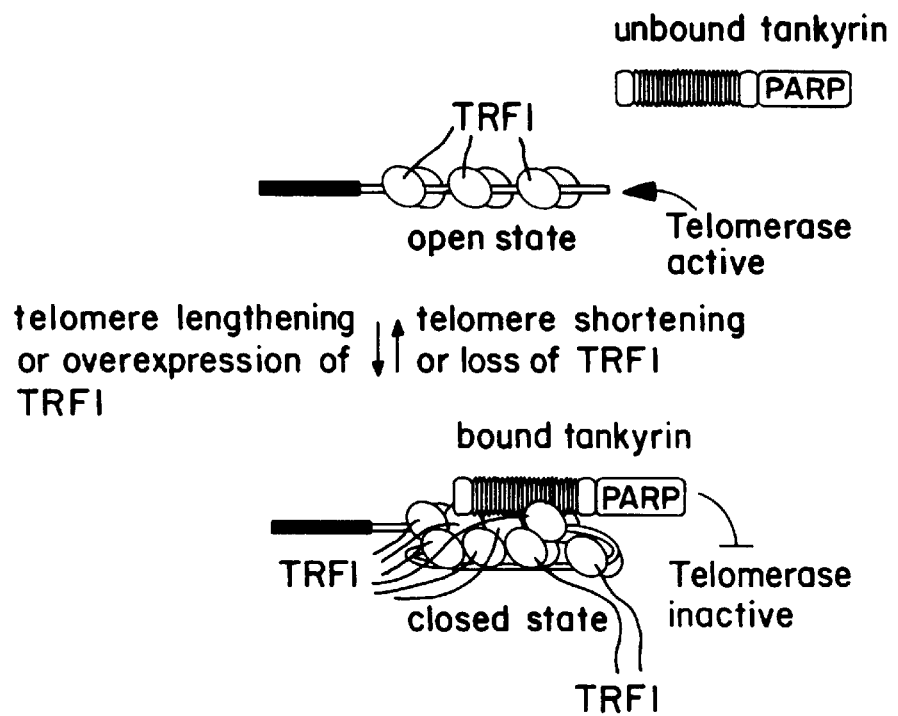

The identification of tankyrase now suggests an alternative mechanism by which TRF1 may regulate telomerase-mediated telomere maintenance. Based on the presence of the PARP domain in tankyrase, the telomeric tankyrase could add ADP-ribose units directly to telomerase, inactivating the enzyme or otherwise limiting the elongation reaction. Alternatively, tankyrase could act indirectly, perhaps using one of the many indirect targets proposed for the mode of action of PARP. A potential target could be TRF1 itself, particularly since its amino terminal domain contains many glutamate residues. Long telomeres preferentially could recruit tankyrase via interaction with TRF1, resulting in a local increase in PARP (-like) activity on long telomeres (FIG. 8B). In agreement, the data presented herein indicate that the amount of TRF1 on telomeres determines the abundance of tankyrase at chromosome ends. For instance, tankyrase at telomeres has only been detected in cells that harbor very long TTAGGG repeat arrays (containing large amounts of TRF1) or in cells that overexpress TRF1. Thus, in the proposed model, TRF1 functions as the sensor of telomere length and tankyrase relays this signal to telomerase via ADP ribosylation.

The identification of a telomeric poly(ADP-ribose) polymerase raises the possibility that the function of human telomeres is regulated by this type of protein modification. Since ADP-ribosylation usually inhibits protein activity [Reviewed in Altheas and Richer, Mol. Biol. Biochem Beefiest 37:1 (1987); Obi et al. Biochem. 37:1465 (1998)] tankyrase could act as a negative regulator of another factor acting at telomeres. From the in vitro studies disclosed herein, TRF1 is currently the most obvious candidate, since it is a substrate for tankyrase in vitro and ADP-ribosylation inhibits the ability of TRF1 to bind to telomeric DNA. However, the PARP activity of tankyrase could also be directed at other telomere-associated factors, including telomerase and (ADP-ribosyl)ation could enhance, rather than inhibit the activity of the target protein [Ruscetti et al. J. Biol. Chem. 273:14461(1998)] PARPs have previously been implicated in the cellular response to DNA damage (9). The presence of a PARP activity at telomeres could also indicate a role for tankyrase in the protection of telomeres from inappropriate DNA damage processing activities.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. A purified recombinant tankyrase obtained by expressing a nucleic acid operatively linked to an expression control sequence in a cell; wherein said cell has been transformed or transfected by said nucleic acid; wherein said nucleic acid encodes a tankyrase that has an amino acid sequence that has at least 25% identity with that of SEQ ID NO:2; and wherein said tankyrase comprises:
   a) an ankyrin-specific (ANK) repeat consensus domain;
   b) a sterile alpha motif (SAM) motif;
   c) a poly(ADP-ribose) polymerase (PARP)-related domain; and
   wherein said tankyrase has poly(ADP-ribosyl)ating activity.

2. A purified recombinant tankyrase fragment obtained by expressing a nucleic acid operatively linked to an expression control sequence in a cell; wherein said cell has been transformed or transfected by said nucleic acid; wherein said nucleic acid encodes a fragment of a tankyrase that can bind to the acidic domain of a telomeric repeat binding factor 1 (TRF1); wherein said fragment comprises at least a portion of the ANK repeat consensus domain of the tankyrase; and wherein said tankyrase comprises:
   a) an ankyrin-specific (ANK) repeat consensus domain;
   b) a sterile alpha motif (SAM) motif; and
   c) a poly(ADP-ribose) polymerase (PARP)-related domain; and
   wherein said tankyrase has poly(ADP-ribosyl)ating activity.

3. An isolated vertebrate tankyrase that binds to telomeric repeat binding factor 1 (TRF1), wherein the vertebrate tankyrase has an amino acid sequence that has at least 25% identity with that of SEQ ID NO:2, and comprises:
   a) an ankyrin-specific (ANK) repeat consensus domain;
   b) a sterile alpha motif (SAM) motif; and
   c) a poly(ADP-ribose) polymerase (PARP)-related domain; and
   wherein the tankyrase has poly(ADP-ribosyl)ating activity.

4. The isolated tankyrase of claim 3 that is a mammalian protein.

5. An isolated tankyrase that comprises the amino acid sequence of SEQ ID NO:2, or SEQ ID NO:2 with a conservative amino acid substitution.

6. A chimeric and/or fusion protein comprising the isolated tankyrase of claim 3.

7. An isolated tankyrase fragment that can bind to the acidic domain of a telomeric repeat binding factor 1 (TRF1); wherein said fragment comprises at least a portion of the ANK repeat consensus domain of the tankyrase; and wherein said tankyrase comprises:
   a) an ankyrin-specific (ANK) repeat consensus domain;
   b) a sterile alpha motif (SAM) motif; and
   c) a poly(ADP-ribose) polymerase (PARP)-related domain; and
   wherein said tankyrase has poly(ADP-ribosyl)ating activity.

8. A chimeric and/or fusion protein comprising the fragment of claim 7.

9. An isolated tankyrase fragment that comprises the amino acids 436 to 796 of SEQ ID NO:2, or the amino acids 436 to 796 of SEQ ID NO:2 with a conservative amino acid substitution.

10. An isolated tankyrase fragment that comprises the amino acids 181 to 1005 of SEQ ID NO:2, or the amino acids 181 to 1005 of SEQ ID NO:2 with a conservative amino acid substitution.

11. An isolated tankyrase fragment that comprises the amino acids 336 to 1163 of SEQ ID NO:2, or the amino acids 336 to 1163 of SEQ ID NO:2 with a conservative amino acid substitution.

12. An isolated tankyrase fragment containing a PARP domain comprising the amino acids 1159 to 1314 of SEQ ID NO:2, or the amino acids 1159 to 1314 of SEQ ID NO:2 with a conservative amino acid substitution.

13. An isolated tankyrase fragment containing a SAM motif comprising the amino acids 1023 to 1088 of SEQ ID NO:2, or the amino acids 1023 to 1088 of SEQ ID NO:2 with a conservative amino acid substitution.

14. A chimeric and/or fusion protein comprising the isolated tankyrase fragment of claim 9.

15. A chimeric and/or fusion protein comprising the tankyrase fragment of claim 10.

16. A chimeric and/or fusion protein comprising the isolated tankyrase fragment of claim 11.

17. A chimeric and/or fusion protein comprising the tankyrase fragment of claim 12.

18. A chimeric and/or fusion protein comprising the isolated tankyrase fragment of claim 13.

19. An isolated truncated tankyrase having an amino acid sequence selected from the group consisting of amino acids 1–640 of SEQ ID NO:2, amino acids 1–640 of SEQ ID NO:2 with a conservative amino acid substitution, amino acids 1–881 of SEQ ID NO:2, amino acids 1–881 of SEQ ID NO:2 with a conservative amino acid substitution, SEQ ID NO:8, SEQ ID NO:8 with a conservative amino acid substitution, SEQ ID NO:10, and SEQ ID NO:10 with a conservative amino acid substitution.

20. A chimeric and/or fusion protein comprising the truncated tankyrase of claim 19.

21. A fragment of a tankyrase comprising an HPS domain having an amino acid sequence selected from the group consisting of amino acids 1 to 180 of SEQ ID NO:2 and 1 to 180 of SEQ ID NO:2 with a conservative amino acid substitution.

22. A chimeric and/or fusion protein comprising the fragment of claim 21.

23. A purified recombinant tankyrase obtained by expressing a nucleic acid operatively linked to an expression control sequence in a cell; wherein said cell has been transformed or transfected by said nucleic acid; and wherein said nucleic acid hybridizes to the complementary strand of SEQ ID NO:1 in 40% formamide with 5× or 6× SSC.

24. A chimeric and/or fusion protein comprising the fragment of claim 23.

25. An isolated recombinant tankyrase fragment obtained by expressing a nucleic acid operatively linked to an expression control sequence in a cell; wherein said cell has been transformed or transfected by said nucleic acid; wherein said nucleic acid hybridizes to the complementary strand of SEQ ID NO:1 in 40% formamide with 5× or 6×SSC.

26. A chimeric and/or fusion protein comprising the fragment of claim 25.

27. An isolated vertebrate tankyrase that binds to telomeric repeat binding factor 1 (TRF1), wherein the vertebrate tankyrase is encoded by a nucleic acid that hybridizes to the complementary strand of SEQ ID NO:1 in 40% formamide with 5× or 6×SSC; and wherein the tankyrase has poly (ADP-ribosyl)ating activity.

28. A chimeric and/or fusion protein comprising the tankyrase of claim 27.

29. An isolated recombinant tankyrase fragment that can bind to the acidic domain of a telomeric repeat binding factor 1 (TRF1); wherein said fragment comprises at least a portion of the ANK repeat consensus domain of the tankyrase; and wherein said fragment is encoded by a nucleic acid that hybridizes to the complementary strand of SEQ ID NO:1 in 40% formamide with 5× or 6×SSC.

30. A chimeric and/or fusion protein comprising the fragment of claim 29.

31. A fragment of a tankyrase comprising the amino acid sequence of SEQ ID NO:2; wherein said fragment can be used to raise an antibody to said tankyrase.

32. A chimeric and/or fusion protein comprising the fragment of claim 31.

* * * * *